United States Patent
Lee et al.

(10) Patent No.: US 11,678,852 B2
(45) Date of Patent: *Jun. 20, 2023

(54) X-RAY IMAGING APPARATUS AND METHOD FOR CONTROLLING THE SAME

(71) Applicant: SAMSUNG ELECTRONICS CO., LTD., Suwon-si (KR)

(72) Inventors: Ho Jun Lee, Suwon-si (KR); Geun Tae Bae, Anyang-si (KR); Ju Hwan Kim, Suwon-si (KR); Sung Nam Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,829

(22) Filed: Jul. 11, 2022

(65) Prior Publication Data

US 2022/0346736 A1   Nov. 3, 2022

Related U.S. Application Data

(63) Continuation of application No. 16/921,367, filed on Jul. 6, 2020, now Pat. No. 11,382,585, which is a
(Continued)

(30) Foreign Application Priority Data

Aug. 25, 2015 (KR) .......................... 10-2015-0119877
Aug. 25, 2015 (KR) .......................... 10-2015-0119879
(Continued)

(51) Int. Cl.
*A61B 6/00* (2006.01)
*A61B 6/06* (2006.01)
*A61B 6/04* (2006.01)

(52) U.S. Cl.
CPC ............... *A61B 6/465* (2013.01); *A61B 6/04* (2013.01); *A61B 6/06* (2013.01); *A61B 6/4464* (2013.01);
(Continued)

(58) Field of Classification Search
None
See application file for complete search history.

(56) References Cited

U.S. PATENT DOCUMENTS 8,313,238 B2    11/2012  Takahashi
10,702,229 B2 *  7/2020  Lee .......................... A61B 6/06
(Continued)

FOREIGN PATENT DOCUMENTS

CN           1526360 A      9/2004
CN         102885637 A      1/2013
(Continued)

OTHER PUBLICATIONS

Communication dated Jan. 11, 2022 by the Chinese Patent Office for Chinese Patent Application No. 201610728357.0.
(Continued)

*Primary Examiner* — Hoon K Song
(74) *Attorney, Agent, or Firm* — Sughrue Mion, PLLC

(57) ABSTRACT

An imaging apparatus includes a camera to capture a camera image of a target disposed on an examination table; an X-ray source to generate and radiate X-rays; a memory to store imaging protocols; a display; and a controller. The controller is configured to receive information regarding a selection of an imaging protocol, identify a position of an imaging region of the target based on the camera image, the imaging region corresponding to the selection of the imaging protocol and the camera image being acquired with the examination table at a first distance from the X-ray source, control the display to display the camera image of the target and an indicator
(Continued)

indicating the imaging region on the camera image based on the identified position, and control the X-ray source to radiate the X-rays toward the target disposed on the examination table at a second distance from the X-ray source.

15 Claims, 56 Drawing Sheets

Related U.S. Application Data continuation of application No. 15/247,225, filed on Aug. 25, 2016, now Pat. No. 10,702,229.

(30) Foreign Application Priority Data

| Aug. 26, 2015 | (KR) | 10-2015-0120577 |
| Aug. 26, 2015 | (KR) | 10-2015-0120578 |
| Aug. 25, 2016 | (KR) | 10-2016-0108157 |

(52) U.S. Cl.
CPC .......... *A61B 6/467* (2013.01); *A61B 6/5241* (2013.01); *A61B 6/542* (2013.01); *A61B 6/545* (2013.01); *A61B 6/587* (2013.01)

(56) References Cited

U.S. PATENT DOCUMENTS

| 2002/0159564 | A1 | 10/2002 | Wang et al. | |
|---|---|---|---|---|
| 2009/0086885 | A1 | 4/2009 | Yamaguchi | |
| 2011/0013752 | A1 | 1/2011 | Takahashi | |
| 2013/0022172 | A1* | 1/2013 | Lee | A61B 6/465 378/63 |
| 2013/0077744 | A1 | 3/2013 | Kamiya | |
| 2013/0083894 | A1* | 4/2013 | Niebler | A61B 6/547 378/62 |
| 2013/0114793 | A1 | 5/2013 | Ohta | |
| 2014/0348296 | A1 | 11/2014 | Goossen et al. | |
| 2015/0228071 | A1 | 8/2015 | Jockel | |
| 2016/0081650 | A1 | 3/2016 | Okusu | |
| 2016/0374639 | A1 | 12/2016 | Becker | |

FOREIGN PATENT DOCUMENTS

| CN | 104602608 A | 5/2015 |
| EP | 2548509 A1 | 1/2013 |
| EP | 2609863 A1 | 7/2013 |
| EP | 2676609 A1 | 12/2013 |
| JP | 2007-29353 A | 2/2007 |
| JP | 2008-136773 A | 6/2008 |
| JP | 2009-82169 A | 4/2009 |
| JP | 2009-240477 A | 10/2009 |
| JP | 2011-229559 A | 11/2011 |
| JP | 2012-40156 A | 3/2012 |
| JP | 2014-144118 A | 8/2014 |
| JP | 2015-524729 A | 8/2015 |
| KR | 10-2013-0142850 A | 12/2013 |
| KR | 10-2015-0059450 A | 6/2015 |

OTHER PUBLICATIONS

Communication dated Aug. 4, 2021, from The China National Intellectual Property Administration in Application No. 201610728357.0.
Communication dated Dec. 25, 2020 by the National Intellectual Property Administration, PR China in corresponding Chinese Application No. 201610728357.0.
Communication dated Mar. 20, 2017, issued by the European Patent Office in counterpart European Application No. 16186173.7.
Communication dated Mar. 26, 2019, issued by the European Patent Office in counterpart European Application No. 16186173.7.
Communication dated Jul. 31, 2018, issued by the European Patent Office in counterpart European Application No. 16186173.7.

* cited by examiner

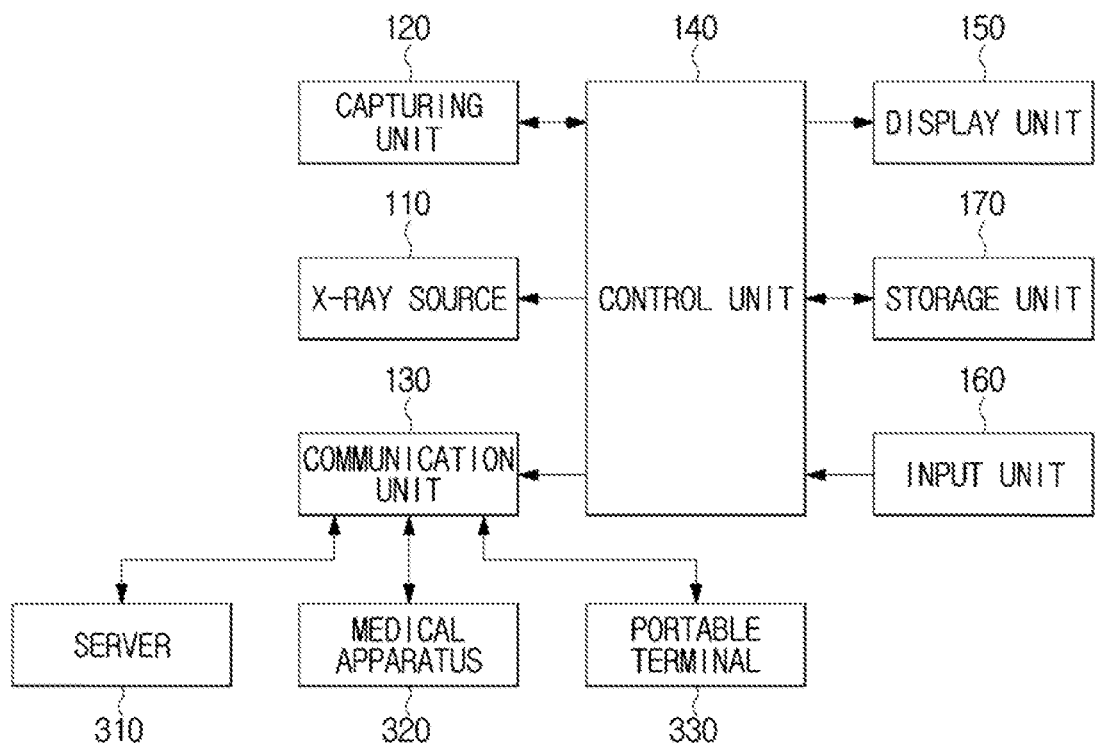

FIG. 6

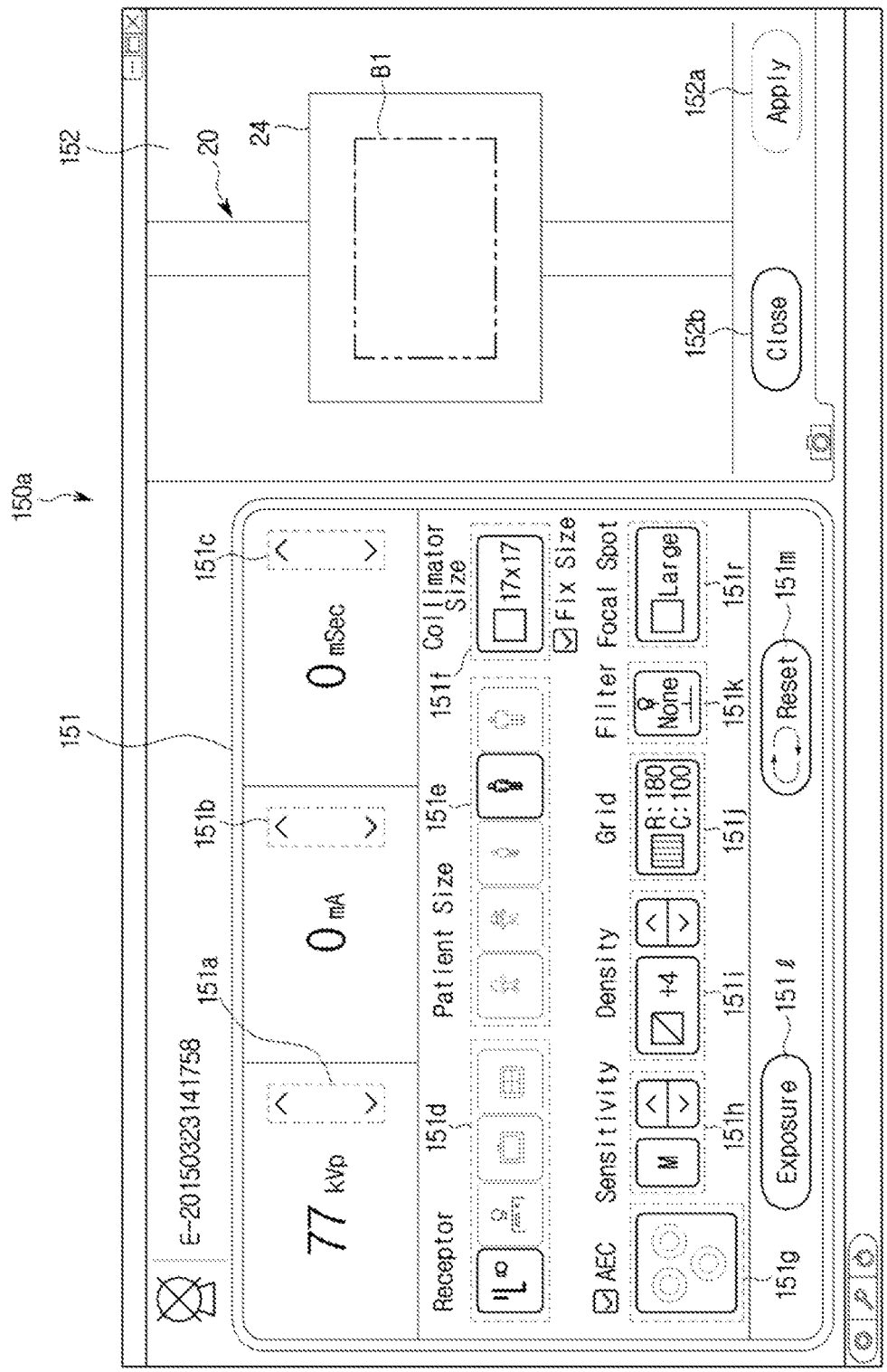

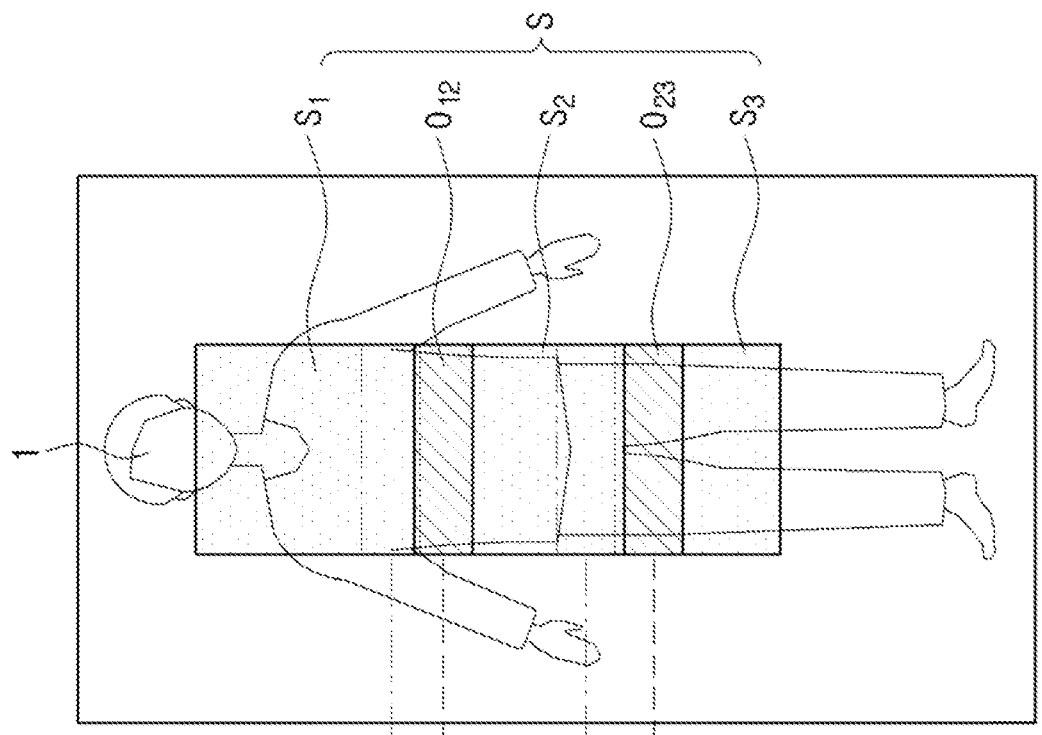
FIG.30
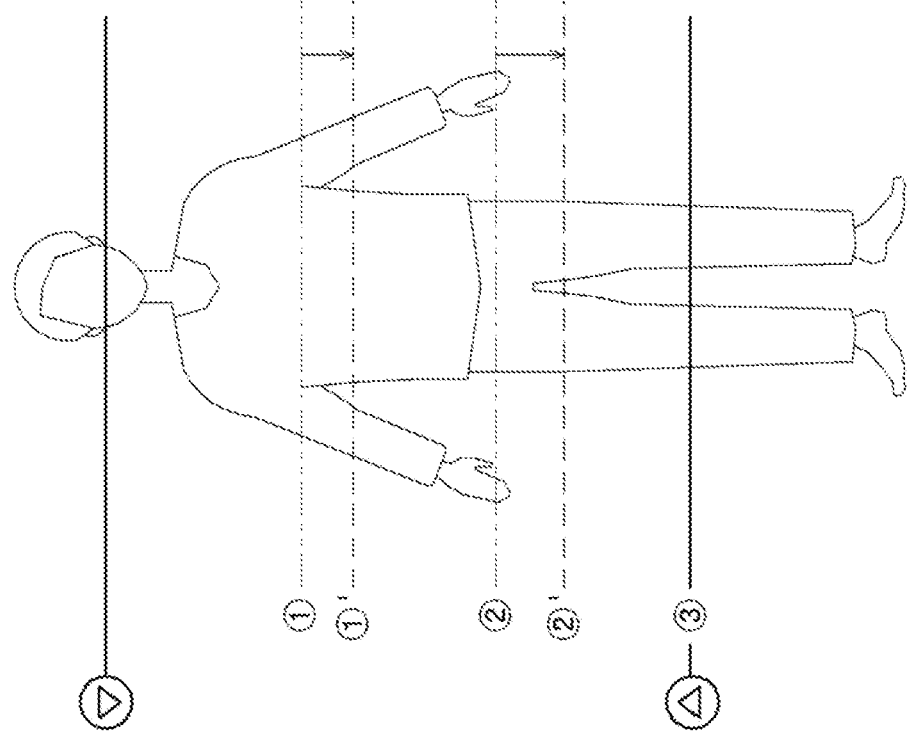

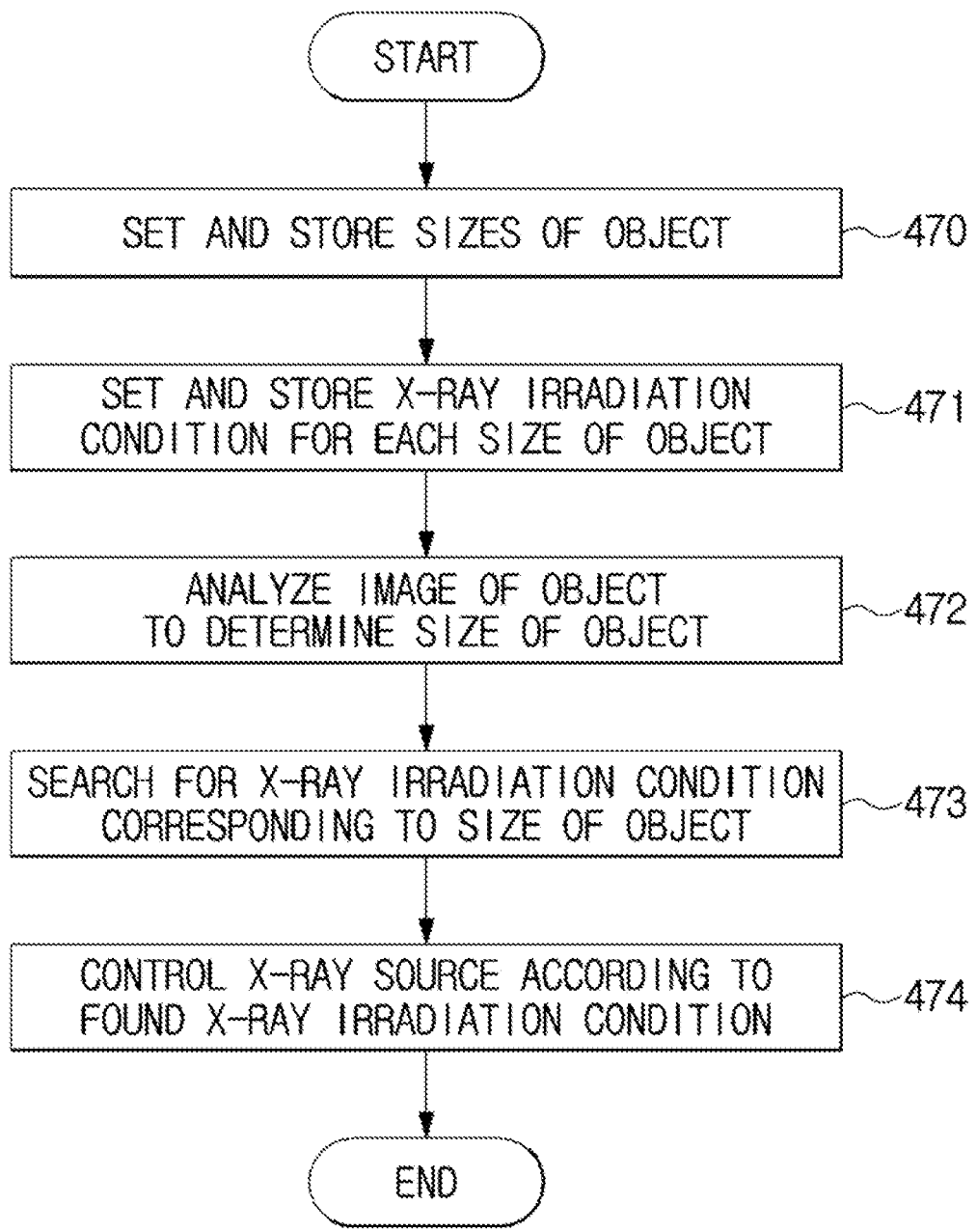

X-RAY IMAGING APPARATUS AND METHOD FOR CONTROLLING THE SAME

CROSS-REFERENCE TO RELATED PATENT APPLICATIONS

This is a continuation of application Ser. No. 16/921,367, filed Jul. 6, 2020, which is a continuation of application Ser. No. 15/247,225 filed Aug. 25, 2016, now U.S. Pat. No. 10,702,229, issued Jul. 7, 2020, which claims priority from Korean Patent Application Nos. 10-2015-0119877, 10-2015-0119879, 10-2015-0120578, 10-2015-0120577, and 10-2016-0108157 filed Aug. 25, 2015, Aug. 25, 2015, Aug. 26, 2015, Aug. 26, 2015, and Aug. 25, 2016, respectively, in the Korean Intellectual Property Office. The disclosures of all of the above applications are incorporated by reference herein in their entireties.

BACKGROUND

1. Field

Embodiments of the present disclosure relate to an X-ray imaging apparatus and a method for controlling the same.

2. Description of the Related Art

An X-ray imaging apparatus is an apparatus that irradiates an object with X-rays and analyzes X-rays that have been transmitted through the object to recognize an inner structure of the object. Since X-ray transmittance varies according to a tissue forming an object, an inner structure of the object may be imaged using an attenuation coefficient which is a numerical value of X-ray transmittance.

Since an X-ray irradiation region may be adjusted using a collimator, the X-ray irradiation region should be accurately set in consideration of an X-ray imaging portion, a feature of an object, etc. to prevent the object from being unnecessarily exposed to X-rays and being unnecessarily irradiated with X-rays.

A part which is desired to be imaged may not be entirely captured by a single imaging in some cases due to various reasons including a case in which the X-ray irradiation region is smaller than a portion to be imaged and a case in which a region to be detected by X-rays is smaller than a portion to be imaged.

In these cases, one X-ray image of the desired part may be obtained by dividing the portion to be imaged into a plurality of regions, capturing each of the plurality of regions by X-rays, and stitching the plurality of X-ray images acquired together.

SUMMARY

Therefore, it is an aspect of the present disclosure to provide an X-ray imaging apparatus that uses a camera image to set various types of parameters related to X-ray imaging including an X-ray irradiation region and automatically controls X-ray imaging, and a method for controlling the same.

Additional aspects of the disclosure will be set forth in part in the description which follows and, in part, will be obvious from the description or may be learned by practice of the disclosure.

According to an embodiment, an X-ray imaging apparatus includes a capturing unit that captures a camera image, an X-ray source on which a collimator adjusting an X-ray irradiation region is mounted, a storage unit that maps and stores an X-ray imaging region for each of a plurality of X-ray imaging protocols, an input unit that receives a selection of one of the X-ray imaging protocols from the plurality of X-ray imaging protocols, and a control unit that extracts an X-ray imaging region mapped to the selected X-ray imaging protocol from the camera image and controls the collimator such that the X-ray irradiation region corresponds to the extracted X-ray imaging region.

The input unit may receive a selection related to an X-ray imaging region to be mapped for each of the plurality of X-ray imaging protocols from a user.

The X-ray imaging apparatus may further include a display unit that displays a graphical object having a shape of an object to receive a selection related to the X-ray imaging region and displays an imaging window designating the X-ray imaging region by overlapping the imaging window on the graphical object.

When at least one of a position and size of the imaging window is adjusted through the input unit, the control unit may store a region corresponding to at least one of the adjusted position and size of the imaging window in the storage unit as the X-ray imaging region.

The X-ray imaging apparatus may further include a display unit that displays the camera image and displays the extracted X-ray imaging region by overlapping the extracted X-ray imaging region on the camera image.

The display unit may display a protocol list for receiving a selection of one X-ray imaging protocol from the plurality of X-ray imaging protocols and may display the camera image when a camera image display command is input through the input unit.

The input unit may receive a setting of an X-ray irradiation condition for each of the plurality of X-ray imaging protocols, and the storage unit may map and store the set X-ray irradiation condition for each of the plurality of X-ray imaging protocols.

When one of the plurality of X-ray imaging protocols is selected, the control unit may perform X-ray imaging by applying an X-ray irradiation condition mapped to the selected X-ray imaging protocol.

According to another embodiment, an X-ray imaging apparatus includes a display unit that displays a graphic user interface (GUI) for receiving a setting of an X-ray irradiation condition for each of a plurality of sizes of an object, a storage unit that maps and stores the X-ray irradiation condition for each of the plurality of sizes of the object according to an input, a capturing unit that captures a camera image, and a control unit that recognizes a size of an object shown in the camera image and performs X-ray imaging by applying an X-ray irradiation condition mapped to the recognized size of the object.

The display unit may display the recognized size of the object.

The storage unit may map and store and the X-ray irradiation condition for each of the plurality of sizes of the object and each of the X-ray imaging protocols.

When one of the plurality of X-ray imaging protocols is selected, the control unit may perform X-ray imaging by applying an X-ray irradiation condition mapped to the selected X-ray imaging protocol and the recognized size of the object.

According to yet another embodiment, an X-ray imaging apparatus includes a capturing unit that captures a camera image, an X-ray source on which a light source irradiating an X-ray irradiation region with visible rays is mounted, a control unit that calculates a position of the X-ray irradiation region in the camera image based on coordinate information of the X-ray source, extracts a light irradiation region which is irradiated with the visible rays displayed in the camera image, calculates a position of the extracted light irradiation region in the camera image, and determines that calibration is required when the position of the X-ray irradiation region and the position of the light irradiation region do not match each other, and a display unit that displays information related to the calibration when the calibration is required.

The display unit may display a first X-ray irradiation window corresponding to the calculated position of the X-ray irradiation region and a second X-ray irradiation window corresponding to the calculated position of the light irradiation region.

When at least one of positions, forms, and sizes of the first X-ray irradiation window and the second X-ray irradiation window do not match each other, the control unit may determine that the calibration is required.

When the calibration is required, the control unit may calculate a calibration parameter based on a difference between the first X-ray irradiation window and the second X-ray irradiation window.

The display unit may display the calculated calibration parameter.

The control unit may automatically perform the calibration based on the calculated calibration parameter.

The control unit may extract a boundary of an X-ray detector or a mounting unit on which the X-ray detector is mounted shown in the camera image to extract a detector boundary line, and may determine whether the X-ray detector and the X-ray source are aligned with each other based on an X-ray irradiation window displayed at the calculated position of the X-ray irradiation region or the calculated position of the light irradiation region and the extracted detector boundary line.

When intervals between a plurality of vertices forming the X-ray irradiation window and a plurality of vertices forming the detector boundary line entirely match each other, the control unit may determine that the X-ray detector and the X-ray source are aligned with each other.

When a center of the X-ray irradiation window and a center of the detector boundary line match each other, the control unit may determine that the X-ray detector and the X-ray source are aligned with each other.

The display unit may display the detector boundary line and the X-ray irradiation window by overlapping the detector boundary line and the X-ray irradiation window on the camera image.

The control unit may calculate a moving distance or a moving direction of the X-ray source or the X-ray detector for aligning the X-ray source and the X-ray detector with each other.

The control unit may move the X-ray source or the X-ray detector based on the calculated moving distance or moving direction.

The display unit may display the calculated moving distance or moving direction.

The display unit may display the X-ray irradiation window at the calculated position of the X-ray irradiation region or the calculated position of the light irradiation region and the X-ray imaging apparatus may further include an input unit that receives an adjustment command for adjusting a position or size of the X-ray irradiation window from a user.

When the X-ray irradiation window deviates from the boundary of the X-ray detector or the mounting unit on which the X-ray detector is mounted shown in the camera image due to an input adjustment command, the display unit may display a region deviating from the boundary.

According to still another embodiment, an X-ray imaging apparatus that generates a single X-ray image by stitching a plurality of X-ray images of a plurality of divided regions together includes a capturing unit that acquires a camera image, an X-ray source on which a collimator adjusting an X-ray irradiation region is mounted, a display unit that displays a plurality of divided windows showing sizes and positions of the plurality of divided regions by overlapping the plurality of divided windows on the camera image; and a control unit that controls the collimator to adjust a width of the X-ray irradiation region of at least one of the plurality of divided regions.

The X-ray imaging apparatus may further include an input unit that receives a command for controlling the width of the X-ray irradiation region, and the control unit may control the collimator according to an input command.

The control unit may control the collimator so that the width of the X-ray irradiation region matches a width of an object shown in the camera image.

The control unit may extract an outline of the object from the camera image and determine the width of the X-ray irradiation region based on a boundary between the extracted outline and a background.

The X-ray imaging apparatus may further include a plurality of automatic exposure control (AEC) sensors that control an amount of X-rays radiated from the X-ray source, and the control unit may select at least one of the plurality of AEC sensors based on the adjusted width of the X-ray irradiation region.

According to still another embodiment, an X-ray imaging apparatus generates a single X-ray image by stitching a plurality of X-ray images of a plurality of divided regions together, and includes a capturing unit that captures a camera image, a display unit that displays the camera image, and a control unit that determines whether an overlapping region in which the plurality of divided regions overlap the camera image is placed at a preset portion.

The control unit may move the overlapping region so that the overlapping region is not placed at the preset portion.

The display unit may display the overlapping region by overlapping the overlapping region on the camera image and may output a warning to a user when the overlapping region is placed at the preset portion.

The X-ray imaging apparatus may further include an input unit that receives a user command for moving the overlapping region.

According to an embodiment, a method for controlling an X-ray imaging apparatus includes mapping and storing an X-ray imaging region for each of a plurality of X-ray imaging protocols, receiving a selection of one of the X-ray imaging protocols from the plurality of X-ray imaging protocols, extracting an X-ray imaging region mapped to the selected X-ray imaging protocol from the camera image, and controlling a collimator such that an X-ray irradiation region corresponds to the extracted X-ray imaging region.

The mapping and storing of the X-ray imaging region may include receiving a selection related to an X-ray imaging region to be mapped for each of the plurality of X-ray imaging protocols from a user, and mapping and storing the X-ray imaging region for each of the plurality of X-ray imaging protocols according to an input.

According to another embodiment, a method for controlling an X-ray imaging apparatus includes displaying a GUI for receiving a setting of an X-ray irradiation condition for each of a plurality of sizes of an object, mapping and storing the X-ray irradiation condition for each of the plurality of sizes of the object according to an input, capturing a camera image, recognizing a size of the object shown in the camera image, and performing X-ray imaging by applying an X-ray irradiation condition mapped to the recognized size of the object.

The method may further include displaying the recognized size of the object.

According to yet another embodiment, a method for controlling an X-ray imaging apparatus includes irradiating an X-ray irradiation region with visible rays, capturing a camera image, calculating a position of the X-ray irradiation region in the camera image based on coordinate information of an X-ray source, extracting a light irradiation region irradiated with visible rays displayed in the camera image, calculating a position of the extracted light irradiation region in the camera image, determining that calibration is required when the position of the X-ray irradiation region and the position of the light irradiation region do not match each other, and displaying information related to the calibration when the calibration is required.

The method may further include extracting a boundary of an X-ray detector or a mounting unit on which the X-ray detector is mounted shown in the camera image to extract a detector boundary line, and determining whether the X-ray detector and the X-ray source are aligned with each other based on an X-ray irradiation window displayed at the calculated position of the X-ray irradiation region or the calculated position of the light irradiation region and the extracted detector boundary line.

The method may further include displaying the X-ray irradiation window at the calculated position of the X-ray irradiation region or the calculated position of the light irradiation region, and receiving an adjustment command for adjusting a position or size of the X-ray irradiation window from a user.

When the X-ray irradiation window deviates from the boundary of the X-ray detector or the mounting unit on which the X-ray detector is mounted shown in the camera image due to an input adjustment command, the method may further include displaying a region deviating from the boundary.

According to still another embodiment, a method for controlling an X-ray imaging apparatus includes capturing a camera image, displaying a plurality of divided windows showing sizes and positions of a plurality of divided regions by overlapping the plurality of divided windows on the camera image, and controlling a collimator to adjust a width of an X-ray irradiation region of at least one of the plurality of divided regions.

The method may further include receiving a command for controlling the width of the X-ray irradiation region, and the controlling the collimator may include controlling the collimator according to an input command.

The controlling the collimator may include controlling the collimator such that the width of the X-ray irradiation region matches a width of an object shown in the camera image.

The method may further include selecting at least one of a plurality of AEC sensors for each of the plurality of divided regions based on the adjusted width of the X-ray irradiation region.

According to still another embodiment, a method for controlling an X-ray imaging apparatus includes capturing a camera image, displaying the camera image, displaying a plurality of divided regions in which stitching imaging will be performed by overlapping the plurality of divided regions on the camera image, and determining whether an overlapping region in which the plurality of divided regions overlap the camera image is placed at a preset portion.

The method may further include moving the overlapping region when the overlapping region is placed at the preset portion.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 1 is a control block diagram of an X-ray imaging apparatus according to an embodiment;

FIGS. 6 and 7 are each a view illustrating an example of a screen displayed on a display unit of the X-ray imaging apparatus according to an embodiment;

FIGS. 30 and 31 are views illustrating an operation in which overlapping regions are automatically adjusted;

FIG. 49 is a flowchart related to a method for presetting a size of an object in the method for controlling an X-ray imaging apparatus according to an embodiment.

DETAILED DESCRIPTION

Figure 2A:
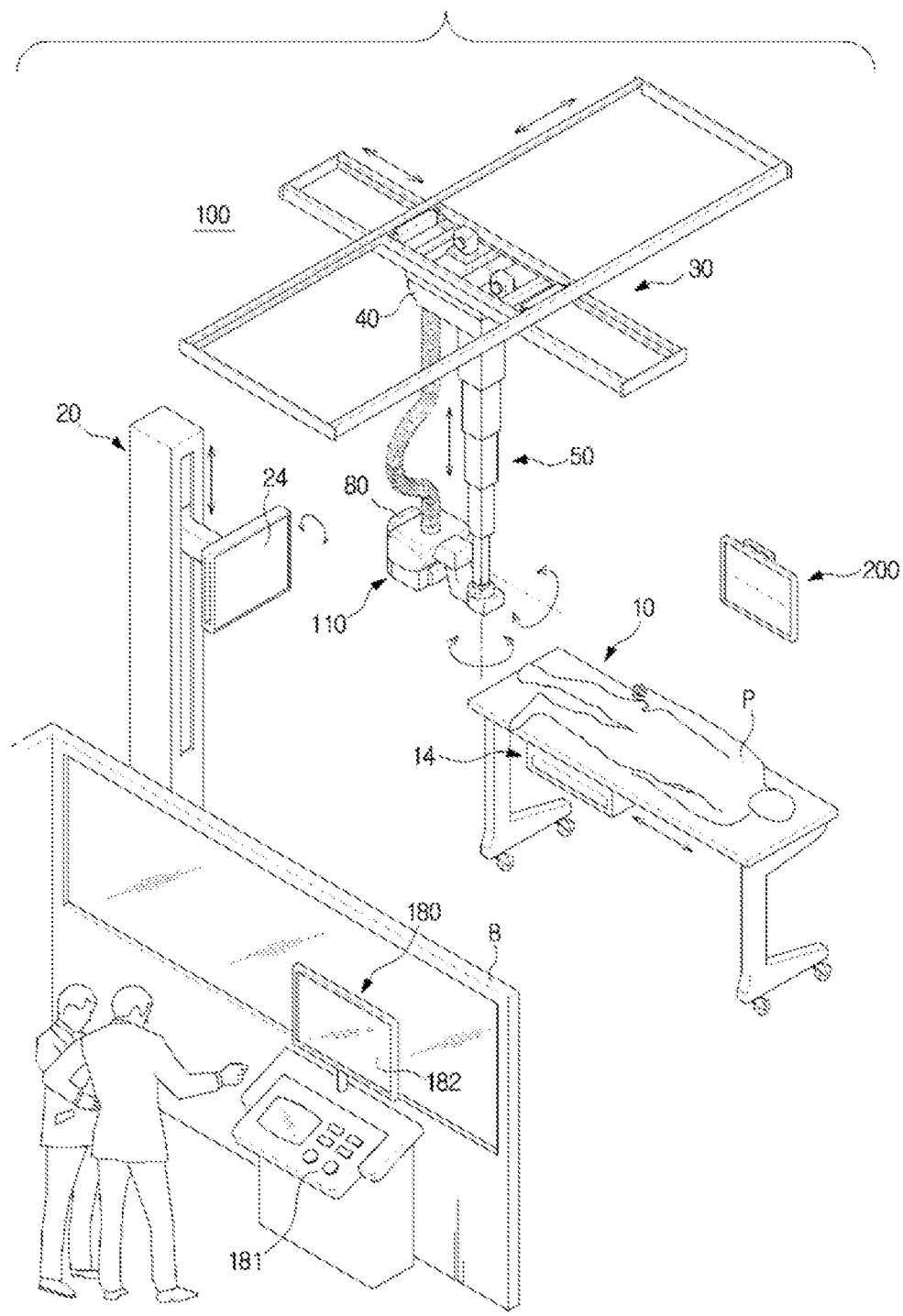
FIG. 2A is an exterior view illustrating a configuration of the X-ray imaging apparatus according to an embodiment.

Hereinafter, embodiments related to an X-ray imaging apparatus and a method for controlling the same according to an aspect will be described in detail with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Figure 2B:
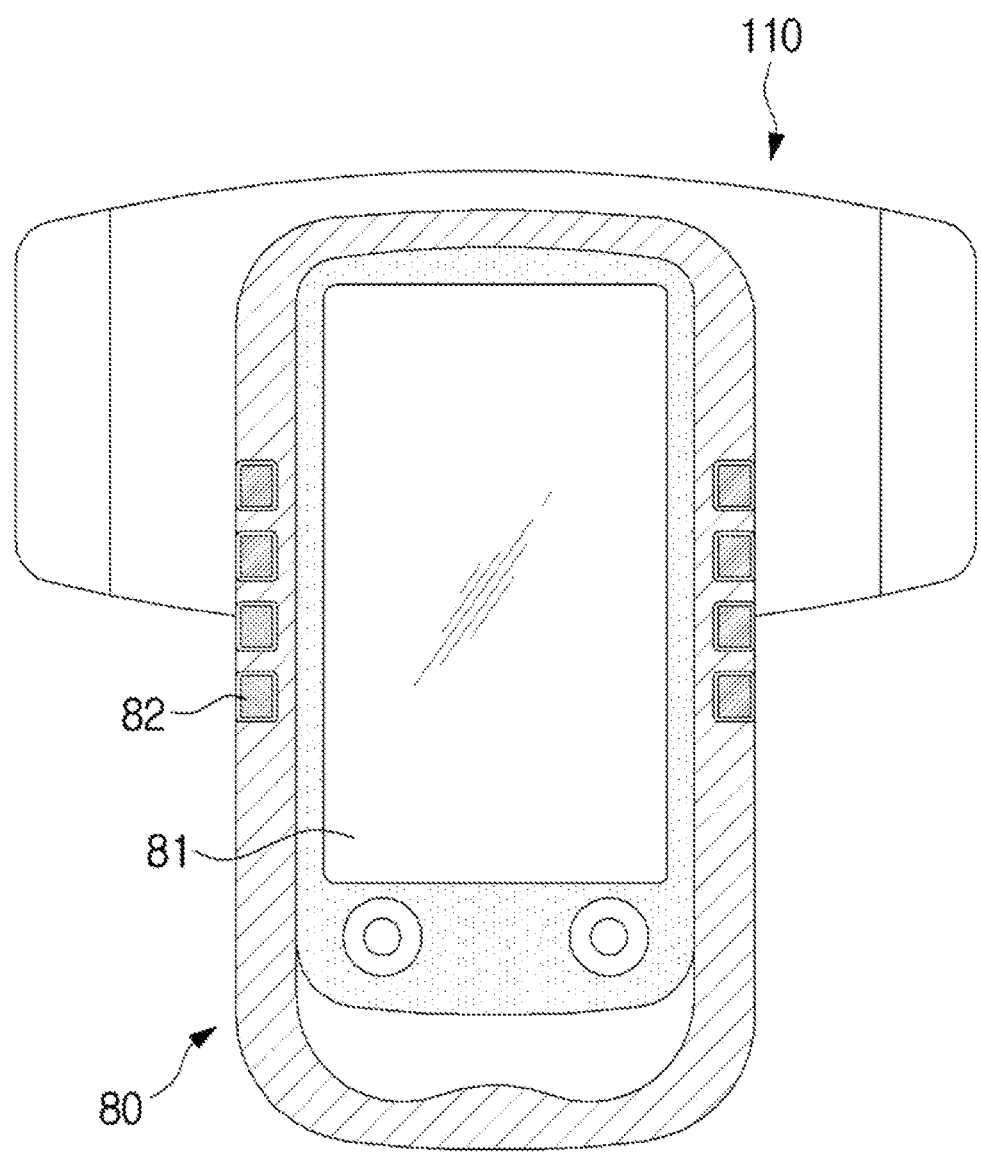
FIG. 2B is an exterior view illustrating a sub-display device mounted on an X-ray source.

FIG. 1 is a control block diagram of an X-ray imaging apparatus according to an embodiment, FIG. 2A is an exterior view illustrating a configuration of the X-ray imaging apparatus according to an embodiment, and FIG. 2B is an exterior view illustrating a sub-display device mounted on an X-ray source. An exterior illustrated in FIG. 2A is an example of the X-ray imaging apparatus and relates to a ceiling type X-ray imaging apparatus in which an X-ray source is connected to a ceiling of an examination room.

Referring to FIG. 1, an X-ray imaging apparatus 100 according to an embodiment includes an X-ray source 110 that generates and radiates X-rays, a display unit 150, e.g., a display, display device, monitor, or a display screen, that displays a screen for setting a size of an object, a screen for setting an imaging protocol, an image captured by a capturing unit 120, e.g., an imaging device, a camera, etc., a screen for setting an X-ray irradiation condition, and the like, an input unit 160 that receives control commands including a command for setting a size of the object, a command for setting the imaging protocol, a command for setting the X-ray irradiation condition, etc. from a user, a storage unit 170 that stores information related to the size of the object, the imaging protocol, and the X-ray irradiation condition, and a control unit 140, i.e., a controller, that controls an overall operation of the X-ray imaging apparatus 100.

In addition, the X-ray imaging apparatus 100 may further include a communication unit 130 that communicates with an external device.

The control unit 140 may control a time point at which X-rays are radiated from the X-ray source 110, an X-ray irradiation condition, etc. according to a command input by the user and may generate a medical image using data received from an X-ray detector 200.

In addition, the control unit 140 may also control a position or an orientation of the X-ray source 110 or mounting units 14 and 24 on which the X-ray detector 200 is mounted according to positions of an imaging protocol and an object P.

The control unit 140 may include a memory in which a program for performing the operations described above and operations, which will be described below, is stored and a processor that executes the stored program. The control unit 140 may include one processor or microprocessor, or a plurality of processors or microprocessors. In the latter case, the plurality of processors or microprocessors may be integrated on one chip or may be physically separated from each other.

When the control unit 140 includes the plurality of processors and a plurality of memories, some of the memories and the processors may be provided at a work station 180, and the remaining memories and processors may be provided in other devices such as a sub-display device (80, see FIG. 2A) or a moving carriage (40, see FIG. 2A). For example, a processor provided in the work station 180 may perform controlling of image processing and the like for generating a medical image, and a processor provided in the sub-display device or the moving carriage may perform controlling related to a movement of the X-ray source 110 or the X-ray detector 200.

The X-ray imaging apparatus 100 may be connected to an external device (e.g., an external server 310, a medical apparatus 320, a portable terminal 330 (such as a smartphone, a tablet personal computer (PC), and a wearable device)) via the communication unit 130 and transmit or receive data therewith.

The communication unit 130 may include one or more elements that enable communicating with an external device. For example, the communication unit 130 may include at least one of a short-distance communication module, a wired communication module, and a wireless communication module. In addition, the communication unit 130 may further include an inner communication module that enables communication between elements of the X-ray imaging apparatus 100.

In addition, the communication unit 130 may receive a control signal from an external device and transmit the received control signal to the control unit 140 such that the control unit 140 may control the X-ray imaging apparatus 100 according to the received control signal.

In addition, the control unit 140 may also control an external device according to the control signal from the control unit 140 by transmitting the control signal to the external device via the communication unit 130. For example, the external device may process data of the external device according to the control signal from the control unit 140 received via the communication unit 130. Since a program capable of controlling the X-ray imaging apparatus 100 may be installed in the external device, the program may include an instruction that executes some or all operations of the control unit 140.

The program may be pre-installed in the portable terminal 330, and the program may also be downloaded and installed by a user of the portable terminal 330 from a server that provides applications. The server that provides applications may include a recording medium in which the corresponding program is stored.

Referring to FIG. 2A, a guide rail 30 may be installed on a ceiling of an examination room in which the X-ray imaging apparatus 100 is disposed, the X-ray source 110 may be connected to the moving carriage 40 moving along the guide rail 30 to move the X-ray source 110 to a position corresponding to the object P, and the moving carriage 40 and the X-ray source 110 may be connected via a post frame 50 to adjust a height of the X-ray source 110.

Since the X-ray source 110 may be moved automatically or manually, the X-ray imaging apparatus 100 may further include a driving unit such as a motor that provides power which moves the X-ray source 110 when the X-ray source 110 automatically moves.

The work station 180 may be provided in a space separated from a space in which the X-ray source 110 is disposed by a shielding curtain B. The work station 180 may include an input unit 181 that receives a command from the user and a display unit 182 that displays information.

The input unit 181 may receive a command for controlling an imaging protocol, an X-ray irradiation condition, a time point at which X-rays are radiated, a position of the X-ray source 110, and the like. The input unit 181 may include a keyboard, a mouse, a touch screen, a voice recognizer, and the like.

The display unit 182 may display a screen for guiding an input by the user, an X-ray image, a screen showing a state of the X-ray imaging apparatus 100, etc.

Meanwhile, the display unit 150 and the input unit 160 described with reference to FIG. 1 may be respectively implemented as the display unit 182 and the input unit 181 provided in the work station 180, may also be respectively implemented as a sub-display unit 81 and a sub-input unit 82 provided in the sub-display device 80, and may also be implemented as a display unit and an input unit provided in a mobile device such as a tablet PC and a smartphone.

The X-ray detector 200 may be implemented with a fixed type X-ray detector fixed to a stand 20 or a table 10, may be detachably mounted on the mounting units 14 and 24, and may also be implemented with a portable X-ray detector which is usable at any position. The portable X-ray detector may be implemented as a wired type or a wireless type according to a way of transmitting data and a way of supplying power.

Since the X-ray detector 200 may also move automatically or manually, the X-ray imaging apparatus 100 may further include a driving unit such as a motor that provides power which moves the mounting units 14 and 24 when the X-ray detector 200 moves automatically.

The X-ray detector 200 may either be included or not included as an element of the X-ray imaging apparatus 100. In the latter case, the X-ray detector 200 may be registered in the X-ray imaging apparatus 100 by the user. In addition, in both cases, the X-ray detector 200 may be connected to the control unit 140 via the communication unit 130 to receive a control signal or transmit image data.

The sub-display device 80 that provides the user with information and receives a command from the user may be provided at one side of the X-ray source 110, and some or all of the functions performed by the input unit 181 and the display unit 182 of the work station 180 may be performed by the sub-display device 80.

When all or some of the elements of the control unit 140 and the communication unit 130 are provided to be separate from the work station 180, the elements may be included in the sub-display device 80 provided at the X-ray source 110.

The user may input various types of information or commands related to X-ray imaging by manipulating the sub-input unit 82 illustrated in FIG. 2B or touching the sub-display unit 81 illustrated in FIG. 2B.

For example, the user may input a position to which the X-ray source 110 will be moved through the sub-input unit 82 or the sub-display unit 81.

Although FIG. 2A illustrates a fixed type X-ray imaging apparatus connected to the ceiling of the examination room, the X-ray imaging apparatus 100 may include X-ray imaging apparatuses with various structures such as a C-arm type X-ray imaging apparatus and a mobile X-ray imaging apparatus within the scope that is self-evident to those of ordinary skill in the art.

Meanwhile, the X-ray source 110 may include an X-ray tube that generates X-rays, a collimator that adjusts a region to be irradiated with X-rays generated by the X-ray tube, and the capturing unit 120 that captures a camera image. Hereinafter, these will be described in detail with reference to the drawings.

Figure 3A:
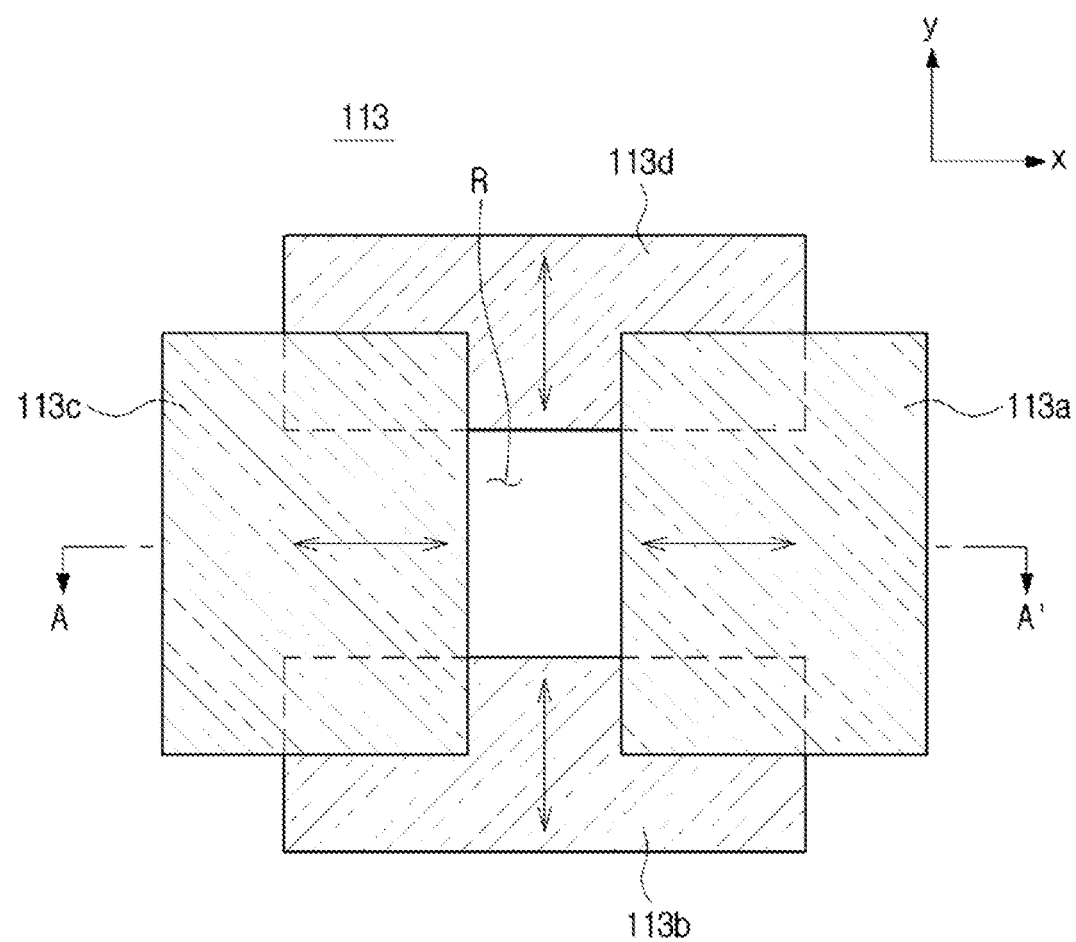
FIG. 3A is a view illustrating a configuration of a collimator.
Figure 3B:
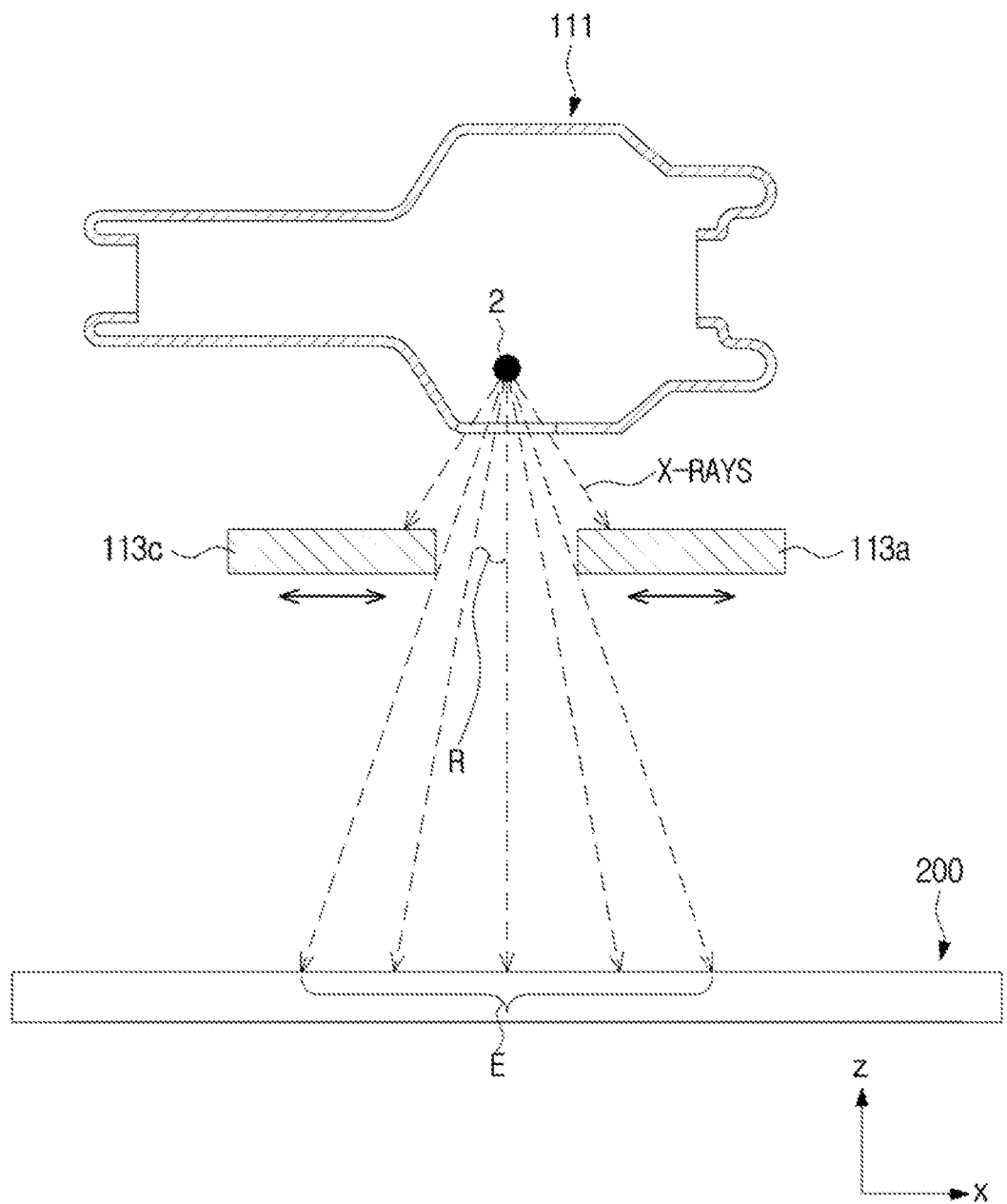
FIG. 3B is a lateral cross-sectional view of a blade taken along line A-A' in FIG. 3A.

FIG. 3A is a view illustrating a configuration of a collimator, and FIG. 3B is a lateral cross-sectional view of a blade taken along line A-A' in FIG. 3A.

Referring to FIG. 3A, a collimator 113 may include one or more movable blades 113a, 113b, 113c, and 113d, and the one or more blades may absorb X-rays by being formed of a material having a high bandgap. An irradiation range of X-rays may be adjusted as the one or more blades move, and the collimator 113 may further include a motor that provides power to each of the one or more blades.

The control unit 140 calculates a movement amount of each of the one or more blades corresponding to a set X-ray irradiation region and transmits a control signal for moving the one or more blades by the calculated movement amount to the collimator 113.

For example, the collimator 113 may include the four blades 113a, 113b, 113c, and 113d each having a quadrilateral shape. The first blade 113a and the third blade 113c are movable in both directions along an x-axis, and the second blade 113b and the fourth blade 113d are movable in both directions along a y-axis.

In addition, each of the four blades 113a, 113b, 113c, and 113d may move separately, or the first blade 113a and the third blade 113c may move together as a set and the second blade 113b and the fourth blade 113d may move together as a set.

X-rays may be radiated through a slot R formed by the four blades, and collimation may be performed by passing the X-rays through the slot R. Consequently, in this embodiment, the slot R is referred to as a collimation region, and an X-ray irradiation region signifies a region in which X-rays that have passed through the collimation region R are incident on an object 1 or the X-ray detector 200.

Referring to FIG. 3B, the collimator 113 is disposed in front of an X-ray tube 111. Here, a direction toward a front of the X-ray tube 111 signifies a direction in which X-rays are radiated. An X-ray irradiation region E of X-rays radiated from a focal point 2 of the X-ray tube 111 is limited by the collimator 113, and scattering of the X-rays is reduced.

Among the X-rays radiated from the X-ray tube 111, X-rays incident on the blades 113a, 113b, 113c, and 113d are absorbed into the blades, and X-rays that have passed through the collimation region R are incident on the X-ray detector 200. Here, a description will assume that an object does not exist.

When X-rays scatter in the form of cone beams, the X-ray irradiation region E is larger than the collimation region R. A desired range of the X-ray irradiation region E may be irradiated with X-rays by the control unit 140 by adjusting the collimation region R based on a relation between the two regions.

Although the collimator 113 has been described as having four blades in a quadrilateral shape in the example above, this is merely an example that is applicable to the X-ray imaging apparatus 100, and the number or shape of blades included in the collimator 113 is not limited thereto.

Figure 4:
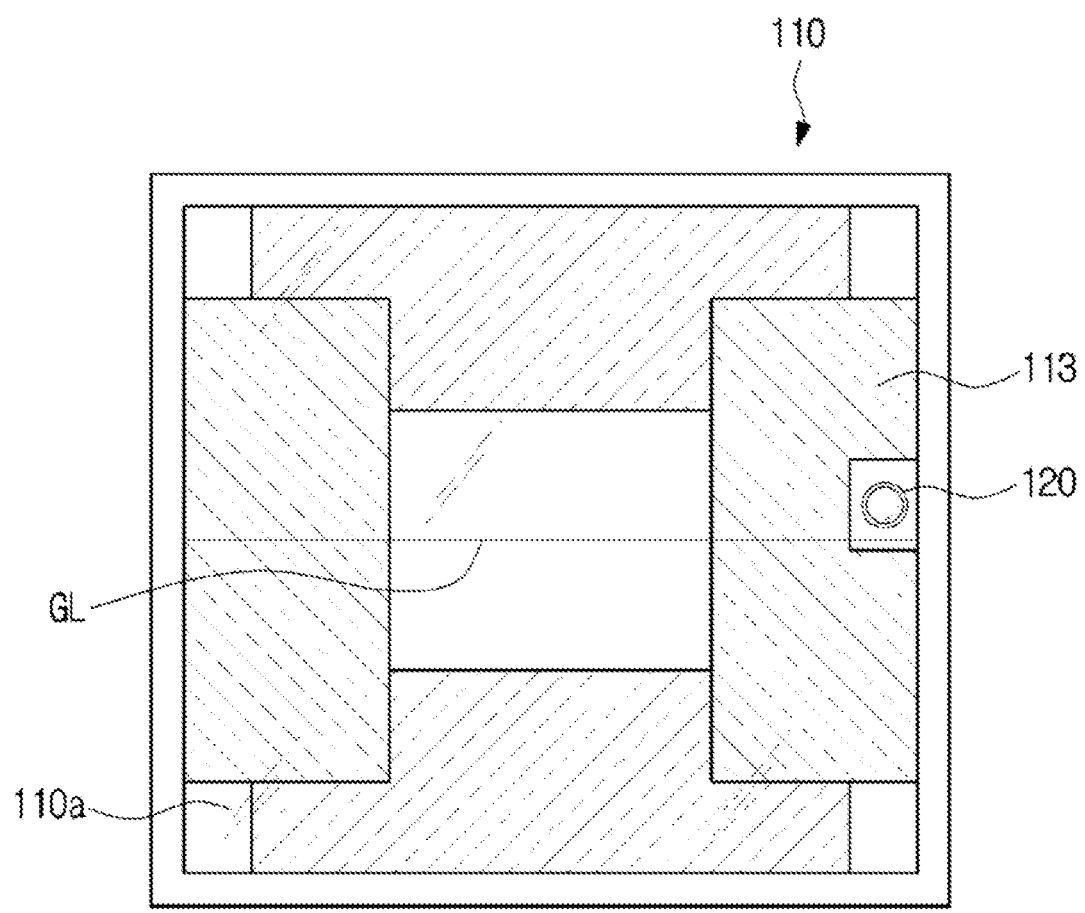
FIG. 4 shows an X-ray source viewed from the front.

FIG. 4 shows an X-ray source viewed from the front.

Referring to FIG. 4, the collimator 113 may be disposed in front of the X-ray source 110, and the capturing unit 120 may be embedded in a region adjacent to the collimator 113.

The capturing unit 120 may capture a video by being be implemented as a camera such as a charge-coupled device (CCD) camera and a complementary metal oxide silicon (CMOS) camera. Alternatively, the capturing unit 120 may also capture still images at short intervals.

While the X-ray source 110 captures an X-ray image of an object, the capturing unit 120 captures a real image of the object, e.g., a target. In an embodiment to be described below, an image captured by the X-ray source 110 will be referred to as an X-ray image, and an image captured by the capturing unit 120 will be referred to as a camera image. The camera image may either include or not include an object. That is, the camera image may be captured while the object 1 is disposed in front of the X-ray detector 200, and the camera image may also be captured while the object 1 does not exist.

The capturing unit 120 may be disposed at a position at which a portion of an object to be imaged by X-rays may be captured. For example, the capturing unit 120 may be mounted on the X-ray source 110 in a direction that is the same as a direction in which X-rays are radiated from the X-ray source 110. When the capturing unit 120 is mounted on the X-ray source 110, the user may more easily set settings related to an X-ray image while looking at a camera image since an offset between a region shown in the X-ray image and a region shown in the camera image is reduced. A position on which the capturing unit 120 is mounted may be suitably determined within a range that minimizes the offset between the region shown in the X-ray image and the region shown in the camera image and that does not affect X-ray imaging.

Since a housing 110a may be formed in front of the collimator 113, the housing 110a may be formed with a material such as a transparent resin or glass to minimize its influence on X-rays radiated from the X-ray tube 111.

In addition, a guideline GL in a cross shape may be displayed on the housing formed in front of the collimator 113. When the X-ray irradiation region E is irradiated with visible rays by a collimator lamp embedded in the X-ray source 110, a shadow of the guideline GL may be displayed at the center of the X-ray irradiation region E and the user may intuitively recognize a position of the X-ray irradiation region E by looking at the shadow of the guideline GL.

The capturing unit 120 may be mounted on an inner portion of the housing 110a as illustrated in FIG. 4. Alternatively, the capturing unit 120 may also be mounted on an outer portion of the housing 110a. Here, the capturing unit 120 may be mounted on a bezel provided at a circumference of the housing 110a. However, since an embodiment of the X-ray imaging apparatus 100 is not limited thereto, the capturing unit 120 may be mounted on any position so long as an image of an object can be captured at the position.

In addition, the capturing unit 120 may also be implemented as a stereo camera. In this case, cameras may be disposed at both left and right sides in front of the X-ray source 110. When the capturing unit 120 is implemented as a stereo camera, information on a depth of a camera image may be acquired and accuracy in image recognition and reliability of various types of information calculated based on the camera image may be improved using the depth information.

Figure 5A:
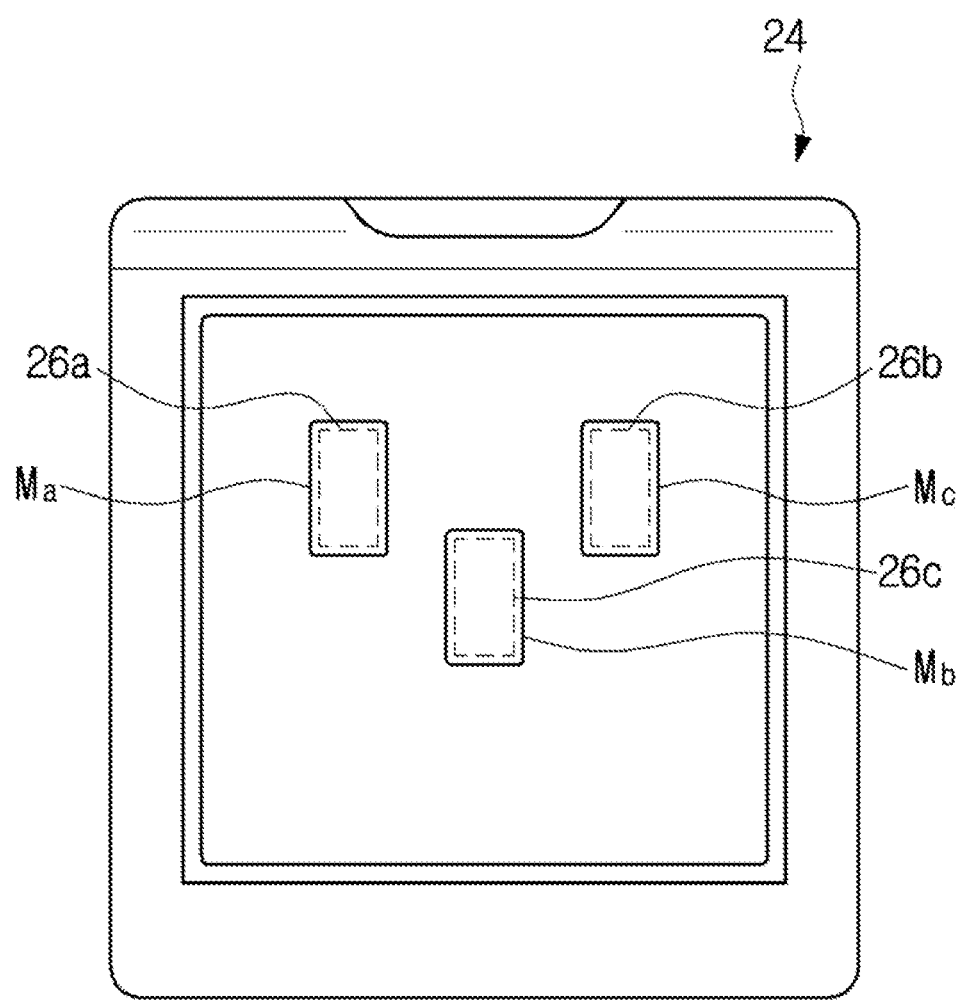
FIGS. 5A and 5B are each a view illustrating an example of an automatic exposure control (AEC) sensor that may be used in the X-ray imaging apparatus according to an embodiment.
Figure 5B:
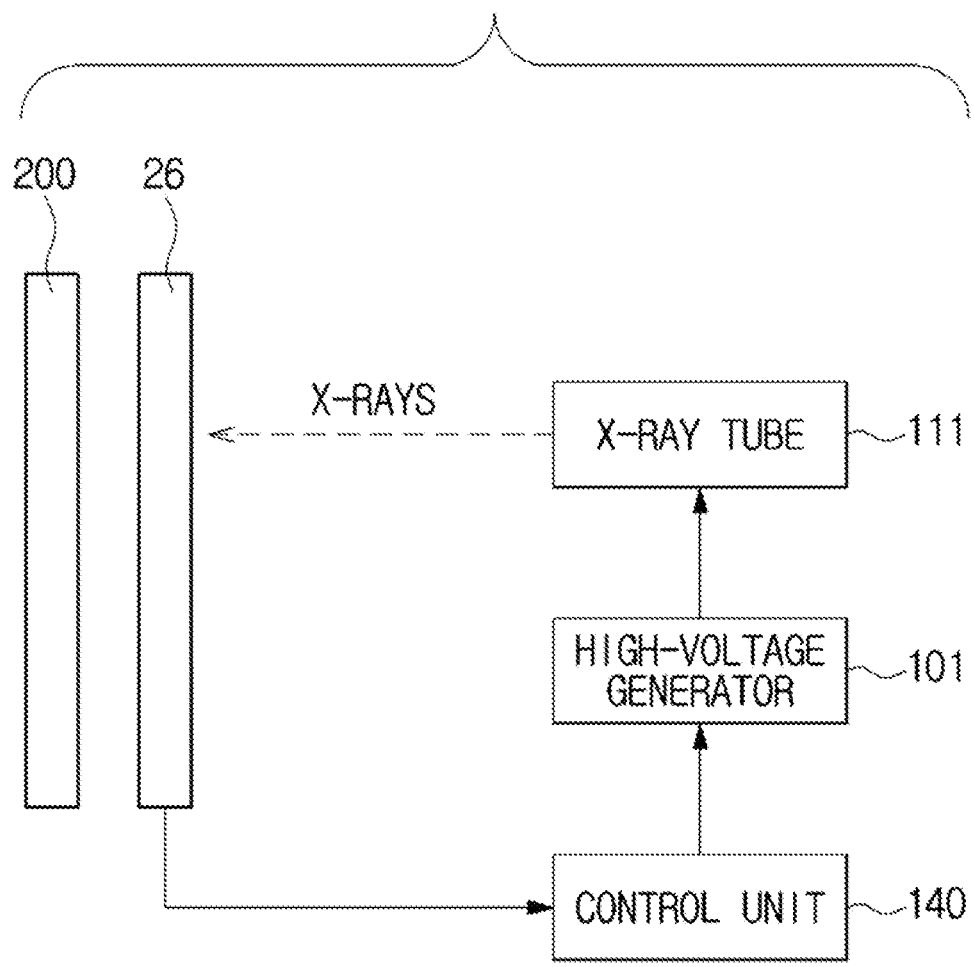

FIGS. 5A and 5B are views each illustrating an example of an automatic exposure control (AEC) sensor that may be used in the X-ray imaging apparatus according to an embodiment.

To prevent an object from being excessively irradiated with X-rays, the X-ray imaging apparatus 100 may perform AEC. For this, an AEC sensor module 26 that detects a dose of X-rays may be provided in the mounting unit 24 as illustrated in FIG. 5A. Although the AEC sensor module 26 is described using the mounting unit 24 of the stand 20 in this example, an AEC sensor module may also be provided at the mounting unit 14 of the table 10.

FIG. 5A shows the mounting unit 24 viewed from the front. The AEC sensor module 26 may be provided inside the mounting unit 24 and may include a plurality of AEC sensors 26a, 26b, and 26c that independently detect a dose of X-rays. For example, each of the AEC sensors may be implemented as an ionization chamber.

The most accurate AEC is possible when an AEC sensor is disposed at the center of an X-ray imaging portion. Markers Ma, Mb, and Mc that respectively show positions of the plurality of AEC sensors 26a, 26b, and 26c may be provided at a surface of the mounting unit 24 to position the center of the X-ray imaging portion at a position corresponding to the AEC sensor or select an AEC sensor disposed at the center of the X-ray imaging portion.

Although a total of three AEC sensors, two at an upper side and one at a lower side, are illustrated as being provided in FIG. 5A, this is merely an example. Less than or more than three AEC sensors may also be provided, and the AEC sensors may also be arranged in a different way.

Referring to FIG. 5B, the AEC sensor module 26 may also be disposed in front of the X-ray detector 200. A direction toward the front of the X-ray detector 200 signifies a direction in which X-rays are incident. FIG. 5B shows the AEC sensor module 26 disposed in front of the X-ray detector 200 viewed from the side.

A current may be generated when X-rays are incident on an AEC sensor, and the AEC sensor may transmit a signal corresponding to the generated current to the control unit 140. The signal transmitted to the control unit 140 may be an amplified and digitized signal.

Based on the transmitted signal, the control unit 140 determines whether a dose of X-rays currently incident exceeds a critical dose. When the dose of the X-rays exceeds the critical dose, a cut-off signal may be transmitted to a high-voltage generator 101 that supplies a high voltage to the X-ray tube 111 to stop generation of the X-rays.

Meanwhile, a grid that prevents X-rays from scattering may also be disposed in front of the AEC sensor module 26. Some of the X-rays radiated from the X-ray source 110 may deviate from their original path and scatter by colliding against dust particles in the air or substances forming an object before reaching the X-ray detector 200. When the scattered X-rays are incident on the X-ray detector 200, the scattered X-rays have a negative influence on the quality of an X-ray image such as degrading the contrast of an X-ray image.

The grid has a structure in which shielding substances such as lead (Pb) that absorb X-rays are arranged. Among radiated X-rays, X-rays advancing in their original direction, i.e., X-rays moving forward, pass through portions between the shielding substances and are incident on the X-ray detector 200, and scattered X-rays collide with the shielding substances and are absorbed into the shielding substances.

The shielding substances may be arranged in a linear structure and also in a cross-like structure. In addition, the shielding substances may be tilted in a direction similar to that in which the X-rays are radiated and may be densely arranged or arranged in parallel.

Although not illustrated in the drawings, a driving unit that includes a motor which may mechanically move the grid may be disposed inside the mounting unit 24. Consequently, an angle or a central position of the grid may be adjusted by transmitting a control signal to the driving unit from the outside.

Meanwhile, although the AEC sensor module 26 has been described in the example as being provided at the mounting unit 24, the AEC sensor module 26 may also be integrally provided with the X-ray detector 200.

Figure 6:
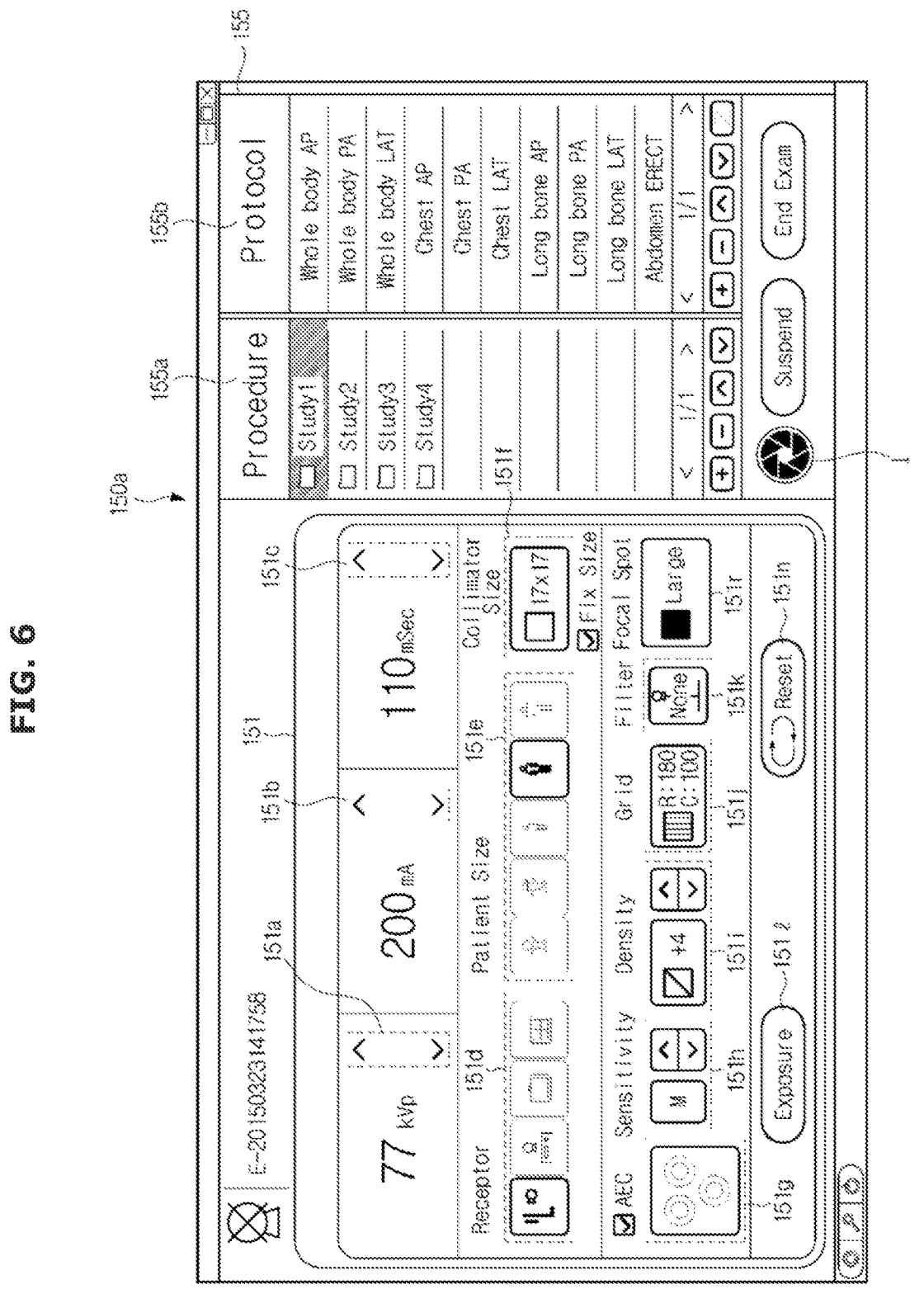

FIGS. 6 and 7 are each a view illustrating an example of a screen displayed on a display unit of the X-ray imaging apparatus according to an embodiment.

As illustrated in FIG. 6, a settings window 151 for setting an x-ay irradiation condition and a work list 155 may be displayed on a screen 150a of the display unit 150.

The work list 155 may include a study list 155a from which a study may be selected and a protocol list 155b from which an imaging protocol may be selected. A study may refer to a set of X-ray images related to each other. When any one study is selected from the study list 155a, the protocol list 155b from which an imaging protocol to be applied to the selected study may be selected is displayed.

An X-ray imaging region may change for each imaging protocol, and a suitable X-ray irradiation condition may change for each X-ray imaging region. The imaging protocol may be determined according to an X-ray imaging portion, a posture of an object, and the like. For example, imaging protocols may include whole body anterior-posterior (AP), whole body posterior-anterior (PA), and whole body lateral (LAT), may also include chest AP, chest PA, and chest LAT, and may also include long bone AP, long bone PA and long bone LAT for long bones such as a leg bone. In addition, the imaging protocols may also include abdomen erect.

A graphic user interface (GUI) in which an X-ray irradiation condition may be set may be displayed on the settings window 151. The GUI may include a plurality of graphical objects which may be used to set various X-ray irradiation conditions. In this embodiment, objects such as buttons and icons displayed on the display unit 150 to be used in providing information or receiving a control command from the user may all be referred to as graphical objects.

Since the graphical objects displayed on the settings window 151 are used to receive a command for setting an X-ray irradiation condition from the user, the graphical objects may be implemented as buttons respectively corresponding to various X-ray irradiation conditions.

For example, a tube voltage setting button 151a for receiving a tube voltage setting, a tube current setting button 151b for receiving a tube current setting, and an exposure time setting button 151c for receiving an X-ray exposure time setting may be displayed. The user may select each of the buttons to set an X-ray irradiation condition to have a desired value. The buttons may be selected by clicking or touching depending on a type of the input unit 160.

According to an embodiment, the tube voltage setting button 151a may separately include a button for increasing a tube voltage and a button for decreasing the tube voltage, the tube current setting button 151b may separately include a button for increasing a tube current and a button for decreasing the tube current, and the exposure time setting button 151c may separately include a button for increasing an exposure time and a button for decreasing the exposure time.

In addition, a capture position setting button 151d for receiving a setting related to whether X-ray imaging will be performed at the stand 20 or at the table 10, an object size selection button 151e for receiving a selection related to a size of a patient, a collimator setting button 151f for receiving a setting related to a size of the collimator 113, an AEC selection button 151g for receiving a selection related to an AEC sensor, a sensitivity setting button 151h for receiving a setting related to sensitivity, a button 151i for receiving a setting related to density, a grid selection button 151j for receiving a selection related to the grid, a filter selection button 151k for receiving a selection related to a filter, a focal point selection button 151r for receiving a selection related to a size of a focal point, etc. may be further displayed.

The buttons may be implemented as shapes formed of pictures, letters, symbols, etc. The user may select any one shape by moving a cursor and clicking the corresponding shape or touching and manipulating the shape. Accordingly, a setting corresponding to the selected shape may be changed.

Meanwhile, when a selection related to a size of a patient is input, an X-ray irradiation condition mapped as a default for the corresponding size may be set. For this, the storage unit 170 may store a database in which an X-ray irradiation condition for each of a plurality of sizes of a patient is mapped.

When the user selects a size of a patient, X-ray irradiation conditions such as a tube voltage, a tube current, and an exposure time mapped as a default for the corresponding size are displayed in the settings window 151. The mapped X-ray irradiation conditions may be applied without change, or the user may select a button corresponding to each of the X-ray irradiation conditions and set each of the X-ray irradiation conditions again according to the method described above. Here, the user may set each of the X-ray irradiation conditions again with reference to default X-ray irradiation conditions displayed in the settings window 151.

In addition, an X-ray imaging region may change for each imaging protocol, and a suitable X-ray irradiation condition may change for each X-ray imaging region. Consequently, an X-ray irradiation condition may be set differently according to an imaging protocol selected from the work list 155 and a size of an object selected from the settings window 151.

The types and arrangements of the graphical objects displayed in the settings window 151 described above are all illustrative. Some of the above may be omitted according to a designer's choice, a graphical object other than the above for changing a setting may be further provided, and the above may be provided in arrangements different from those in the example described above.

When the setting of X-ray irradiation conditions is completed, the user may select an exposure button 151*l* to perform X-ray imaging and may select a reset button 151*m* when attempting to initialize settings.

Meanwhile, to obtain information required for performing X-ray imaging, the capturing unit 120 may capture a camera image while the X-ray source 110 is facing the X-ray detector 200. In this case, the X-ray detector 200 or the mounting units 14 and 24 on which the X-ray detector 200 is mounted may be covered by the object 1 and may not be shown in the camera image. Conversely, when a camera image is captured while the object 1 is not disposed in front of the X-ray detector 200, the X-ray detector 200 or the mounting units 14 and 24 on which the X-ray detector 200 is mounted may be shown in the camera image. A captured camera image 152 may be displayed at one side of the settings window 151 as illustrated in FIG. 7.

The work list 155 illustrated in FIG. 6 and the camera image 152 illustrated in FIG. 7 may be switched with each other. The work list 155 may be switched to the camera image 152 when a camera image button I is selected while the work list 155 is displayed, and the camera image 152 may be switched to the work list 155 when a close button 152*b* is selected while the camera image 152 is displayed. Alternatively, when the selected imaging protocol needs stitching imaging, the work list 155 may be switched to the camera image 152 automatically and then screens regarding stitching imaging described below may be displayed.

Referring to FIG. 7, an X-ray irradiation window B1 may be displayed by being overlapped on the X-ray detector 200 or the mounting unit 24 shown in the camera image 152. In this example, the X-ray detector 200 is mounted in the mounting unit 24, and the mounting unit 24 is displayed in the camera image.

The X-ray irradiation window B1 is a tool for showing a region at which X-rays radiated from the X-ray source 110 reach the X-ray detector 200, i.e. the X-ray irradiation region E. The control unit 140 may calculate the X-ray irradiation region E according to an algorithm, which will be described below, and display the X-ray irradiation window B1 that shows a size and a position of the calculated X-ray irradiation region E in the camera image 152 to provide the user with information on the size and the position of the calculated X-ray irradiation region E. Here, a size and a position of the X-ray irradiation window B1 is relative to the mounting unit 24 shown in the camera image 152.

The user may adjust the position, the size, or a form of the X-ray irradiation window B1 displayed on the display unit 150 by inputting a predetermined operation command through the input unit 160, and the control unit 140 may control the collimator 113 according to the input operation command to adjust the X-ray irradiation region E.

The X-ray irradiation window B1 displayed on the display unit 150 and the actual X-ray irradiation region E may be different from each other due to various errors of an apparatus. That is, the X-ray irradiation window B1 may not accurately reflect the position or the size of the actual X-ray irradiation region E in some cases. Consequently, the X-ray imaging apparatus 100 may perform a procedure for verifying whether the X-ray irradiation window B1 illustrated in FIG. 7 accurately reflects the actual X-ray irradiation region E.

First, a method for displaying the X-ray irradiation window B1 on the display unit 150 will be described.

The control unit 140 may display the X-ray irradiation window B1 on the display unit 150 using pre-stored coordinate information of the X-ray imaging apparatus 100. The control unit 140 may include pre-stored pieces of information on a distance between the X-ray source 110 and the X-ray detector 200, a form and an area of the slot R formed by the collimator 113, a distance from the X-ray tube 111 to the slot R of the collimator 113, etc., or may calculate the above pieces of information from pre-stored information.

The control unit 140 may calculate three-dimensional coordinates of the X-ray irradiation region E formed at a surface of the mounting unit 24 using the above pieces of information. The three-dimensional coordinates of the X-ray irradiation region E calculated by the control unit 140 correspond to coordinates on a global coordinate system of a space in which the X-ray imaging apparatus 100 is disposed. The coordinate information of the X-ray irradiation region E calculated by the control unit 140 may include at least coordinates of vertices of the X-ray irradiation region E.

The X-ray irradiation window B1 showing the X-ray irradiation region is displayed by being overlapped on the camera image 152. Since the X-ray irradiation window B1 displayed by being overlapped on the camera image 152 is based on a two-dimensional coordinate system, the control unit 140 converts the calculated information on three-dimensional coordinates of the X-ray irradiation region E into coordinates based on a two-dimensional image coordinate system.

In addition, the camera image 152 illustrated in FIG. 7 is an image acquired by the capturing unit 120, and a coordinate system of the capturing unit 120 is different from the global coordinate system. Thus, to covert the information on three-dimensional coordinates of the X-ray irradiation region E into coordinates based on the two-dimensional image coordinate system as described above, the global coordinate system should be converted into a camera coordinate system. That is, the global coordinate system should be converted into the camera coordinate system, and the information on three-dimensional coordinates converted into coordinates based on the camera coordinate system should be converted into coordinates based on the two-dimensional image coordinate system.

An equation for converting coordinates (X, Y, and Z) based on the global coordinate system into coordinates (x, y)

based on the two-dimensional coordinate system may be expressed as Equation 1. The control unit 140 may convert three-dimensional coordinates of the X-ray irradiation region formed at the X-ray detector 200 into two-dimensional coordinates of the X-ray irradiation window B1 to be displayed on the display unit 150 using the relation between the global coordinate system and the two-dimensional coordinate system expressed by Equation 1 below. The control unit 140 may use the two-dimensional coordinates converted as above to display the X-ray irradiation window B1 by overlapping the X-ray irradiation window B1 on the camera image displayed on the display unit 150.

$$\begin{bmatrix} x \\ y \\ 1 \end{bmatrix} = \begin{bmatrix} f_x & 0 & c_x \\ 0 & f_y & c_y \\ 0 & 0 & 1 \end{bmatrix} \cdot$$

$$\begin{bmatrix} \cos B \cos C & -\cos B \sin C & \sin B & t_1 \\ \sin A \sin B \cos C + \cos A \sin C & -\sin A \sin B \sin C + \cos A \cos C & -\sin A \cos B & t_2 \\ -\cos A \sin B \cos C + \sin A \sin C & \cos A \sin B \sin C + \sin A \cos C & \cos B \cos B & t_3 \end{bmatrix} \cdot \begin{bmatrix} X \\ Y \\ Z \\ 1 \end{bmatrix}$$

⟨Equation 1⟩

In Equation 1, x and y represent coordinates of a two-dimensional image sensor, i.e., coordinates of an image coordinate system, and X, Y, and Z represent coordinates of the global coordinate system.

In Equation 1 above, a first matrix at the right side includes inner parameters of the capturing unit 120 such as a focal length and a principal point of the capturing unit 120 as its elements. In Equation 1, fx and fy represent the focal length of the capturing unit 120, and cx and cy represent the principal point of the capturing unit 120.

In Equation 1, a second matrix at the right side is a matrix to allow the global coordinate system to match the camera coordinate system and includes outer parameters of the capturing unit 120 such as a direction in which the capturing unit 120 is installed as its elements.

In Equation 1, A represents a rotational angle (a roll) having a z-axis of the camera coordinate system as a rotational axis, B represents a rotational angle (a pitch) having an x-axis of the camera coordinate system as a rotational axis, and C represents a rotational angle (yaw) having a y-axis of the camera coordinate system as a rotational axis. In addition, $t_1$, $t_2$, and $t_3$ each represent a translation movement distance between the camera coordinate system and the global coordinate system.

Figure 8A:
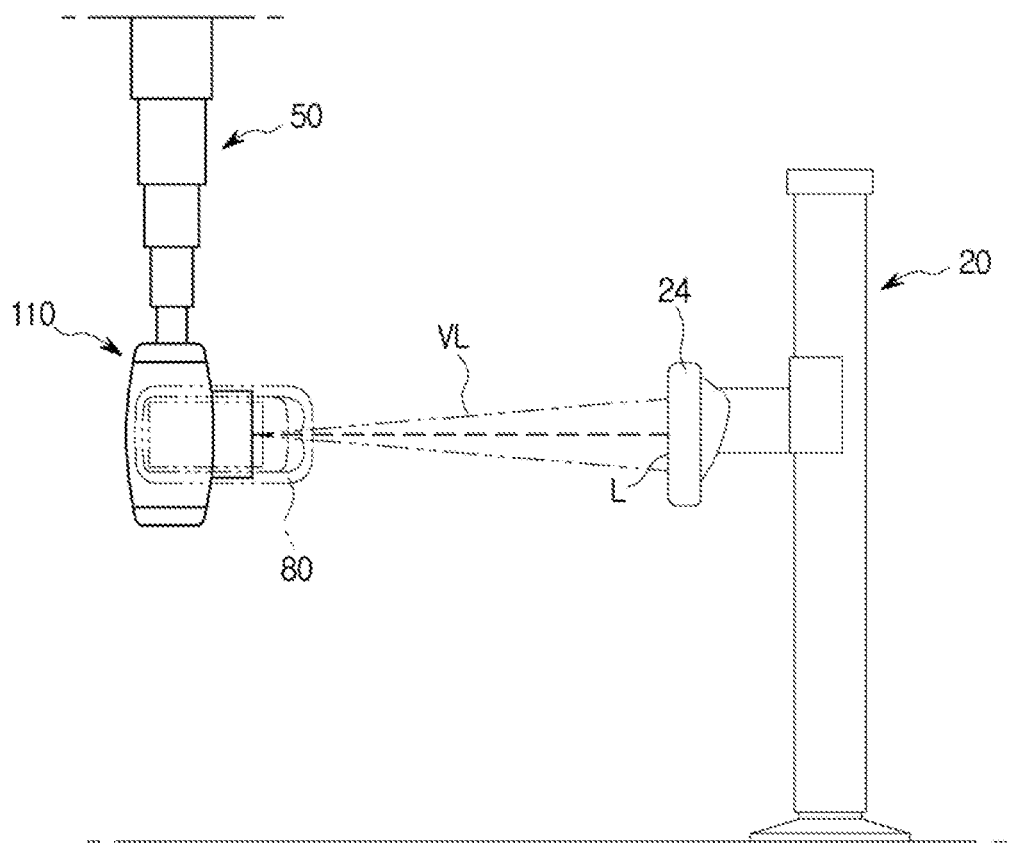
FIG. 8A is a conceptual view illustrating light showing an X-ray irradiation region being radiated from the X-ray source.
Figure 8B:
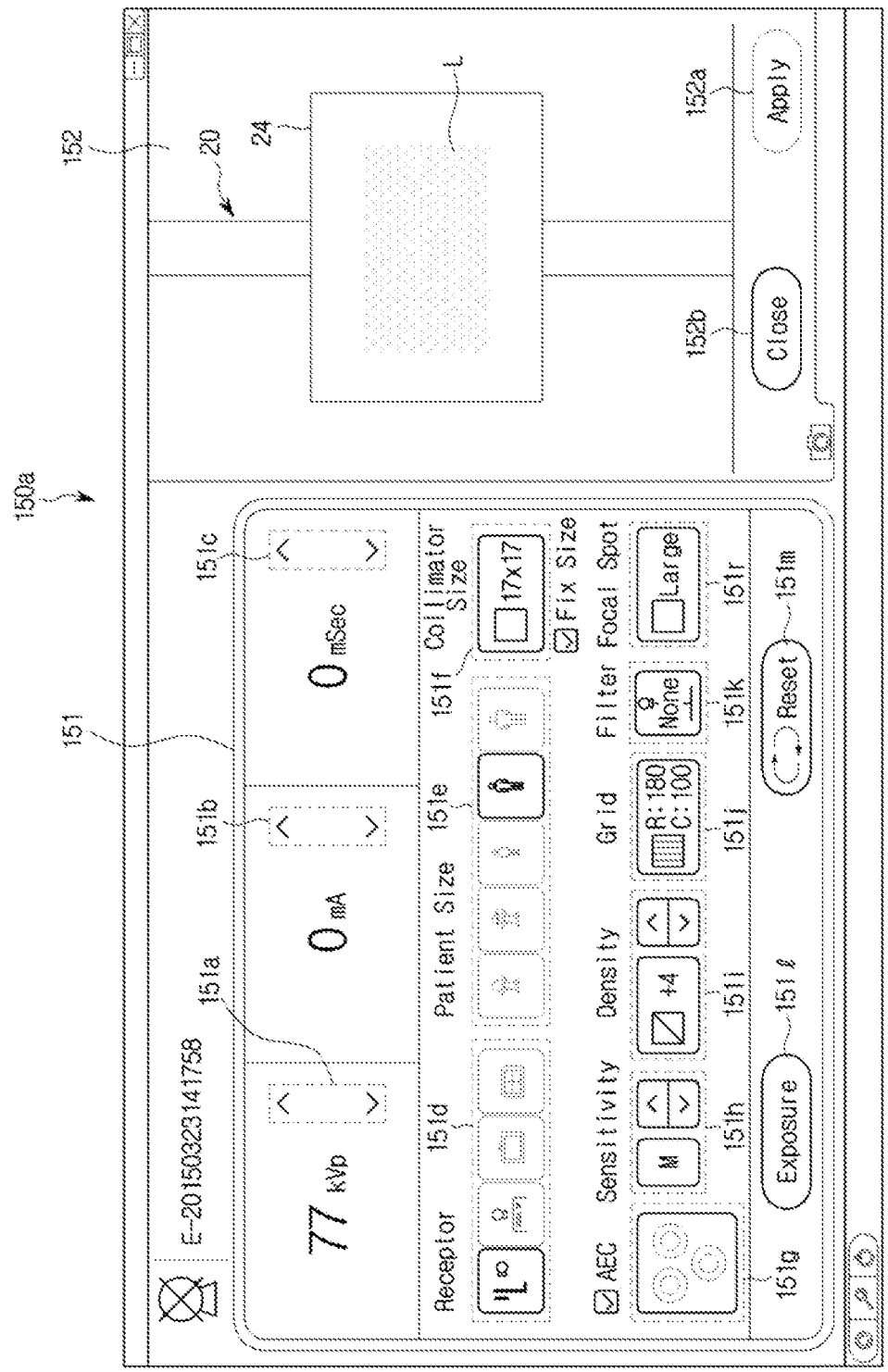
FIG. 8B is a view illustrating an example in which a light irradiation region is included in a camera image displayed on the display unit.
Figure 9:
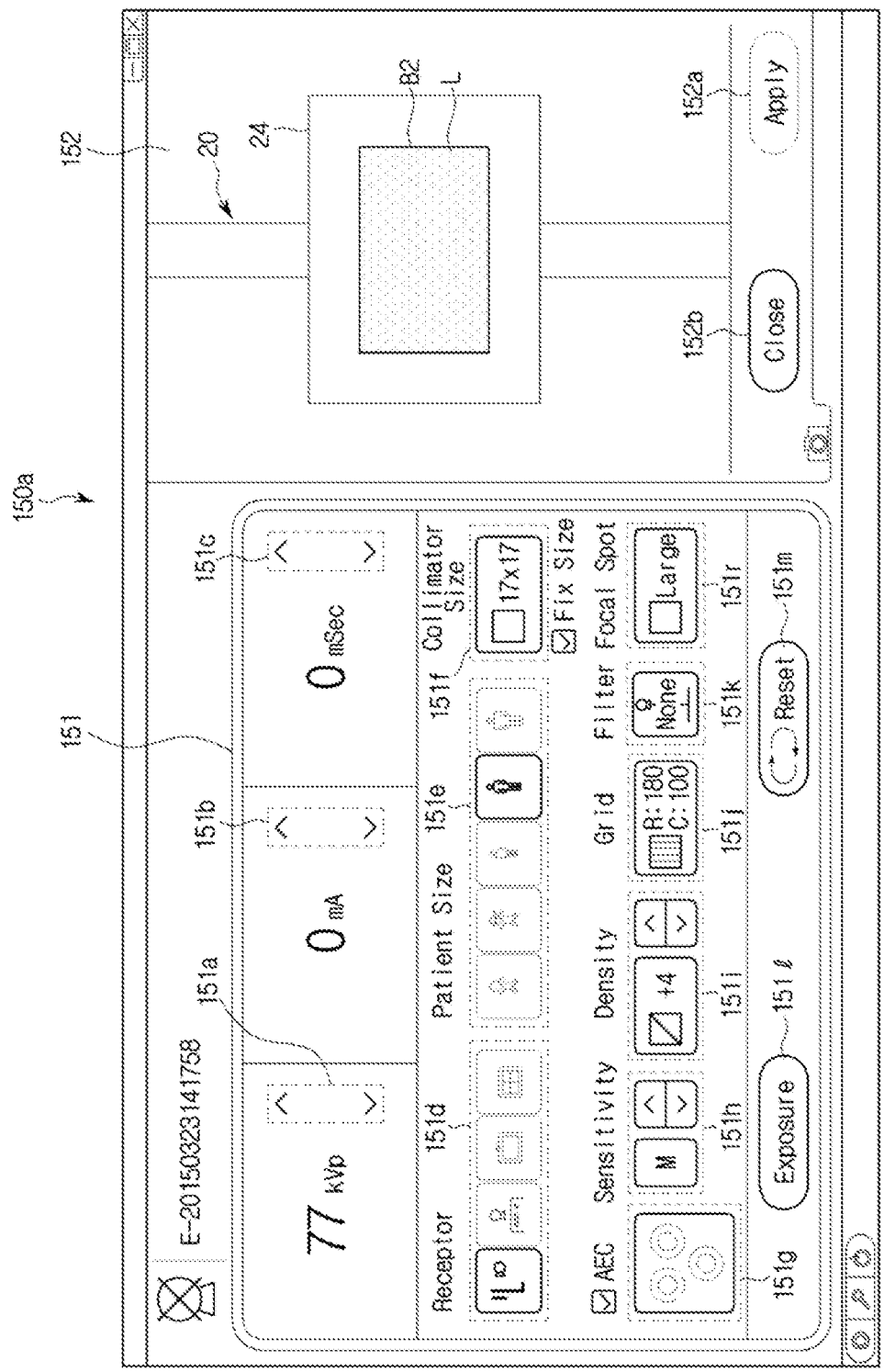
FIG. 9 is a view illustrating an example of displaying an X-ray irradiation window based on the light irradiation region.
Figure 10:
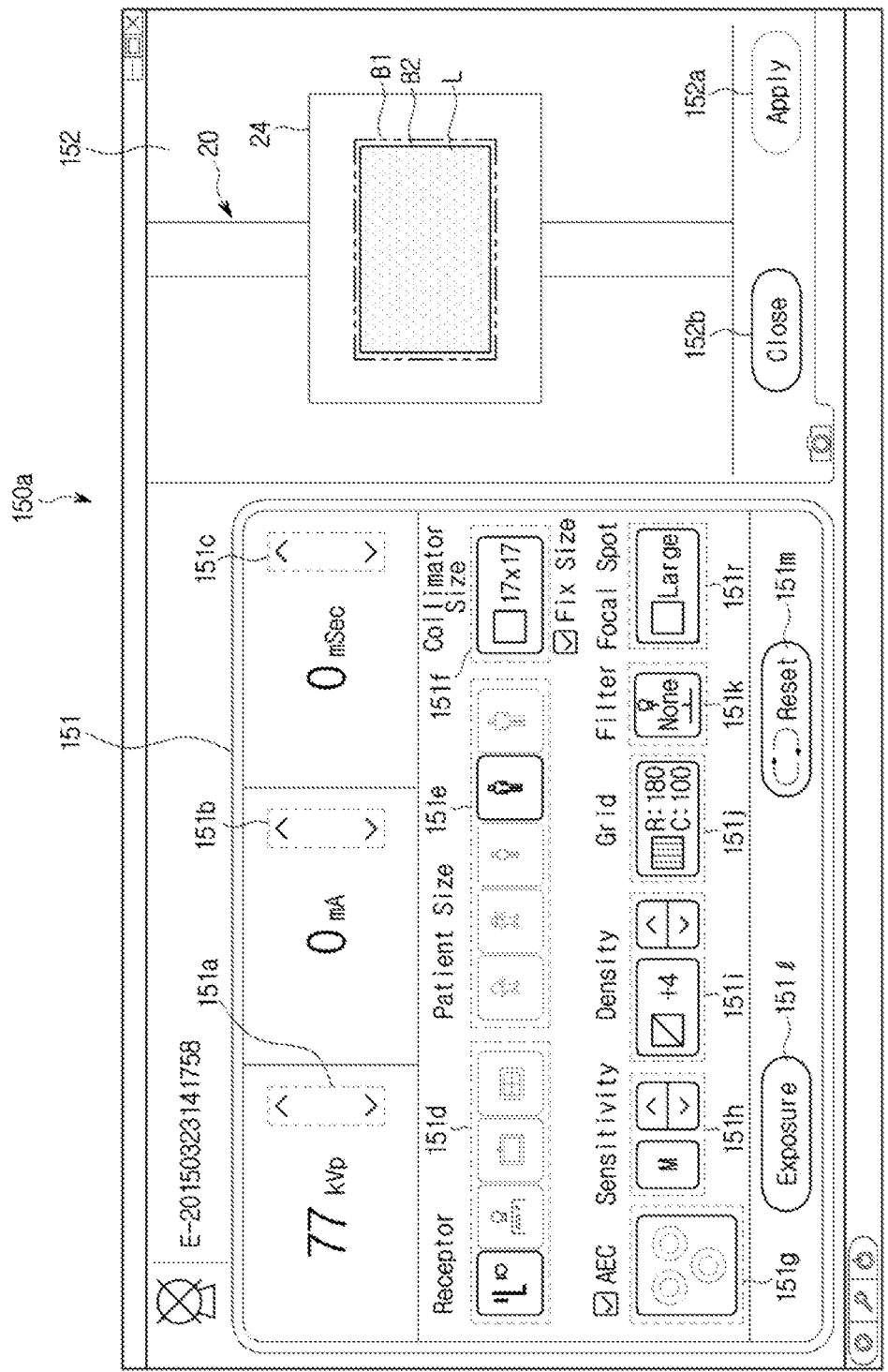
FIG. 10 is a view illustrating an X-ray irradiation window generated using coordinate information and an X-ray irradiation window generated through image processing.

FIG. 8A is a conceptual view illustrating light showing an X-ray irradiation region being radiated from the X-ray source, FIG. 8B is a view illustrating an example in which a light irradiation region is included in a camera image displayed on the display unit, and FIG. 9 is a view illustrating an example of displaying an X-ray irradiation window based on the light irradiation region. FIG. 10 is a view illustrating an X-ray irradiation window generated using coordinate information and an X-ray irradiation window generated through image processing.

Referring to FIG. 8A, a region matching the X-ray irradiation region E may be irradiated with visible rays VL by a light source included in the X-ray source 110, e.g., a collimator lamp.

As illustrated in FIG. 8B, a light irradiation region L generated on a surface of the mounting unit 24 by the visible rays VL is also shown in the camera image 152. The control unit 140 may extract a boundary of the light irradiation region L from the camera image 152 through image processing and may generate an X-ray irradiation window B2 based on the extracted boundary of the light irradiation region L as illustrated in FIG. 9. The generated X-ray irradiation window B2 may be displayed by being overlapped on the camera image 152. To distinguish the two X-ray irradiation windows B1 and B2 from each other, the X-ray irradiation window B1 generated by coordinate information may be referred to as a first X-ray irradiation window B1, and the X-ray irradiation window B2 generated through image processing may be referred to as a second X-ray irradiation window B2 in an embodiment to be described below.

The X-ray imaging apparatus 100 according to an embodiment undergoes a calibration process that matches the light irradiation region L formed by the collimator lamp and the actual X-ray irradiation region E and determines camera parameters such as the principal point, the focal length, and the installation angle, etc., of the capturing unit 120 so that the X-ray irradiation windows B1 and B2 displayed on the display unit 150 may accurately show the actual X-ray irradiation region E.

When an error does not occur in the calibration process, the X-ray irradiation window B1 generated using coordinate information and the X-ray irradiation window B2 generated through image processing match each other as illustrated in FIG. 10. Consequently, when the first X-ray irradiation window B1 and the second X-ray irradiation window B2 do not match each other, it may be determined that an error has occurred in the calibration process described above. Thus, the control unit 140 performs a process of verifying whether an error has occurred in the calibration process described above by performing a process of comparing the first X-ray irradiation window B1 and the second X-ray irradiation window B2.

Since differences between positions, forms, and sizes of the X-ray irradiation windows B1 and B2 generated using the two methods described above imply that an error has occurred in the calibration process, the control unit 140 may display, through the display unit 150, a message or the like requesting that calibration be performed. In addition, the two X-ray irradiation windows B1 and B2 not matching each other may be intuitively shown by displaying the first X-ray irradiation window B1 and the second X-ray irradiation window B2 by overlapping the first X-ray irradiation window B1 and the second X-ray irradiation window B2 on the camera image 152. The user may check the message and perform the calibration process described above again.

In addition, rather than displaying the message that requests that calibration be performed, the control unit 140 may calculate a degree of discordance to calculate a calibration parameter for solving the discordance when the X-ray irradiation windows generated using the two methods described above do not match each other. The calibration may be automatically performed based on the calculated calibration parameter, and the calibration parameter may be displayed on the display unit 150 to guide the user to perform the calibration.

The control unit 140 may calculate a focal length and a principal point of the capturing unit 120 required for solving the discordance based on discordance information, and may calculate variables required for converting the global coordinate system into the camera coordinate system.

In addition, in the disclosed embodiment, an offset may occur due to a difference between the focal point of the capturing unit 120 and a focal point of the X-ray tube 111. The control unit 140 may use the discordance information to calculate parameters required to compensate for the offset. The control unit 140 may automatically perform calibration using the parameters calculated as above or may assist the user to perform calibration by displaying the calculated parameters through the display unit 150.

Meanwhile, prior to X-ray imaging, the X-ray imaging apparatus 100 according to an embodiment may perform a process of aligning the X-ray source 110 and the X-ray detector 200 with each other. The X-ray source 110 and the X-ray detector 200 may be aligned with each other by matching a center of the X-ray irradiation region and a center of the X-ray detector 200. Hereinafter, this will be described in detail with reference to FIGS. 11 to 15.

FIGS. 11 to 15 are views illustrating a method for aligning the X-ray source and an X-ray detector of the X-ray imaging apparatus according to an embodiment to each other.

Figure 11:
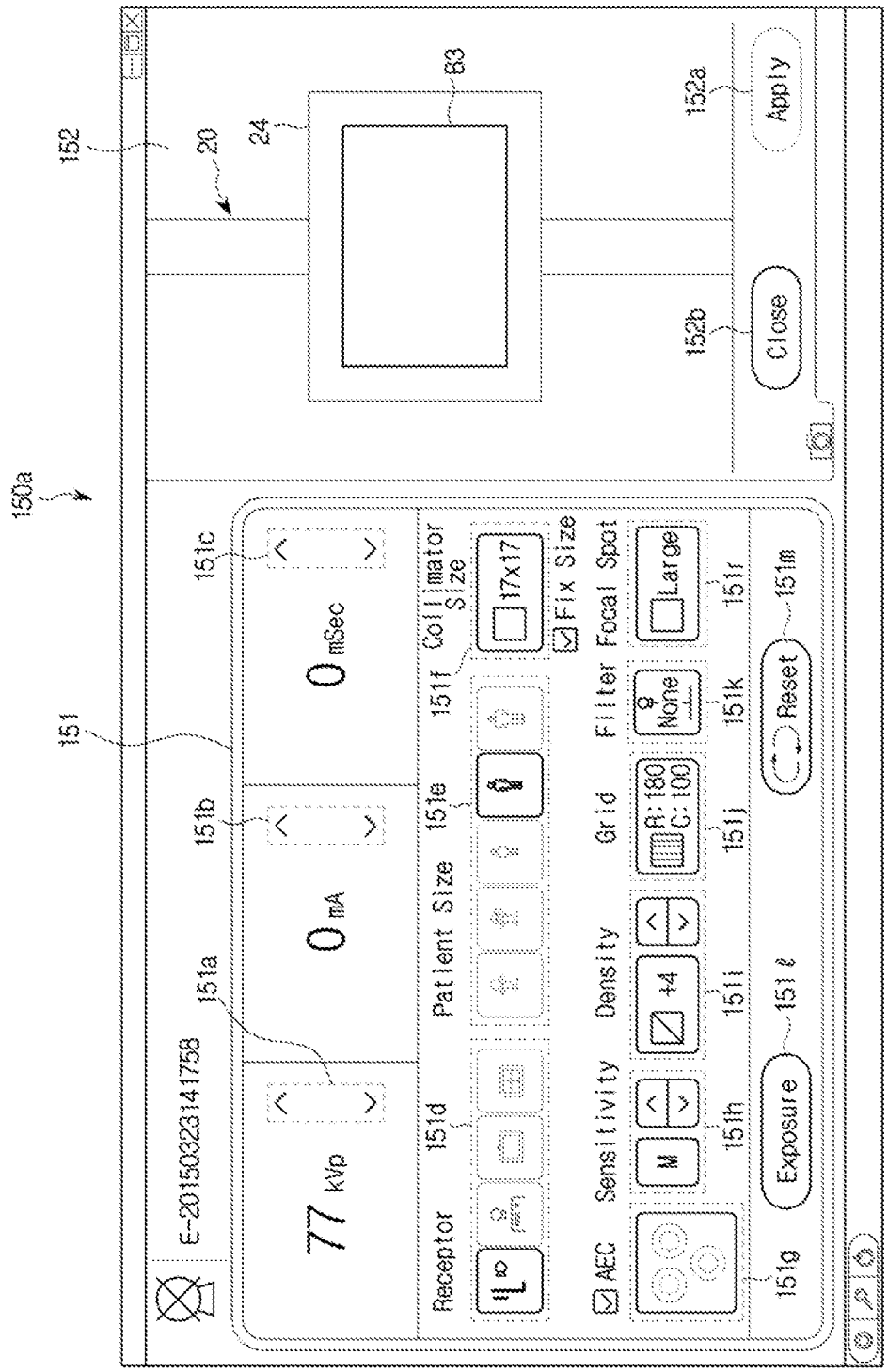
FIGS. 11, 12, 13, 14, and 15 are views illustrating a method for aligning the X-ray source and an X-ray detector of the X-ray imaging apparatus according to an embodiment to each other.

As illustrated in FIG. 11, the control unit 140 generates an X-ray irradiation window B31 by the method using coordinate information or the method of extracting a boundary of an X-ray irradiation region through image processing which are described above, and displays the generated X-ray irradiation window B3 by overlapping the generated X-ray irradiation window B3 on the camera image 152 acquired by the capturing unit 120.

Figure 12:
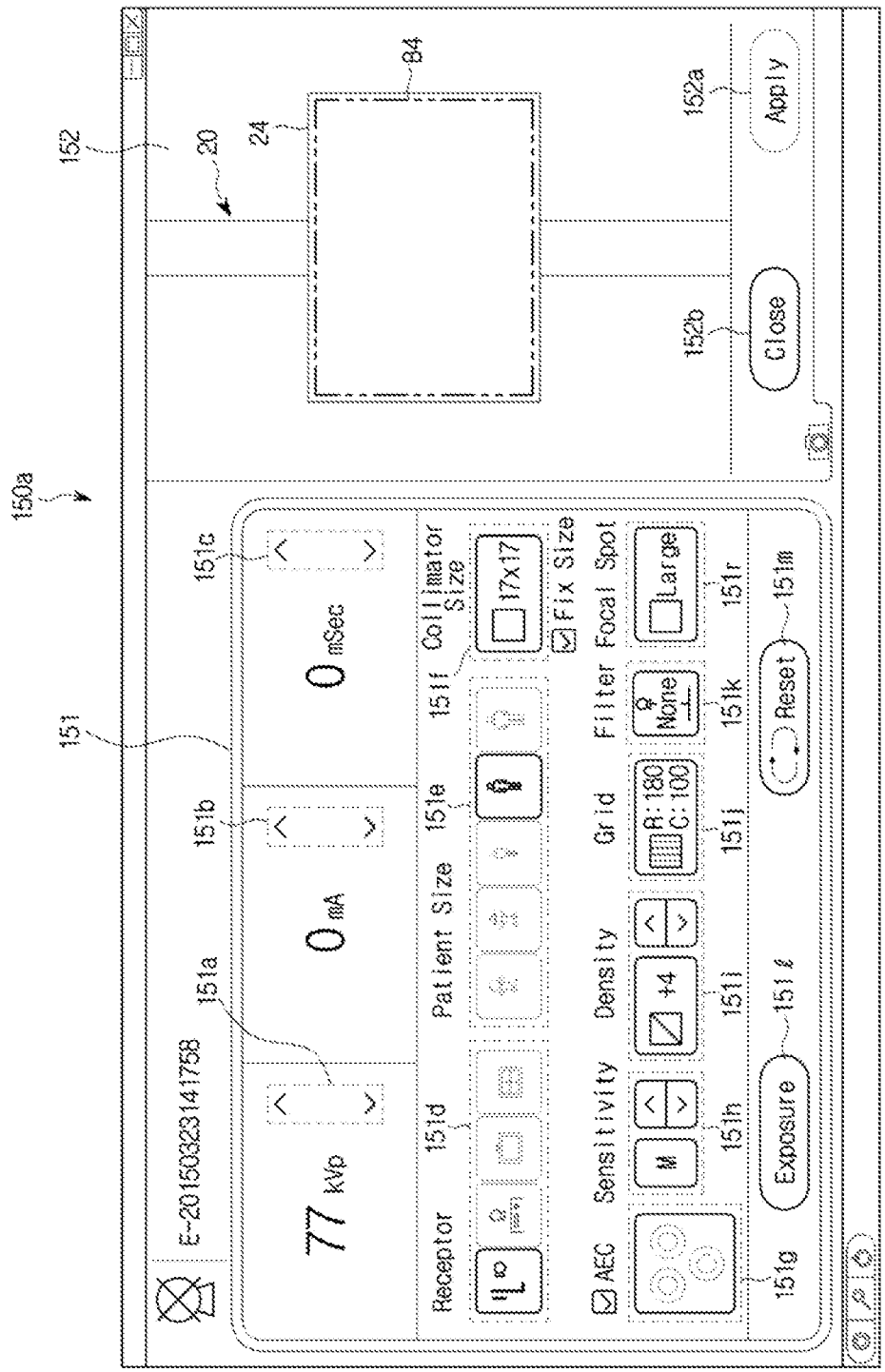

In addition, as illustrated in FIG. 12, the control unit 140 generates a detector boundary line B4 showing a boundary of the X-ray detector 200 by the method using coordinate information or the method of extracting a boundary of the X-ray detector 200 shown in the camera image 152 through image processing which are described above, and displays the generated detector boundary line B4 by overlapping the generated detector boundary line B4 on the camera image 152 acquired by the capturing unit 120. When the X-ray detector 200 is mounted inside the mounting unit 24 as in this example, the mounting unit 24 shown in the camera image 152 may be used instead of the X-ray detector 200.

The X-ray irradiation window B3 and the detector boundary line B4 displayed by being overlapped on the camera image 152 may be distinguished from each other by being displayed with different colors. In FIGS. 11 to 15, the X-ray irradiation window B3 is displayed with a solid line and the detector boundary line B4 is displayed with a dotted line.

Figure 13:
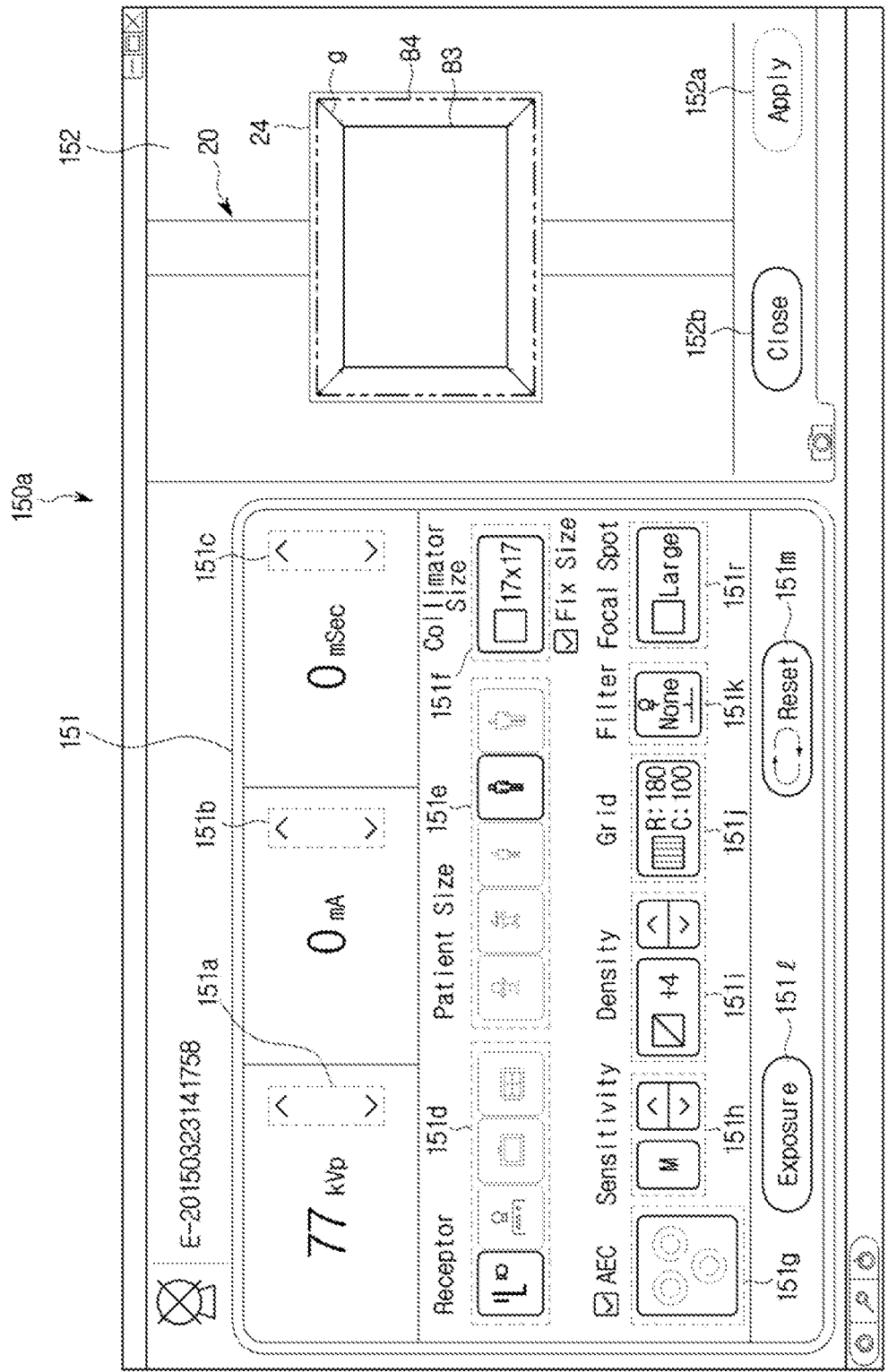
Figure 14:
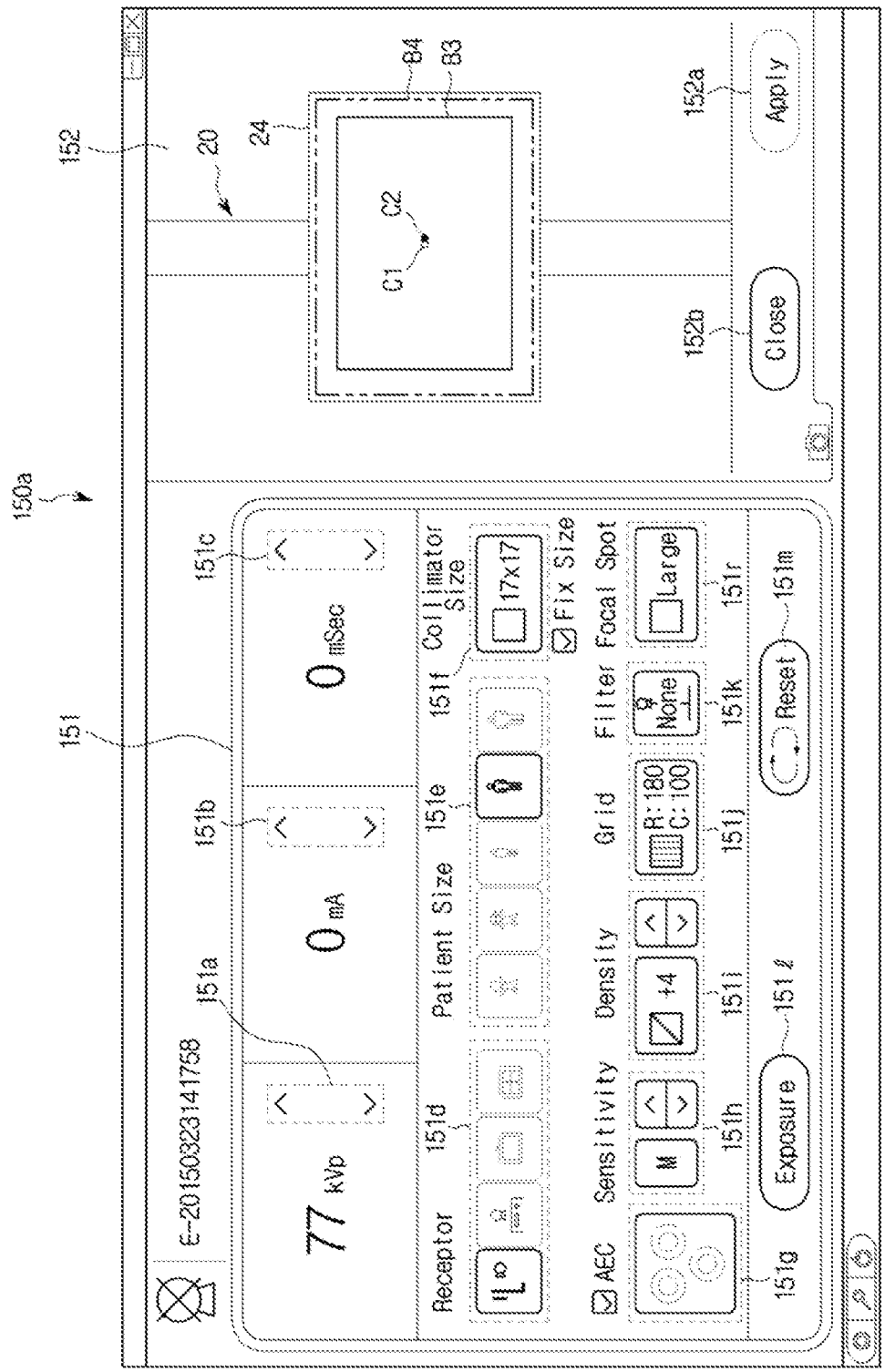

In FIGS. 13 and 14, an example in which the detector boundary line B4 and the X-ray irradiation window B3 are displayed together on the display unit 150 is illustrated.

When intervals g between four vertices of the X-ray irradiation window B3 and four vertices of the detector boundary line B4 respectively corresponding thereto are all the same as illustrated in FIG. 13, the control unit 140 may determine that the X-ray detector 200 and the X-ray source 110 are aligned with each other.

Alternatively, when a center c1 of the X-ray irradiation window B3 and a center c2 of the detector boundary line B4 match each other as illustrated in FIG. 14, the control unit 140 may determine that the X-ray detector 200 and the X-ray source 110 are aligned with each other.

Figure 15:
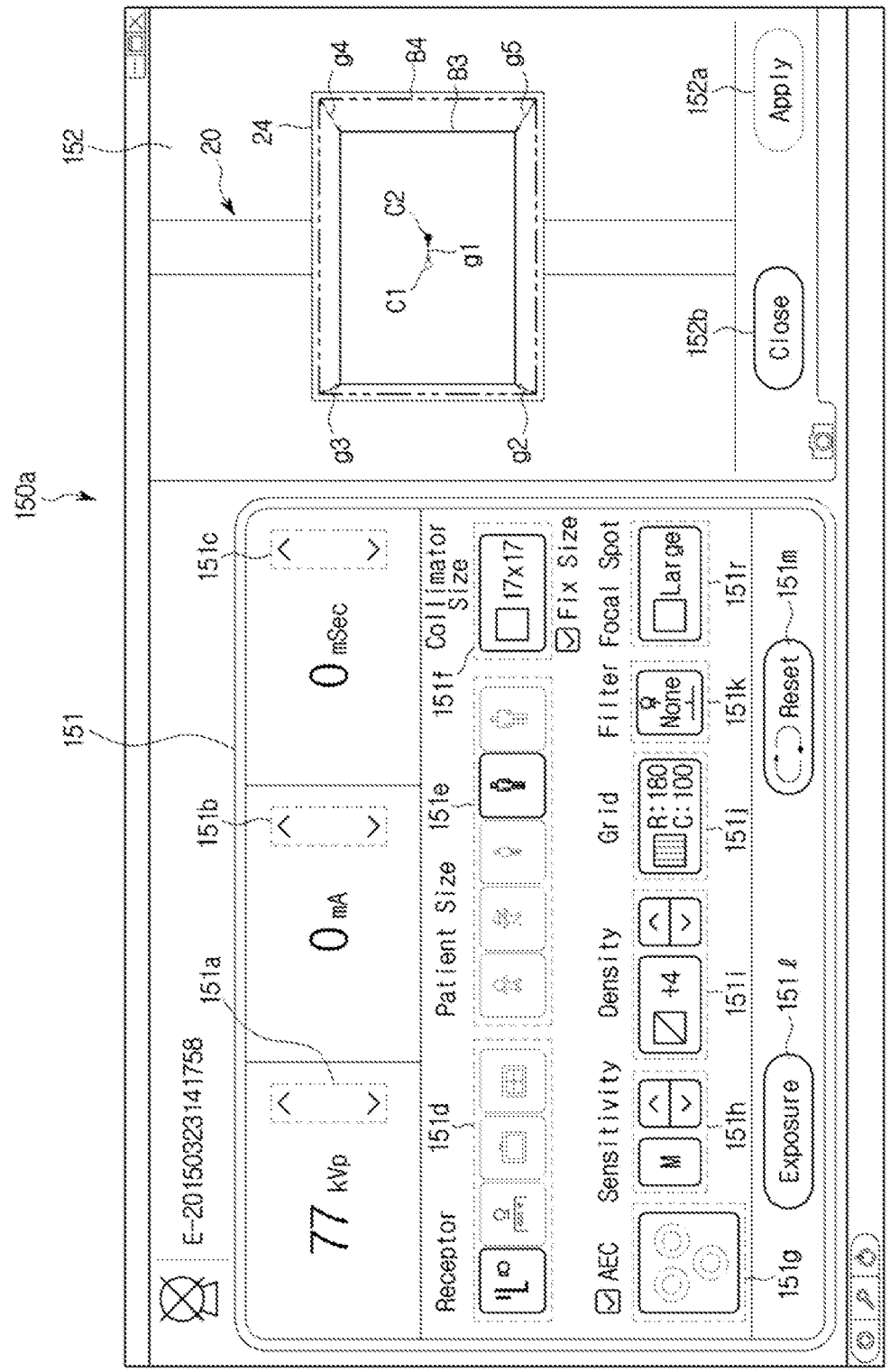

When intervals g2, g3, g4, and g5 between the four vertices of the X-ray irradiation window B3 and the four vertices of the detector boundary line B4 respectively corresponding thereto are different from each other, or the center c1 of the X-ray irradiation window B3 and the center c2 of the detector boundary line B4 do not match each other as illustrated in FIG. 15, the control unit 140 may determine that the X-ray detector 200 and the X-ray source 110 are not aligned with each other. In this case, the control unit 140 may calculate the intervals g2, g3, g4, and g5 between the four vertices of the X-ray irradiation window B3 and the four vertices of the detector boundary line B4 respectively corresponding thereto and calculate a moving distance and a moving direction of the X-ray source 110 or the X-ray detector 200 that matches the calculated intervals to each other.

The control unit 140 may match the intervals by moving the X-ray source 110 or the X-ray detector 200 according to the moving distance and the moving direction of the X-ray source 110 or the X-ray detector 200 calculated as above.

Alternatively, the control unit 140 may also guide the user to move the X-ray source 110 or the X-ray detector 200 by displaying the calculated moving distance and moving direction of the X-ray source 110 or the X-ray detector 200 through the display unit 150.

Alternatively, the control unit 140 may calculate an interval g1 between the center c1 of the X-ray irradiation window and the center c2 of the detector boundary line and, based on the calculated interval, may calculate a moving direction and a moving distance of the X-ray source 110 or the X-ray detector 200 that matches the center of the X-ray irradiation window and the center of the detector boundary line. The control unit 140 may match the center of the X-ray irradiation window and the center of the detector boundary line by moving the X-ray source 110 or the X-ray detector 200 according to the moving distance of the X-ray source 110 or the X-ray detector 200 calculated as above.

Alternatively, the control unit 140 may also guide the user to move the X-ray source 110 or the X-ray detector 200 by displaying the calculated moving direction or moving distance of the X-ray source 110 or the X-ray detector 200 through the display unit 150.

The moving distance and the moving direction of the X-ray source 110 or the X-ray detector 200 may also be displayed as text, and the X-ray irradiation window B3, the detector boundary line B4, the intervals between the vertices that do not match each other, and the interval between the center c1 of the X-ray irradiation window and the center c2 of the detector boundary line may also be displayed as images as illustrated in FIG. 15.

Meanwhile, when the X-ray source 110 and the X-ray detector 200 are aligned with each other, the user may input a predetermined operation command through the input unit 160 to adjust a position, size, or form of the X-ray irradiation window B3 displayed on the display unit 150. For example, the position, size, or form of the X-ray irradiation window B3 may be adjusted by dragging a boundary of the X-ray irradiation window B3.

The X-ray irradiation window B3 may deviate from the boundary of the X-ray detector 200 while the user adjusts the X-ray irradiation window B3.

Figure 16:
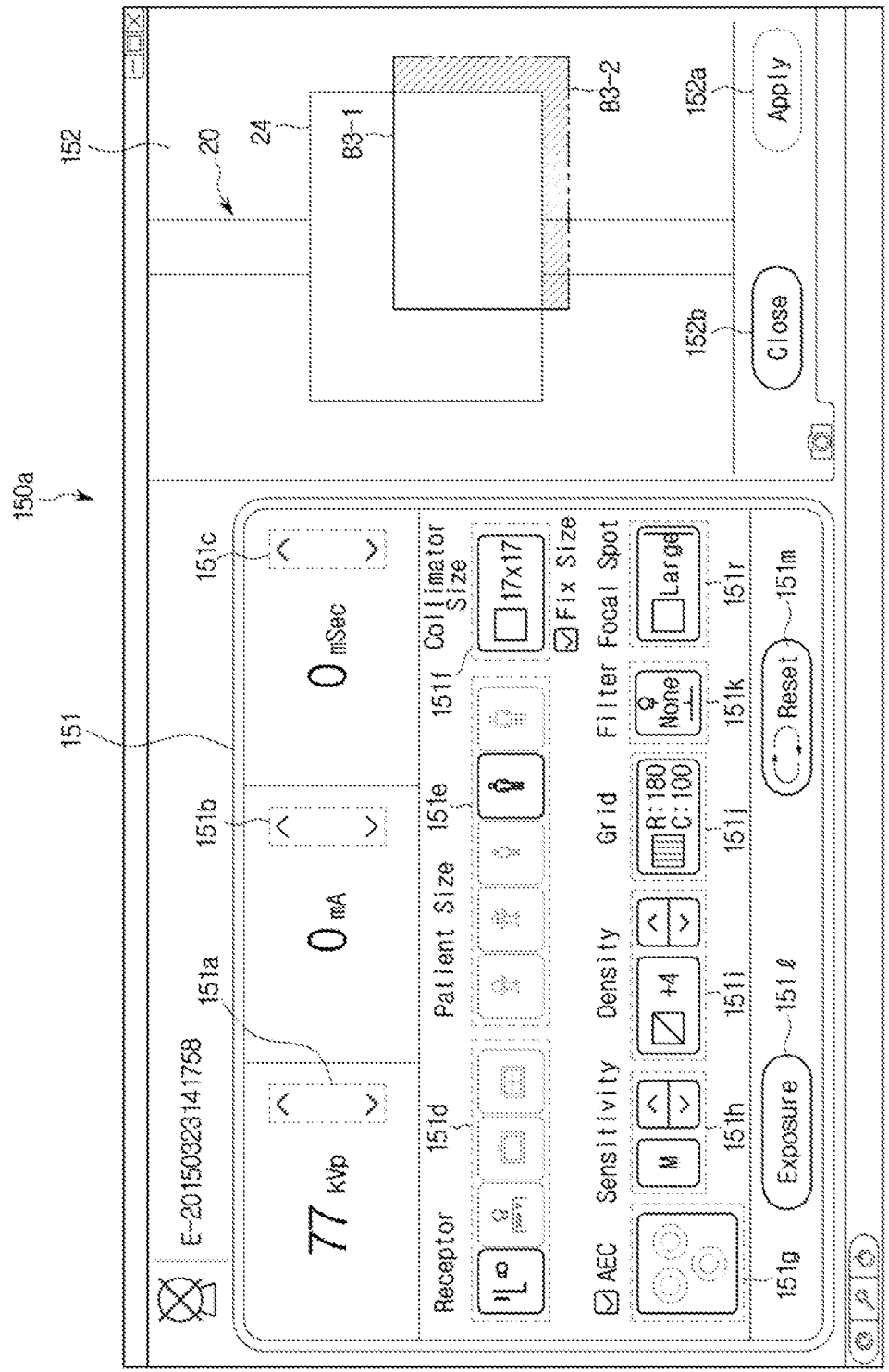
FIG. 16 is a view illustrating an example in which an X-ray irradiation window displayed on the display unit of the X-ray imaging apparatus according to an embodiment is deviated from a boundary of the X-ray detector.

FIG. 16 a view illustrating an example in which an X-ray irradiation window displayed on the display unit of the X-ray imaging apparatus according to an embodiment is deviated from a boundary of the X-ray detector.

As illustrated in FIG. 16, the X-ray irradiation window B3 displayed on the display unit 150 may partially deviate from the boundary of the X-ray detector 200 shown in the camera image 152. Also in this example, the X-ray detector 200 is mounted inside the mounting unit 24, and only the mounting unit 24 is shown in the camera image 152. In this case, whether the X-ray irradiation window B3 is deviated from the boundary of the X-ray detector 200 may be determined based on whether the X-ray irradiation window B3 is deviated from the boundary of the mounting unit 24.

Although a case in which the X-ray irradiation window B3 is partially deviated from the boundary of the X-ray detector 200 is illustrated in FIG. 16, the X-ray irradiation window B3 may also entirely deviate from the boundary of the X-ray detector 200.

When a region deviated from the boundary of the X-ray detector 200 is also irradiated with X-rays, unnecessarily excessive X-ray exposure may occur. When the X-ray irradiation window B3 deviates from the boundary of the X-ray detector 200 shown in the camera image 152, the control unit 140 may inform the user by displaying a region B3-2 that is deviated from the boundary of the X-ray detector 200 and a region B3-1 that is present within the boundary of the X-ray detector 200 with different colors as illustrated in FIG. 16 to prevent excessive X-ray exposure.

For example, the control unit 140 may display the region B3-1 that is present within the boundary of the X-ray detector 200 as green and the region B3-2 that is deviated from the boundary of the X-ray detector 200 as red to inform the user that the X-ray irradiation window B3 has deviated from the boundary of the X-ray detector 200. For reference, in the example shown in FIG. 15, a boundary of the X-ray irradiation window B3 that is present within the boundary of the X-ray detector 200 is displayed using a solid line, and a boundary of the X-ray irradiation window B3 that is deviated from the boundary of the X-ray detector 200 is displayed using a dotted line to distinguish the two from each other.

Using different colors or a dotted line and a solid line to inform that the X-ray irradiation window has deviated from the boundary of the X-ray detector 200 is merely an example, and a sound or a vibration of the input unit 160 may also be used. That is, the X-ray imaging apparatus 100 may inform the user that the X-ray irradiation window displayed on the display unit 150 has deviated from the boundary of the X-ray detector 200 using various methods based on a visual, aural, or tactile stimulation.

Meanwhile, to determine whether the X-ray irradiation window B3 has deviated from the boundary of the X-ray detector 200 shown in the camera image 152, the control unit 140 may compare a relation between positions of the detector boundary line B4 and the X-ray irradiation window B3 described above.

Since X-ray imaging is performed on the X-ray irradiation region E, the X-ray irradiation region may correspond to an X-ray imaging region. When the X-ray imaging region is designated, the control unit 140 may control the collimator 113 to match the X-ray irradiation region E and the designated X-ray imaging region.

The X-ray imaging region may be directly designated by the user when X-ray imaging is performed, but it may also be automatically designated by being preset for each of a plurality of imaging protocols and selecting one of the imaging protocols when X-ray imaging is performed later. Hereinafter, this will be described in detail with reference to the drawings.

Figure 17:
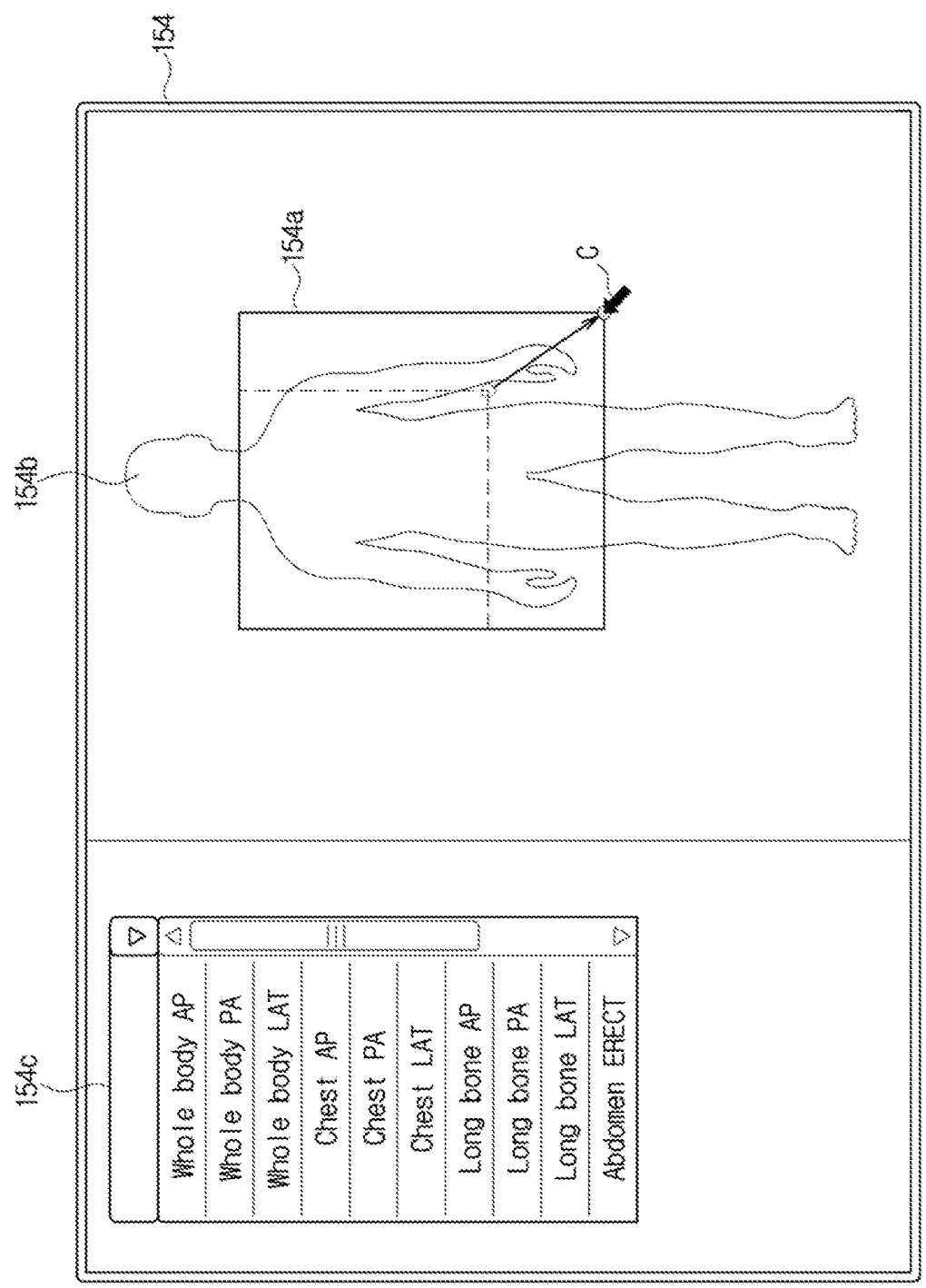
FIGS. 17, 18, and 19 are views illustrating examples of presetting an imaging region according to an imaging protocol.
Figure 18:
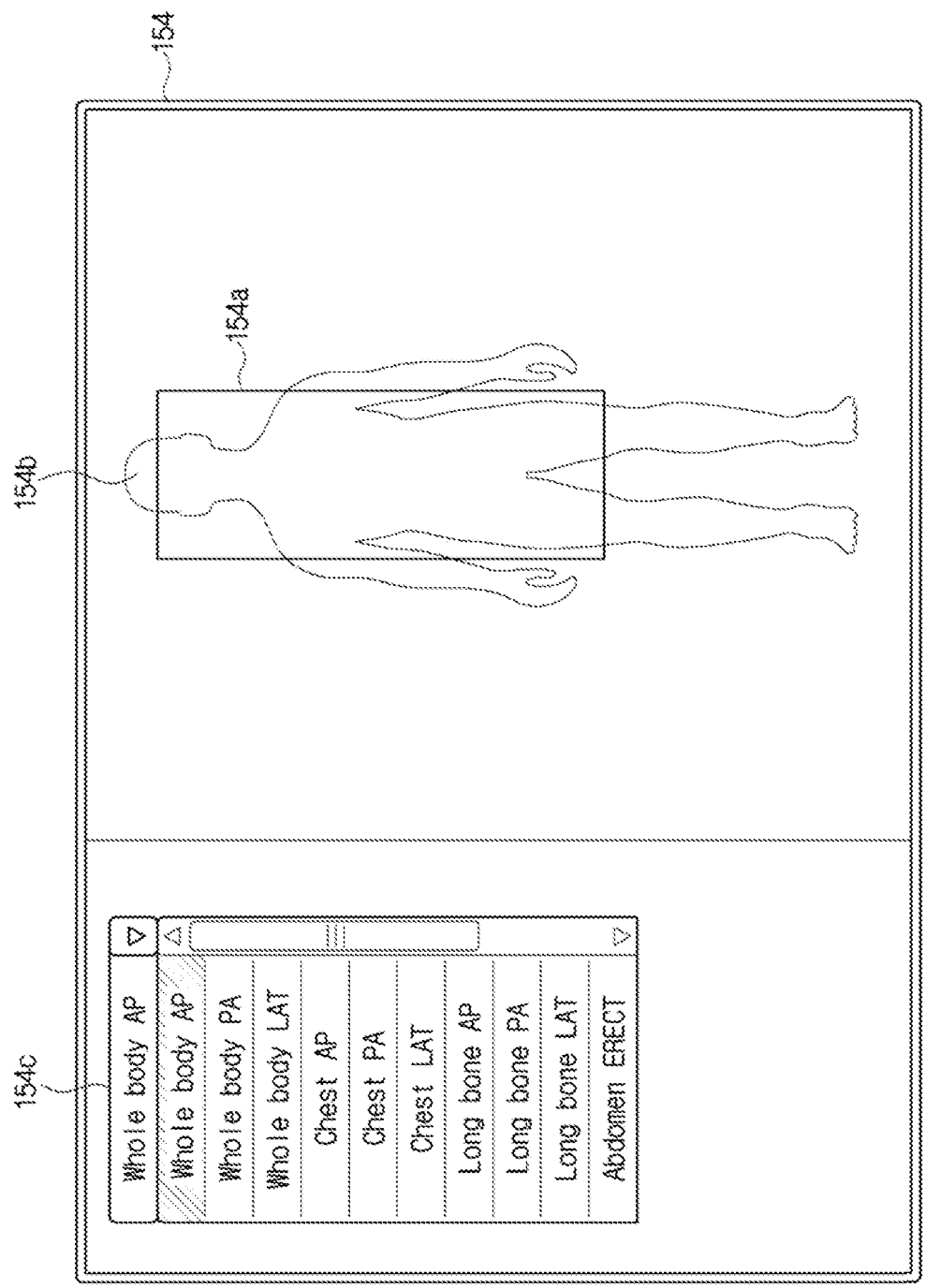
Figure 19:
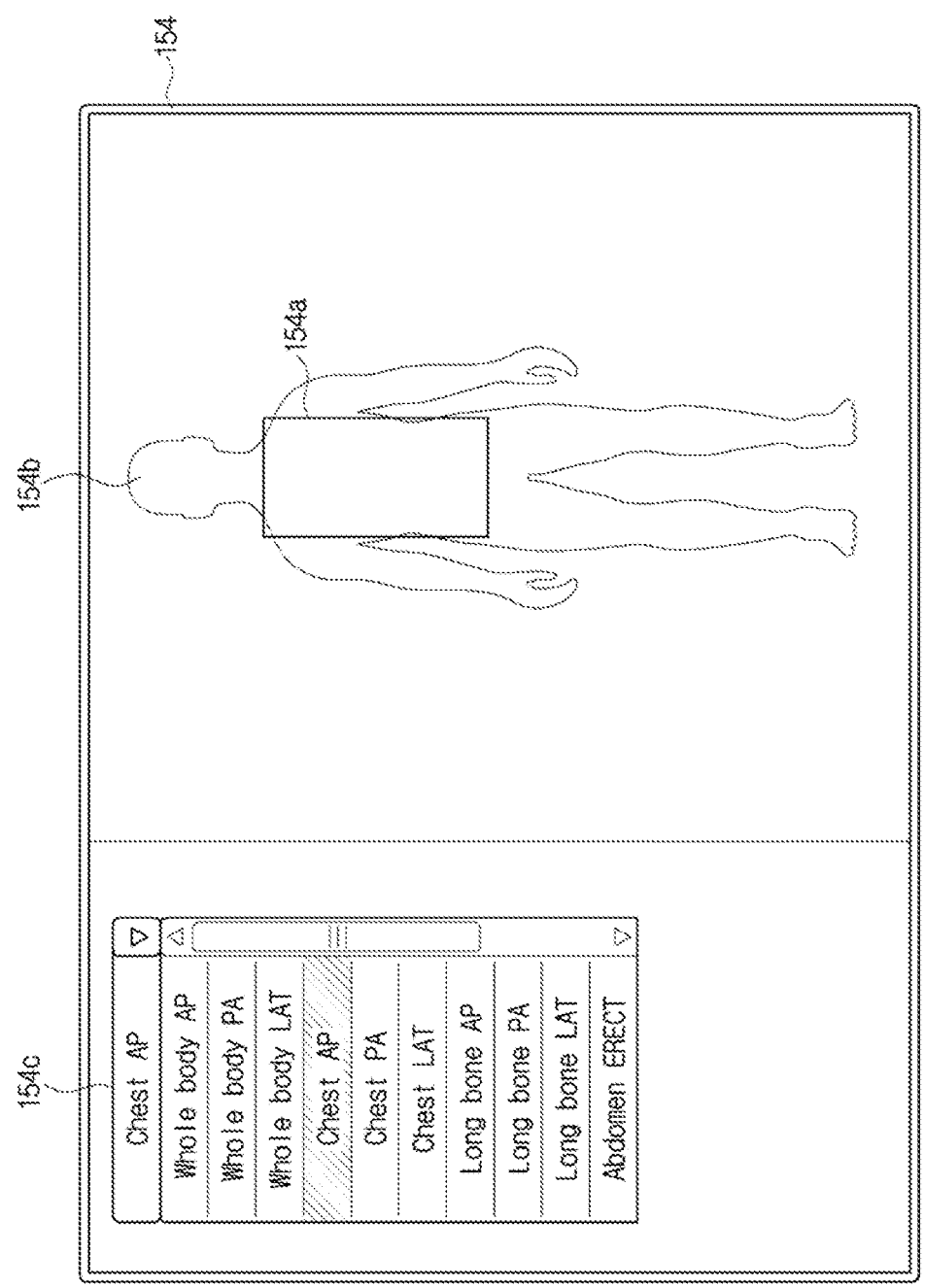
Figure 20:
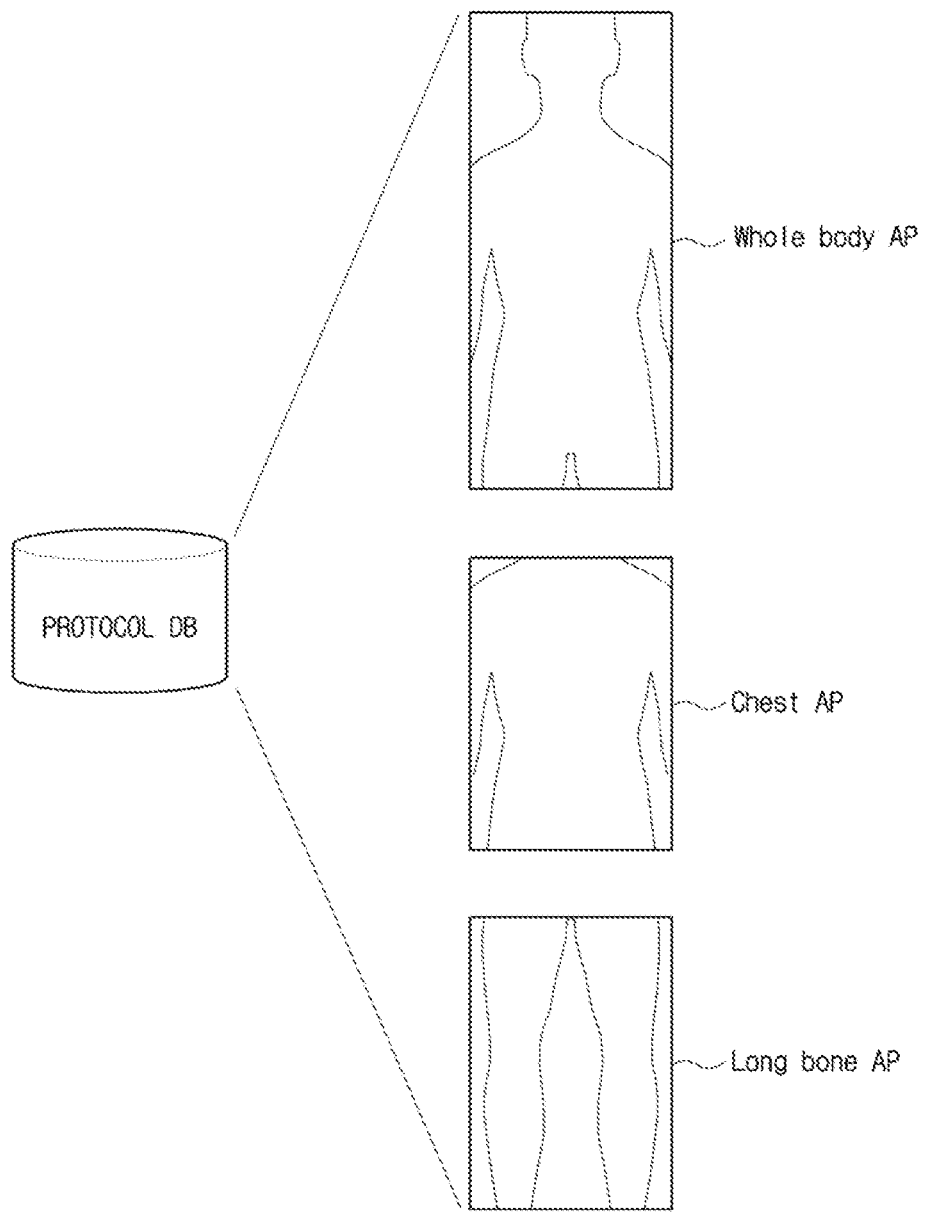
FIG. 20 is a view illustrating information stored in a storage unit.

FIGS. 17 to 19 are views illustrating examples of presetting an imaging region according to an imaging protocol, and FIG. 20 is a view illustrating information stored in a storage unit As illustrated in FIG. 17, an imaging region may be preset for each of a plurality of imaging protocols. The description related to the imaging protocols is the same as described above.

To preset the imaging region for each of the plurality of imaging protocols, the display unit 150 may display an imaging protocol setting window 154. The imaging protocol setting window 154 may include a protocol list 154c.

The user may select an imaging protocol whose imaging region is desired to be set by the user from the protocol list 154c using the input unit 160.

To receive a setting of an imaging region, an object model 154b having a shape similar to that of an object, e.g., a target to be imaged, may be displayed on the display unit 150, and the user may adjust a position and size of an imaging window 154a displayed on the object model 154b to set an imaging region of the selected imaging protocol. In this embodiment, the object is a human body, and the object model 154b has a shape of a human body. The object model 154b is only required to show a rough silhouette of the object and does not have to show a detailed structure of the object.

For example, a size or position of the imaging window 154a may be adjusted by placing a cursor C on an edge or a vertex of the imaging window 154a and selecting and dragging the imaging window 154a.

Although the shape of the imaging window 154a may be quadrilateral as in this example, the shape is not limited thereto, and the imaging window 154a may also have shapes other than a quadrilateral shape including a polygonal shape, a circular shape, and an elliptical shape.

In detailed examples of setting an imaging region for each of the plurality of imaging protocols, a region from a face to portions above knees of the object as illustrated in FIG. 18 may be set as a whole body AP, and a region from a neck to a waist of the object as illustrated in FIG. 19 may be set as a chest AP.

As illustrated in FIG. 20, a set imaging region may be mapped to an imaging protocol corresponding thereto and stored in a protocol database (DB), and the protocol DB may be stored in the storage unit 170.

In addition, an X-ray irradiation condition may also be mapped and stored for each of the plurality of imaging protocols together with the imaging region. In this case, the X-ray irradiation condition may be preset for each of the plurality of imaging protocols or may be set by the user.

When X-ray imaging is performed and one of the plurality of imaging protocols is selected, the control unit 140 may search in the storage unit 170 for an imaging region mapped to the selected imaging protocol and perform X-ray imaging of the found imaging region.

In addition, when an X-ray irradiation condition is mapped and stored together with an imaging region, X-ray imaging may be performed by applying the stored X-ray irradiation condition.

Figure 21:
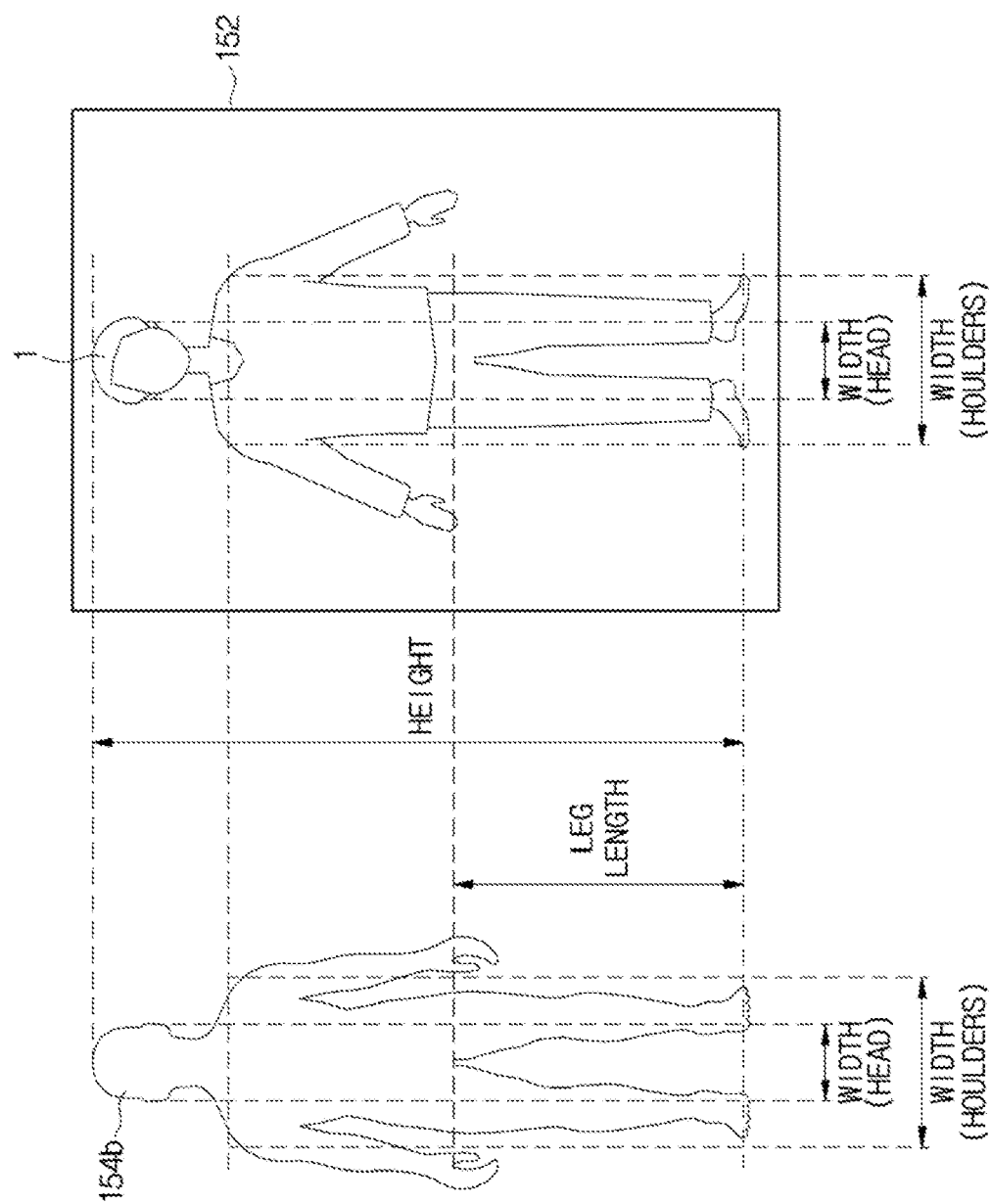
FIG. 21 is a view illustrating a process of extracting an imaging region corresponding to an imaging protocol from an image of an object.
Figure 22:
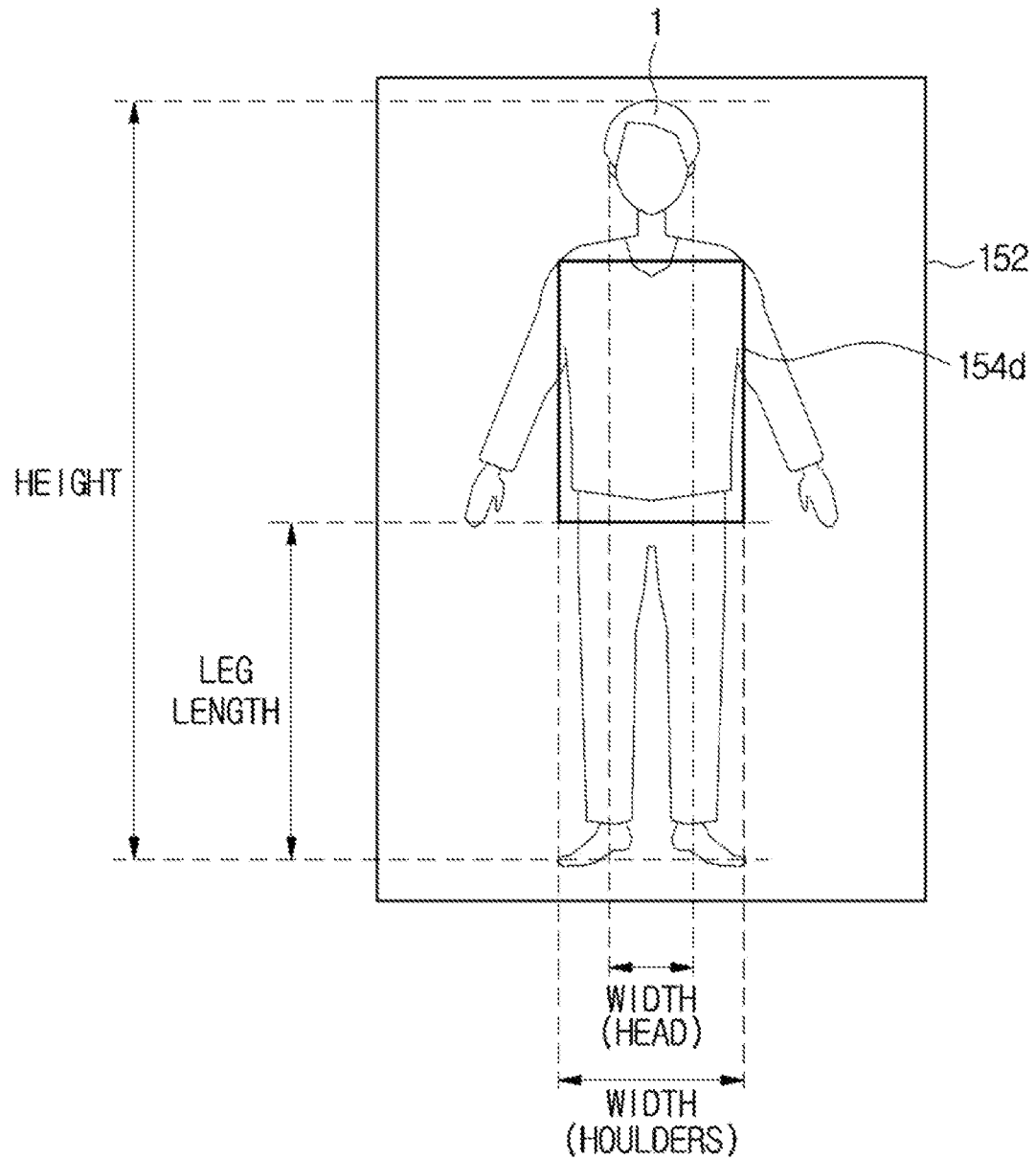
FIG. 22 is a view illustrating a camera image in which an extracted imaging region is displayed.

FIG. 21 is a view illustrating a process of extracting an imaging region corresponding to an imaging protocol from an image of an object, and FIG. 22 is a view illustrating a camera image in which the extracted imaging region is displayed.

The user may select an imaging protocol before X-ray imaging is performed, and the capturing unit 120 may capture the camera image 152 while the object is disposed in front of the X-ray detector 200.

The control unit 140 may search in the storage unit 170 for an imaging region mapped to the selected imaging protocol and extract the imaging region from the camera image 152.

The control unit 140 may extract the imaging region from the camera image 152 by applying image processing such as an object recognition algorithm thereto. For example, edge detection may be applied to the camera image 152 to extract a silhouette or a form of the object and detect a few features such as a length from head to toe (a height), a width of a head or shoulders, and a length of a leg required to recognize the imaging region. In this example, when an approximate height, width, and the like are recognized, required features may be detected based on the approximate height, width, and the like even without recognizing all detailed features of the object.

In another example, the form of an object may also be extracted by analyzing a difference between a camera image with the object and a camera image without the object, and various image processing technologies such as object pattern detection and face recognition may be applied to improve efficiency and accuracy of extracting an imaging region.

When an imaging region is extracted from the camera image 152 by the control unit 140, the control unit 140 may control the collimator 113 such that the X-ray irradiation region E corresponds to the imaging region. That is, the control unit 140 may control the collimator 113 so that the imaging region is irradiated with X-rays. Here, when the X-ray source 110 or the X-ray detector 200 needs to be moved, the X-ray source 110 or the X-ray detector 200 may be moved to a position corresponding to the imaging region. In addition, when the imaging region has a range which cannot be covered by performing a single X-ray imaging, the imaging region may be divided and stitching imaging may be performed.

In addition, the display unit 150 may display the extracted imaging region by overlapping the extracted imaging region 154*d* on the camera image 152 as illustrated in FIG. 22 to provide the user with information related to a region of the object 1 which will be captured.

Figure 23:
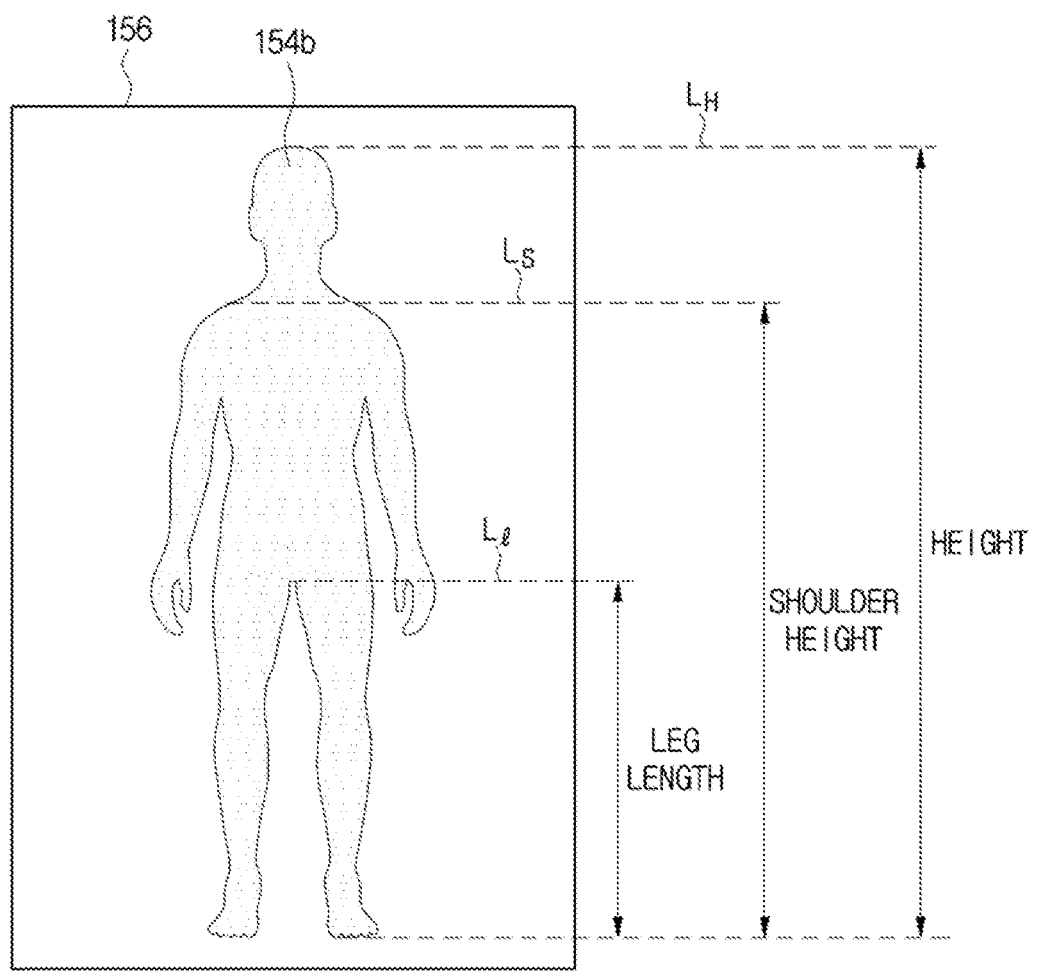
FIG. 23 is a view illustrating an operation of presetting information related to a size of the object.
Figure 24:
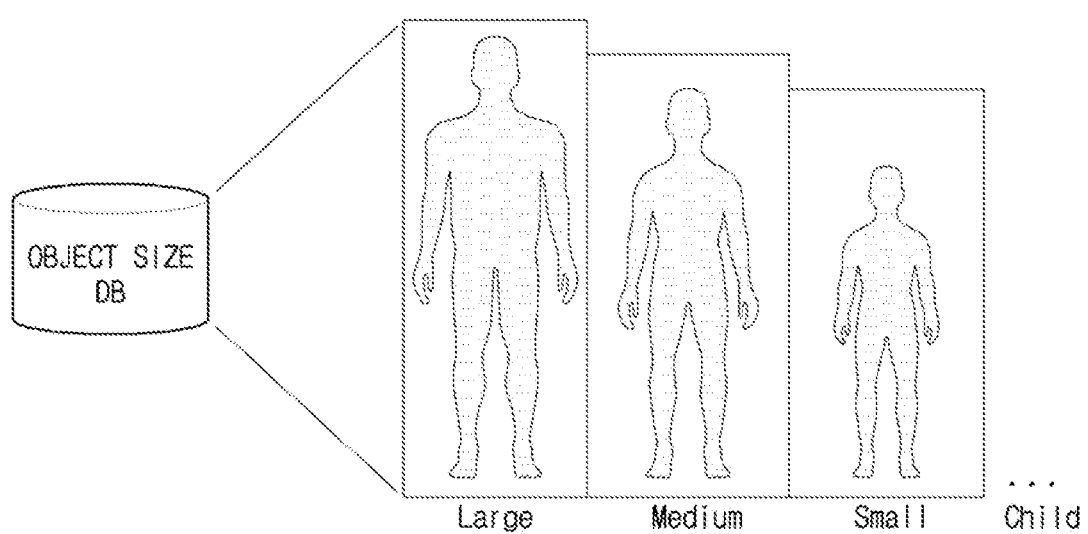
FIG. 24 is a view illustrating pre-stored information related to the size of the object.

FIG. 23 is a view illustrating an operation of presetting information related to a size of the object, and FIG. 24 is a view illustrating pre-stored information related to the size of the object.

An X-ray irradiation condition in which an optimal X-ray image may be obtained may vary depending on a size of an object, and an allowable value of X-ray exposure may vary according to the size of the object. Consequently, the X-ray imaging apparatus 100 according to an embodiment may preset an X-ray irradiation condition corresponding to each of a plurality of sizes of an object, and the user may directly classify the sizes of the objects.

Referring to an example shown in FIG. 23, the display unit 150 may display an object size setting screen 156. Specifically, the display unit 150 may display the object model 154*b* and classify the sizes of the objects using the input unit 160. In a detailed example, a height, a height of shoulders, and a length of legs may be designated and mapped as particular sizes. The height, the height of shoulders, and the length of legs may also be designated as particular values and may also be designated as a predetermined range.

To designate the height, the height of shoulders, and the length of legs, the user may directly input values, may vertically and horizontally drag an edge of the object model 154*b* displayed on the display unit 150, and may also vertically drag a line $L_H$ corresponding to a height of a head, a line Ls corresponding to the height of shoulders, and a line LL corresponding to the length of legs.

The sizes of the objects classified by the user may be stored in an object size DB as illustrated in FIG. 24, and the object size DB may be stored in the storage unit 170.

Although sizes of objects may be classified as large, medium, small, child, baby, etc., an embodiment of the X-ray imaging apparatus 100 is not limited thereto and may be further segmented or generalized.

Figure 25:
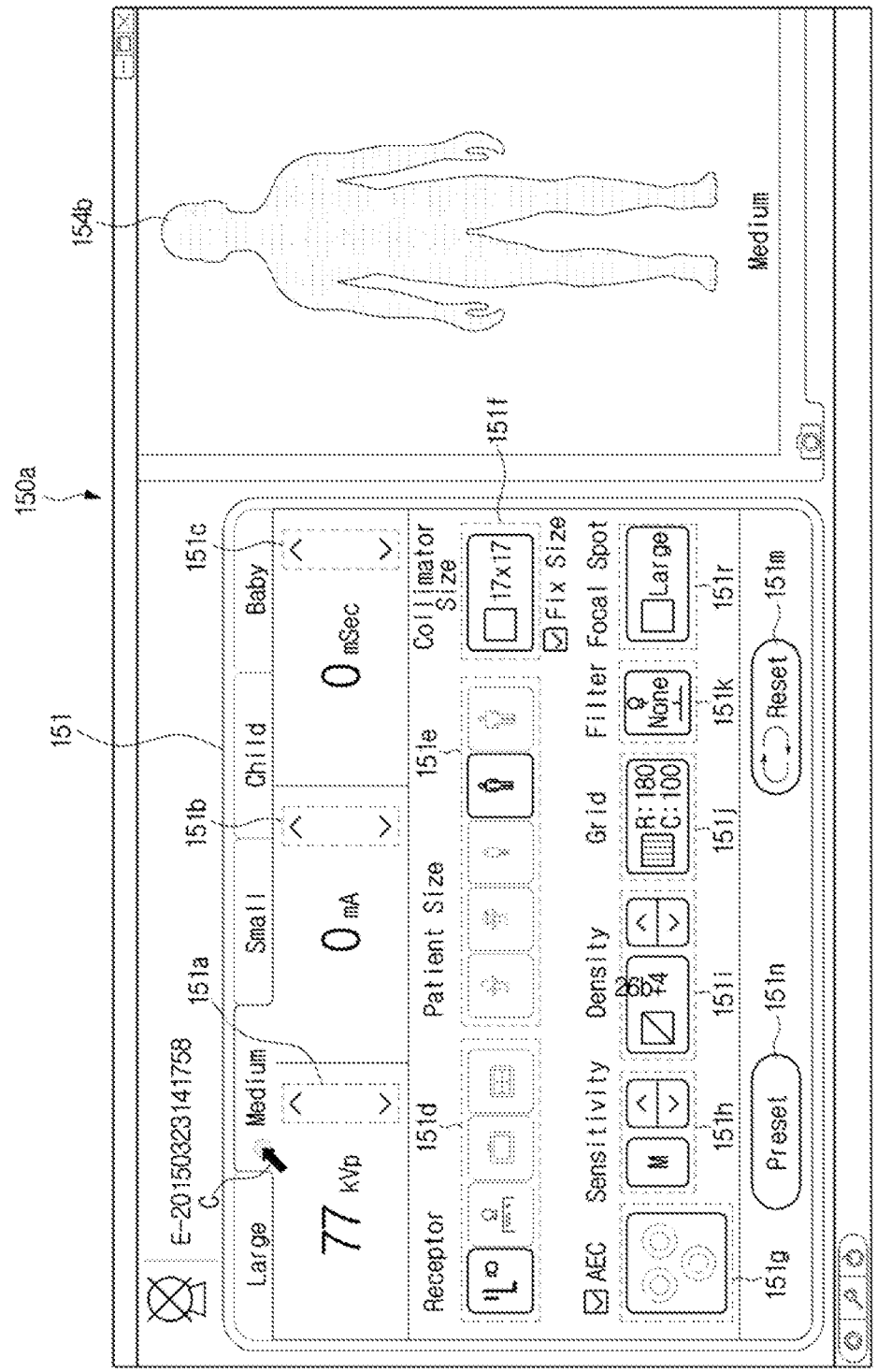
FIG. 25 is a view illustrating a screen through which an X-ray irradiation condition may be set for each of a plurality of sizes of an object.

FIG. 25 is a view illustrating a screen through which an X-ray irradiation condition may be set for each of a plurality of sizes of an object.

Referring to FIG. 25, the settings window 151 through which an X-ray irradiation condition may be set may be displayed on the screen 150*a* of the display unit 150. The user may set an X-ray irradiation condition for each of the plurality of sizes of an object.

The GUI through which an X-ray irradiation condition may be set for each of the plurality of sizes of an object may be displayed on the settings window 151. For example, identification tags (Large, Medium, Small, Child, and Baby) capable of identifying pre-classified sizes of objects may be displayed at an upper portion of the settings window 151, and, a menu through which an X-ray irradiation condition for the selected size of an object may be set may be activated when the user manipulates the input unit 160 to select one of the identification tags.

When the user moves the cursor C to select an identification tag corresponding to a medium size (Medium), the object model 154*b* in a medium size may be displayed at the right side of the settings window 151 as a result of interoperation.

When an object size whose X-ray irradiation condition is desired to be set is selected, a GUI through which an X-ray irradiation condition for the selected object size may be set may be activated.

When the GUI is activated, various types of graphical objects that may be used to set the X-ray irradiation condition of the selected object size may be displayed. For example, the tube voltage setting button 151*a* for receiving a tube voltage setting, the tube current setting button 151*b* for receiving a tube current setting, and the exposure time setting button 151*c* for receiving an X-ray exposure time setting may be displayed in the settings window 151. The user may select each of the buttons to set an X-ray irradiation condition to have a desired value.

In addition, the capture position setting button 151*d* for receiving a setting related to whether X-ray imaging will be performed at the stand 20 or at the table 10, the collimator setting button 151*f* for receiving a setting related to a size of the collimator 113, the AEC selection button 151*g* for receiving a selection related to an AEC sensor, the sensitivity setting button 151*h* for receiving a setting related to sensitivity, the button 151*i* for receiving a setting related to density, the grid selection button 151*j* for receiving a selection related to the grid, the filter selection button 151*k* for receiving a selection related to a filter, the focal point selection button 151*r* for receiving a selection related to a size of a focal point, etc. may be further displayed in the settings window 151.

The object size selection button 151*e* may interoperate with a selection of an identification tag. For example, when the use has selected the identification tag corresponding to the medium size (Medium), an icon of a medium-sized person included in the object size selection button 151e may be highlighted and displayed.

When the setting an X-ray irradiation condition for each of the plurality of sizes of an object is finished, the user may select the preset button 151n to finish setting and may select the reset button 151m when attempting to initialize the settings.

The GUI illustrated in FIG. 25 is merely an example that may be applied to the X-ray imaging apparatus 100, and it should be noted that the GUI may have a configuration different from that shown in FIG. 25.

Meanwhile, in addition to an object size in setting an X-ray irradiation condition, an imaging protocol may also be taken into consideration. In this case, an X-ray irradiation condition may be set for each of the plurality of object sizes by segmenting each of the object sizes according to imaging protocols. For example, a large size X-ray irradiation condition may be set by segmenting a large size according to a whole body PA, a whole body AP, a whole body LAT, a chest PA, a chest AP, a chest LAT, a leg PA, a leg AP, and a leg LAT, and other remaining sizes may also be set likewise.

In addition, when stitching imaging needs to be performed due to a feature of an imaging protocol, the stitching region may also be divided into a plurality of regions based on the object model and an X-ray irradiation condition may be set for each of the divided regions.

The X-ray irradiation condition set for each of the plurality of sizes of objects may also be stored in the storage unit 170 or may also be stored in the object size DB together with the sizes of objects, for example.

Figure 26:
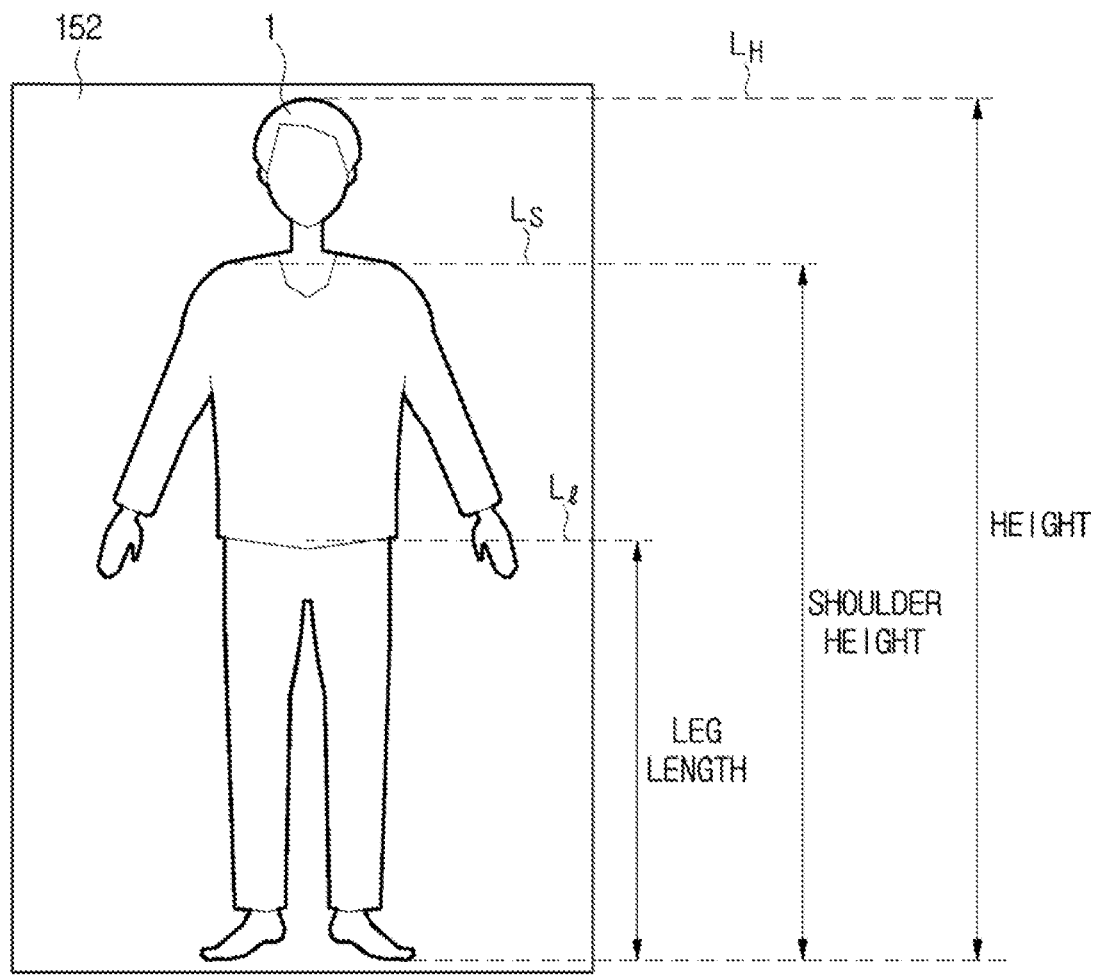
FIG. 26 is a view illustrating an operation of automatically determining a size of an object based on a camera image.

FIG. 26 is a view illustrating an operation of automatically determining a size of an object based on a camera image.

When the capturing unit 120 captures a camera image, the control unit 140 may analyze the camera image to automatically determine a size of an object.

For example, the control unit 140 may apply image processing such as an object recognition algorithm to recognize a leg starting point, a toe, a shoulder, a head, etc. of the object 1 from the camera image 152 and may calculate a leg length, a shoulder height, and a height in consideration of a recognition result, a source-to-image distance (ID), or a source-to-object distance (OD).

Alternatively, the control unit 140 may apply edge detection to the camera image to extract a silhouette of the object and may also estimate an approximate size of the object in consideration of the size of the silhouette of the object shown in the camera image, the SID, or the SOD.

For example, relations between the camera coordinate system based on the capturing unit 120, the global coordinate system of the space in which the X-ray imaging apparatus 100 is disposed, and the two-dimensional coordinate system of the camera image may be pre-stored, and conversions between the coordinate systems may be used to calculate the size of the silhouette of the object displayed in the camera image in actual space.

The control unit 140 may search in the storage unit 170 for an X-ray irradiation condition corresponding to the estimated object size, and may control the X-ray source 110 and the like according to the found X-ray irradiation condition.

Meanwhile, when the control unit 140 determines a size of an object, X-ray irradiation conditions mapped as a default for the corresponding size may be displayed on the settings window 151. The mapped X-ray irradiation conditions may be applied without change, or the user may select a button corresponding to each of the X-ray irradiation conditions and set each of the X-ray irradiation conditions again. Here, the user may set each of the X-ray irradiation conditions again with reference to default X-ray irradiation conditions displayed in the settings window 151.

As mentioned above, when an X-ray imaging portion of the object is larger than the X-ray irradiation region E or a detection region in which the X-ray detector 200 may detect X-rays, the X-ray imaging portion may be divided into a plurality of regions, and X-ray imaging may be separately performed for each of the plurality of divided regions.

Meanwhile, obtaining a single entire X-ray image by dividing the X-ray imaging portion into a plurality of regions, imaging each of the plurality of divided regions and stitching the X-ray images for each of the plurality of divided regions may be referred to by various terms such as panoramic imaging, stitching imaging, segmentation imaging, etc. For convenience of description, such imaging (panoramic imaging, stitching imaging, segmentation imaging, etc.) will be referred to as stitching imaging, in the embodiments which will be described. Also, each of the X-ray images for each of the divided regions will be referred to as divided X-ray image and each of the X-ray imaging for each of the divided regions will be referred to as divided imaging. Furthermore, one image generated by stitching together a plurality of divided X-ray images will be referred to as a stitched image. Hereinafter, an embodiment related to stitching imaging will be described in detail with reference to the drawings.

Figure 27:
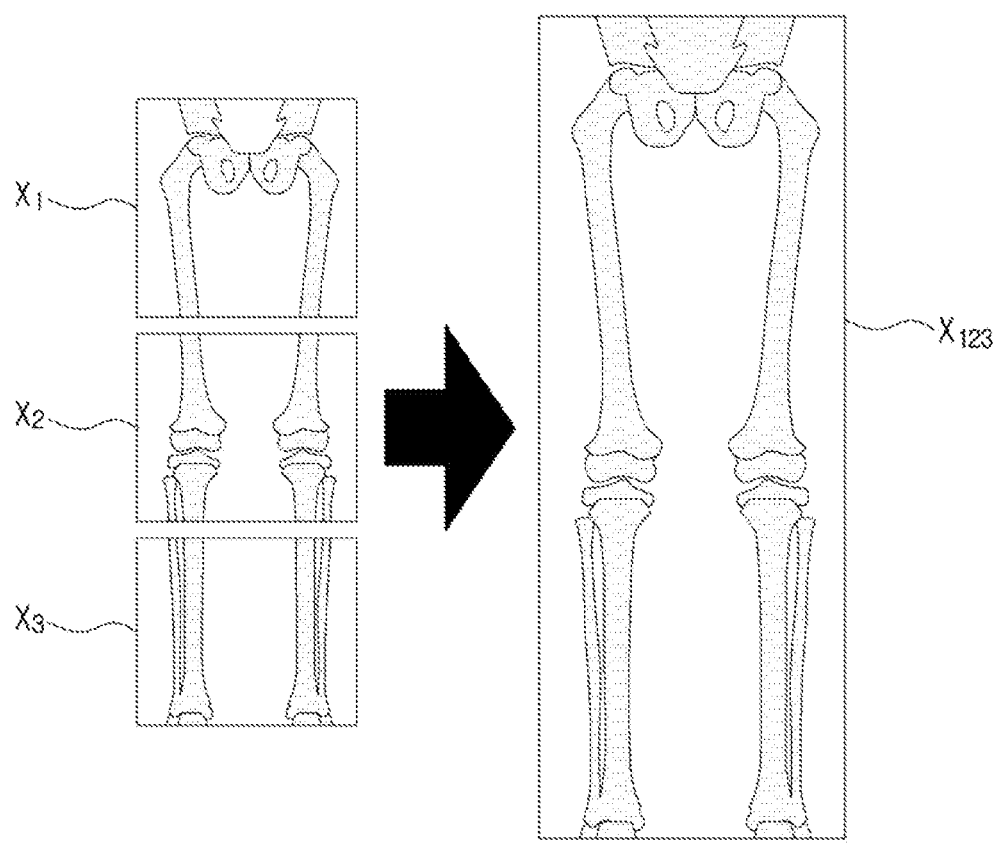
FIG. 27 is a view illustrating an example of a stitched-together image.
Figure 28:
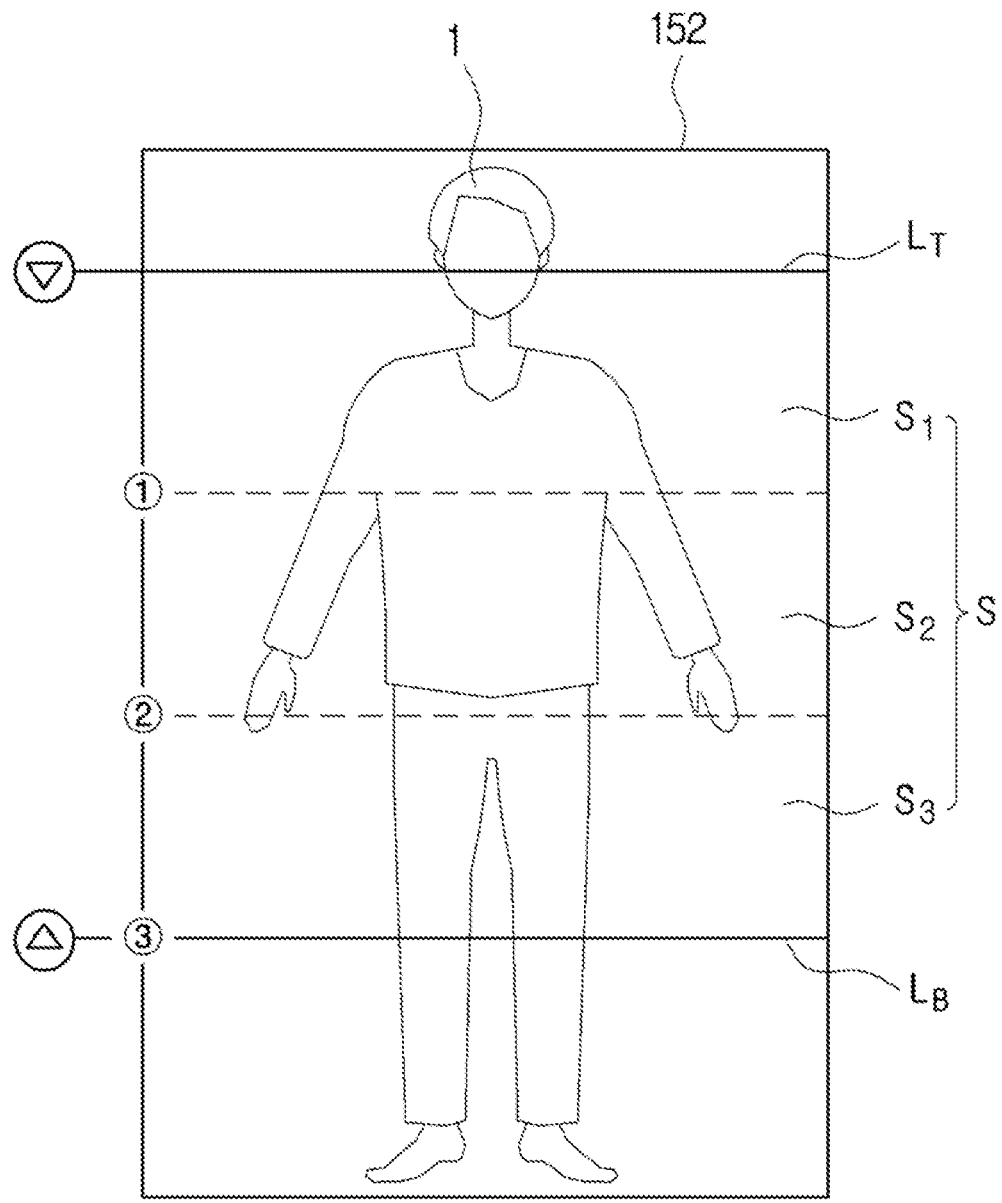
FIG. 28 is a view illustrating an example in which an imaging region is divided to perform stitching imaging.
Figure 29:
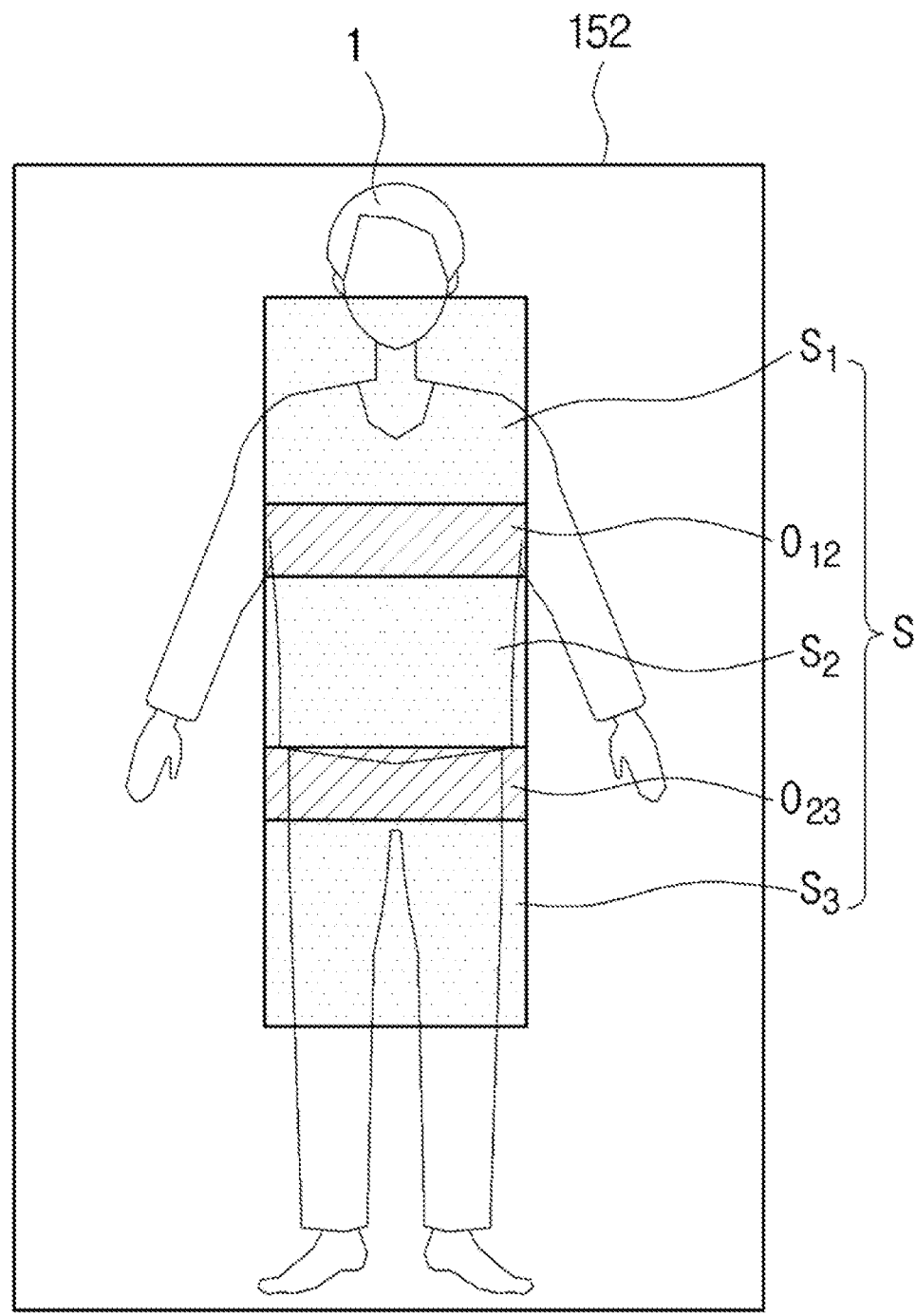
FIG. 29 is a view illustrating overlapping regions between each of a plurality of divided regions.

FIG. 27 is a view illustrating an example of a stitched-together image, FIG. 28 is a view illustrating an example in which an imaging region is divided to perform stitching imaging, and FIG. 29 is a view illustrating overlapping regions between each of a plurality of divided regions.

As illustrated in FIG. 27, the X-ray imaging apparatus 100 may divide an X-ray imaging portion into a plurality of regions and may separately perform X-ray imaging for each of the plurality of divided regions.

The control unit 140 may stitch X-ray images of divided regions, i.e., divided X-ray images $X_1$, $X_2$, and $X_3$, together to generate one stitched-together image $X_{123}$ showing a whole X-ray imaging portion. In this embodiment, an entire region in which stitching imaging is to be performed will be referred to as a stitching region.

As described above, when the selected imaging protocol corresponds to the stitching imaging, the work list 155 may be switched to the camera image 152 illustrated in FIG. 28. Also, an imaging region corresponding to the selected imaging protocol may be automatically designated as the stitching region. The control unit 140 may automatically divide the stitching region. For example, the control unit 140 may divide the stitching region into uniform sizes based on the smaller among height of the detection region and a maximum height of the X-ray irradiation region.

In a detailed example, when a value obtained by dividing a height of a stitching region S, i.e., a distance between a top line $L_T$ showing a point where the stitching region begins and a bottom line $L_B$ showing a point where the stitching region ends, by a height of the region to be detected by the X-ray detector 200 is an integer, the solution may become the number of divided regions, i.e., the number of divided X-ray images, used in stitching imaging. On the other hand, when the value is not an integer, the number of divided regions is larger than the solution by one, and a height of each of the divided regions is smaller than the height of the region to be detected by the X-ray detector 200.

For example, as illustrated in FIG. 28, when the stitching region S is divided into three divided regions $S_1$, $S_2$, and $S_3$, three divided X-ray images respectively corresponding to the divided regions may be captured, and then the three divided X-ray images may be stitched together to generate one stitched-together X-ray image.

Boundary portions between each of the divided X-ray images may be matched to stitch the divided X-ray images together, and X-rays may be radiated so that predetermined regions between the divided X-ray images overlap each other for the matching. When designations of the divided regions are completed, the control unit 140 may control the collimator 113 to radiate X-rays to the divided regions such that X-rays is radiated to a range expanded from a divided region toward adjacent divided regions by a predetermined size.

As an example illustrated in FIG. 29, X-rays may be radiated so that a first-to-second overlapping region $O_{12}$ is disposed between the first divided region $S_1$ and the second divided region $S_2$, and a second-to-third overlapping region $O_{23}$ is disposed between the second divided region $S_2$ and the third divided region $S_3$.

Since the overlapping regions $O_{12}$ and $O_{23}$ are redundantly irradiated with X-rays, when a radiosensitive portion such as a genital organ or the heart is disposed in the overlapping regions, the control unit 140 may move the overlapping regions to other portions to avoid redundantly irradiating the radiosensitive portion with X-rays or may output a warning to the user.

Whether a radiosensitive portion is disposed in the overlapping regions may also be determined by applying image processing such as an object recognition algorithm to the camera image 152. For example, a portion disposed at a central portion of a length from head to toe and from which thighs originate may be determined as a portion at which a genital organ is disposed, and a portion spaced apart 20 cm or less downward from armpit portions or shoulders may be determined as a portion at which the heart is disposed.

Information related to a radiosensitive portion, e.g., information on a position or form thereof, may be pre-stored in the storage unit 170 or may also be added or modified by the user.

When outputting a warning, the warning may be visually output through the display unit 150 or aurally output through a speaker provided in the X-ray imaging apparatus 100. When the warning is visually output, the overlapping regions may be directly displayed on the display unit 150 as illustrated in FIG. 29, or text informing that the overlapping regions are disposed at a radiosensitive portion may be displayed on the display unit 150. Since the information simply needs to be conveyed, a method of outputting a warning is not limited.

The overlapping regions may be distorted in the stitched image and image quality of the overlapping regions in the stitched image may be degraded. Thus, the user may determine whether the overlapping portions are important portions in an X-ray image that need to be protected from degradation of image quality based on the provided information related to the overlapping regions.

Figure 31:
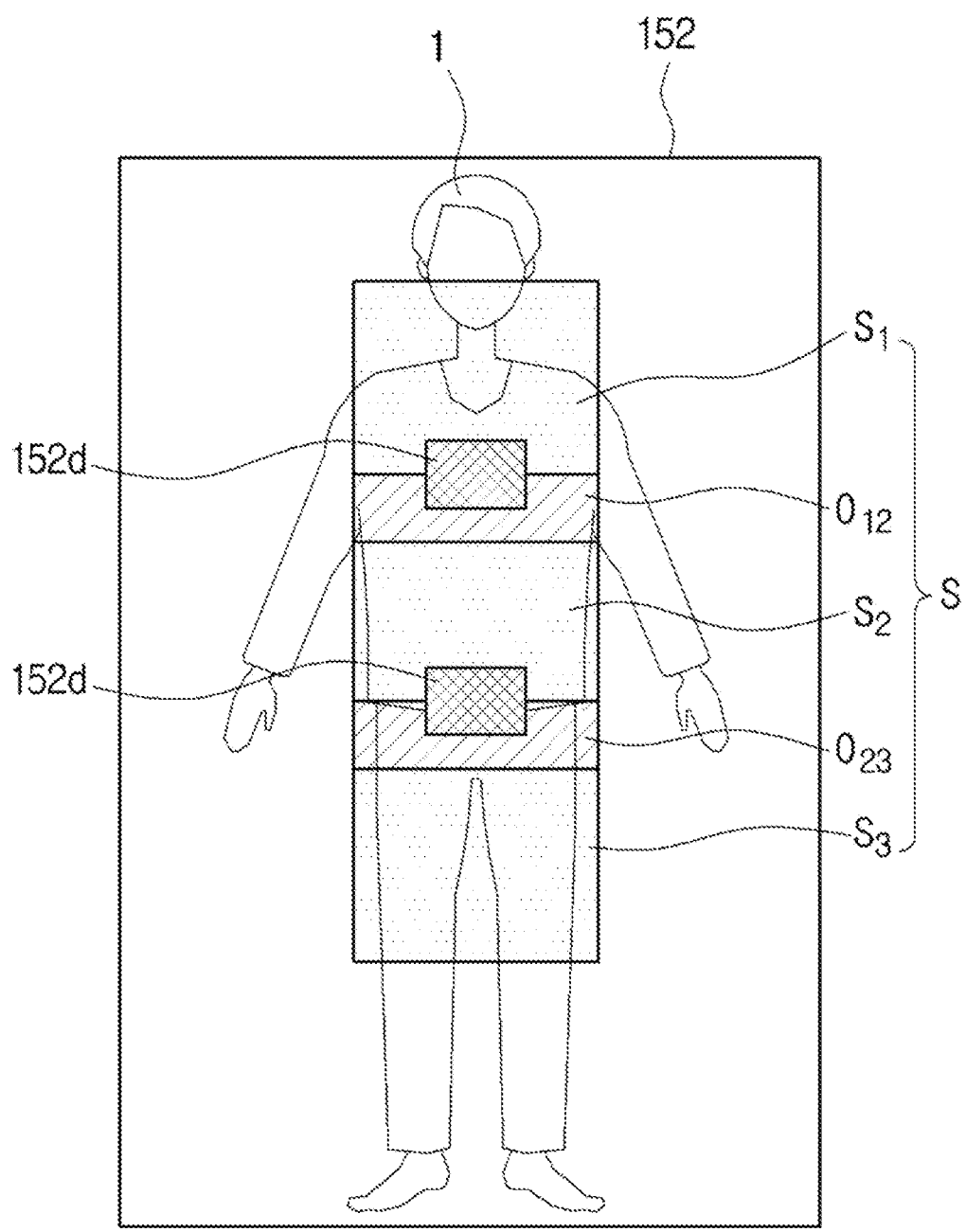

FIGS. 30 and 31 are views illustrating an operation in which overlapping regions are automatically adjusted.

With reference to FIG. 29 described above, a case in which the first-to-second overlapping region $O_{12}$ is disposed at a heart portion and the second-to-third overlapping region $O_{23}$ is disposed at a genital region portion is assumed.

As illustrated in FIG. 30, the control unit 140 may move a lower boundary of the first divided region $S_1$ downward so that the first-to-second overlapping region $O_{12}$ is disposed below the heart portion (①→①') and may move a lower boundary of the second divided region $S_2$ downward so that the second-to-third overlapping region $O_{23}$ is disposed below the genital organ portion (②→②').

Since a start point and an end point of the stitching region S are unchanged, the stitching region S does not change. Consequently, when a size of the first divided region $S_1$ exceeds a size of the region to be detected by the X-ray detector 200 or the maximum height of X-ray irradiation region due to the movement of the lower boundary of the first divided region $S_1$, or when a size of the second divided region $S_2$ exceeds the size of the region to be detected by the X-ray detector 200 or the maximum X-ray irradiation region due to the movement of the lower boundary of the second divided region $S_2$, the first divided region $S_1$ or the second divided region $S_2$ may be further divided or the entire stitching region S may be further divided into smaller regions, and then overlapping regions may be re-controlled.

Alternatively, when a fact that overlapping regions are disposed at radiosensitive portions is output visually or aurally as described above, the overlapping region may also be adjusted by the user. In this case, radiosensitive portions 152d may be displayed on the camera image 152 as illustrated in FIG. 31 to guide the user to reset the overlapping regions by avoiding the radiosensitive portions. For example, the user may move the overlapping regions displayed on the display unit 150 or move boundary lines of a plurality of divided regions to reset the overlapping regions.

Figure 32:
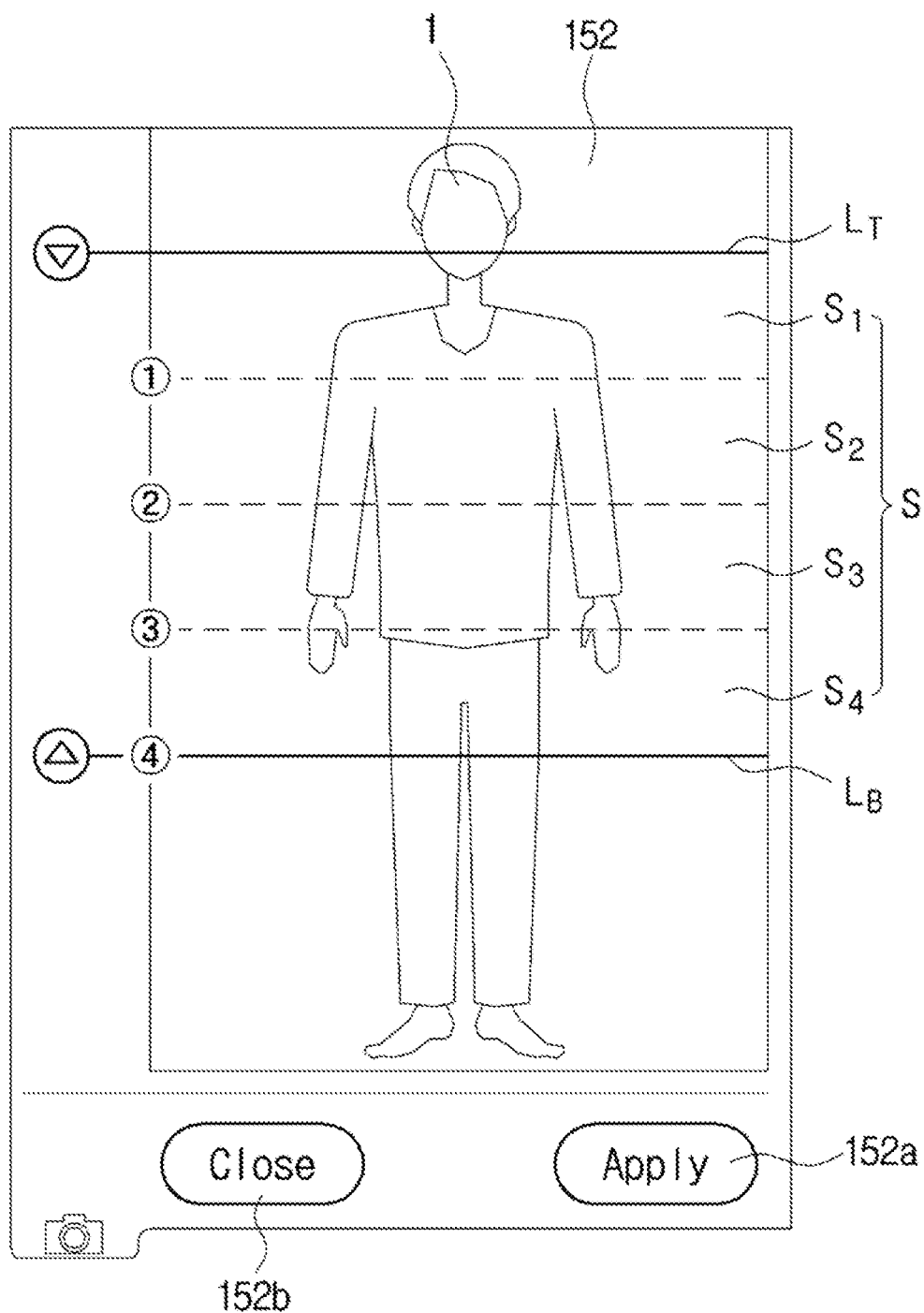
FIGS. 32 and 33 are views related to a case in which a user directly designates a stitching region.
Figure 33:
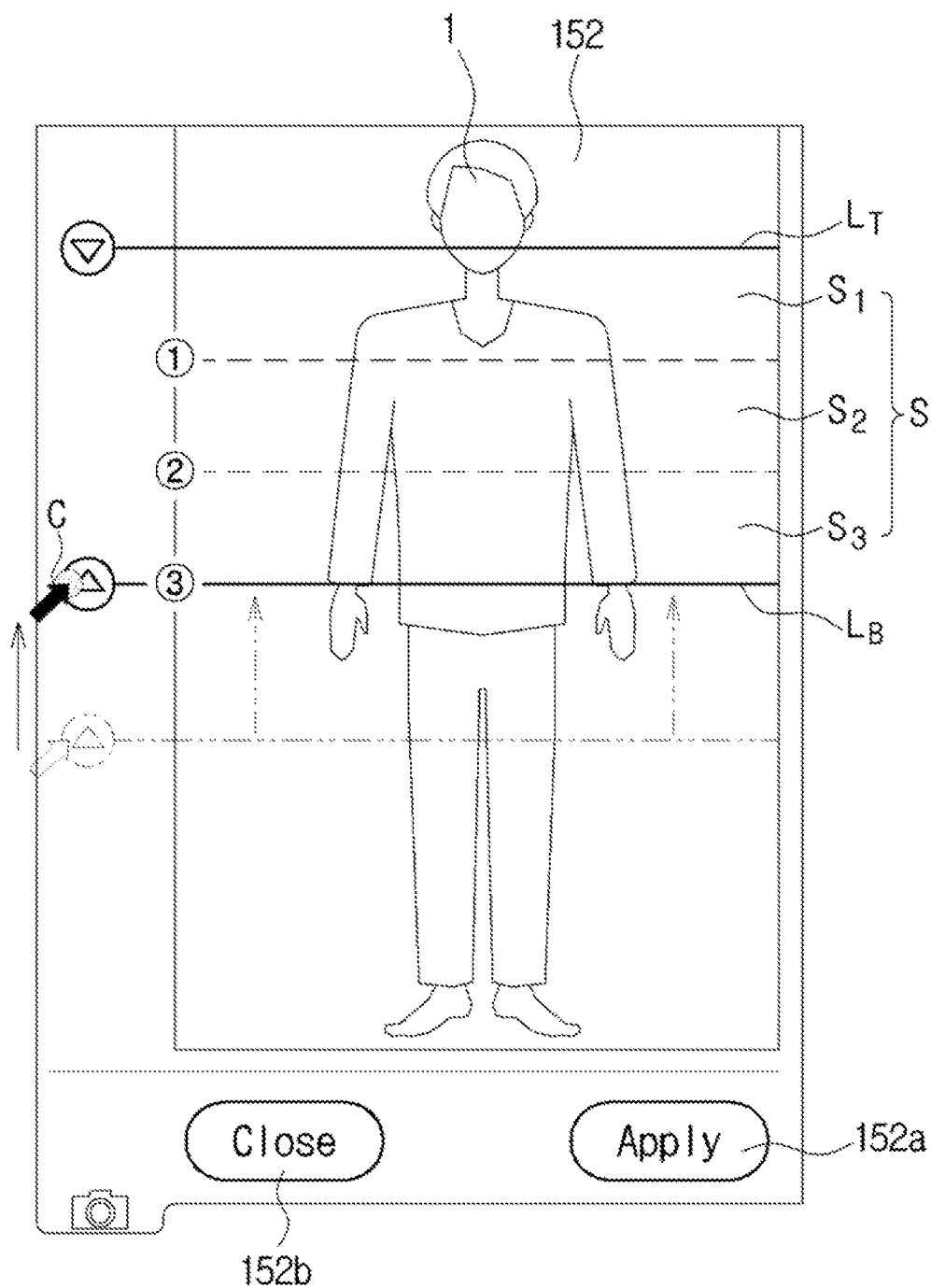

FIGS. 32 and 33 are views related to a case in which a user directly designates a stitching region.

In the example described above, an imaging region that has been mapped to advance is designated as the stitching region S according to a selection of an imaging protocol. However, the stitching region may also be directly designated by the user.

As illustrated in FIGS. 32 and 33, the camera image 152 captured by the capturing unit 120 may be displayed on the display unit 150. On the display unit 150, the top line $L_T$ showing the point where the stitching region begins and the bottom line $L_B$ showing the point where the stitching region ends may be displayed by being overlapped on the camera image 152. By viewing the camera image 152, the user may intuitively recognize the number of divided imaging operations necessary for acquiring a stitched image of the imaging region. In this aspect, the display unit 150 is configured to allow the user to intuitively and conveniently recognize the optimal number of divided imaging operations, thereby preventing excessive X-ray irradiation.

The top line $L_T$ and the bottom line $L_B$ may be initially displayed at any position on the camera image 152 or, when an imaging protocol is selected, may be displayed at positions corresponding to the selected imaging protocol.

When the top line $L_T$ and the bottom line $L_B$ are displayed at any position on the camera image 152, the bottom line $L_B$ may be disposed at a lower end portion of the camera image 152. Since an object's feet are disposed at the lower end portion of the camera image 152 regardless of the size of the object, a work load of the user may be reduced when the bottom line $L_B$ is disposed at the lower end portion of the camera image 152 since the user does not have to manipulate the input unit to move the bottom line $L_B$.

When the top line $L_T$ and the bottom line $L_B$ are displayed at positions corresponding to an imaging protocol, the control unit 140 may perform image processing such as applying an object recognition algorithm to the camera image 152 to recognize a portion corresponding to the imaging protocol.

Alternatively, only one of the top line $L_T$ and the bottom line $L_B$ may be displayed and the other one may be determined by designation of the number of divided imaging.

The user may manipulate the input unit 160 to adjust positions of the top line $L_T$ and the bottom line $L_B$. To guide the manipulation by the user, the display unit 150 may display the cursor C, and the cursor C may move on the screen displayed on the display unit 150 according to the manipulation of the input unit 160 by the user.

In a case in which the input unit 160 is a mouse, a trackball, or a keyboard, when the user input control command for moving the top line $L_T$ and the bottom line $L_B$ by manipulating the mouse, the trackball, or the keyboard, the cursor C moves according to a direction and a movement amount corresponding to the manipulation. In a case in which the input unit 160 is a touch pad, the cursor C moves according to a direction in which the user's finger moves and a movement amount of the user's finger.

For example, the user may drag the top line $L_T$ or the bottom line $L_B$ to move the top line $L_T$ or the bottom line $L_B$ to a desired position as illustrated in FIGS. 32 and 33. The top line $L_T$ and the bottom line $L_B$ may move in a vertical direction or in a longitudinal direction of the object. As described above, the stitching region S may be defined by the top line $L_T$ and the bottom line $L_B$. That is, a region between the top line $L_T$ and the bottom line $L_B$ may be the stitching region S.

Alternatively, when the top line $L_T$ and the bottom line $L_B$ move to a position corresponding to a selected imaging protocol, the user may also re-designate the stitching region with reference to the moved positions of the top line $L_T$ and the bottom line $L_B$.

When the stitching region S is designated, the control unit 140 may automatically divide the stitching region S. The description related to the automatic division of the stitching region S is the same as in the example described above.

The control unit 140 may perform real-time uniform division every time the top line $L_T$ and the bottom line $L_B$ move and show the result. For example, when the stitching region S is divided into four regions $S_1$, $S_2$, $S_3$, and $S_4$ as illustrated in FIG. 32, the regions may be divided using guide lines such as a dotted line, and the guide lines dividing the regions may be numbered from 1 to 4 to provide information on the total number of divided regions and a number assigned to a corresponding region.

The first guideline ① may be a bottom limit for a maximum region for which an X-ray image is to be acquired by performing a single X-ray imaging. The second guideline ② may be a bottom limit for a maximum region for which an X-ray image is to be acquired by performing an X-ray imaging twice. The third guideline ③ may be a bottom limit for a maximum region for which an X-ray image is to be acquired by performing an X-ray imaging three times. The fourth guideline ④ may be a bottom limit for a maximum region for which an X-ray image is to be acquired by performing an X-ray imaging four times.

In addition, when the user has dragged the bottom line $L_B$ toward the top line $L_T$ as illustrated in FIG. 33, the control unit 140 may re-perform the real-time uniform division. When the stitching region S is reduced and divided into three regions $S_1$, $S_2$, and $S_3$, the guide lines dividing the regions may be numbered from 1 to 3 to inform that the stitching region is divided into a total of three regions.

Also, to emphasize that the number of divided imaging has changed, the display unit 150 may display the fourth guideline, so as to be distinguished from the remaining first through third guidelines through ④. For example, the fourth guideline 12-4 may be displayed in different ways to be distinguished from the remaining first through third guidelines ① through ③.

When the designation of the stitching region is completed, the user may select apply button 152*a* and when the apply button 152*a* is selected, the display unit 150 may display divided window W1, W2, W3 on the camera image 152 described below.

In addition, when the control command for moving the top line $L_T$ or the bottom line $L_B$ is input again while the divided window is displayed, the present screen including the divided window may be switched to the previous screen including guide lines so that the stitching region or the divided regions are re-designated.

Also in a case in which the user has directly designated the stitching region S, like the case described above, whether overlapping regions are disposed at radiosensitive portions may be determined, and when it is found that the overlapping regions are disposed at the radiosensitive portions, a warning may be output or the overlapping regions may be automatically controlled. Alternatively, the stitching region S may also be directly divided by the user. Also in this case, like the case described above, whether overlapping regions are disposed at radiosensitive portions may be determined, and when it is found that the overlapping regions are disposed at the radiosensitive portions, a warning may be output or the overlapping regions may be automatically controlled. Also, radiosensitive portions may be displayed on the camera image 152 when the user inputs division of the stitching region S to guide the user's input so that the overlapping regions are not disposed at the corresponding radiosensitive portions.

Although the control unit 140 has been described in the embodiment above as dividing the stitching region S into uniform sizes, an embodiment of the X-ray imaging apparatus 100 is not limited thereto. The size of each of the divided regions may also be adjusted to be different from each other, and the size of each of the divided regions may also be directly set by the user. The user may designate the start point and end point of each divided region. If it is desired to split the whole stitching region S into three divided regions, a start point and an end point of a first divided region $S_1$, a start point and an end point of a second divided region $S_2$, and a start point and an end point of a third divided region $S_3$ may be designated.

If a designation of stitching imaging regions is performed by directly moving a large X-ray source, which may make it difficult for a user to precisely designate the stitching regions and may cause severe fatigue to the user.

According to the above embodiments, the X-ray imaging apparatus may precisely designate stitching regions and may reduce user fatigue.

In addition, repetitive irradiation of an important body part with X-rays may be prevented by adjusting overlapping regions automatically or manually.

FIGS. 34A to 36 are views illustrating a screen that allows a user to set a width of an X-ray irradiation region of each of the plurality of divided regions in the X-ray imaging apparatus according to an embodiment.

Conventionally, a width of a divided region is fixed according to an X-ray irradiation region determined by a collimator. However, since an area occupied by an object is different in each of the divided regions even with respect to a single object, an unnecessarily excessive X-ray exposure may occur when X-ray irradiation regions having the same width are respectively applied to all of the divided regions.

Consequently, the X-ray imaging apparatus 100 according to an embodiment may adjust a width of an X-ray irradiation region for each of the plurality of divided regions. Since the X-ray irradiation region is determined by a collimation region, adjusting the X-ray irradiation region refers to adjusting the collimation region.

Figure 34A:
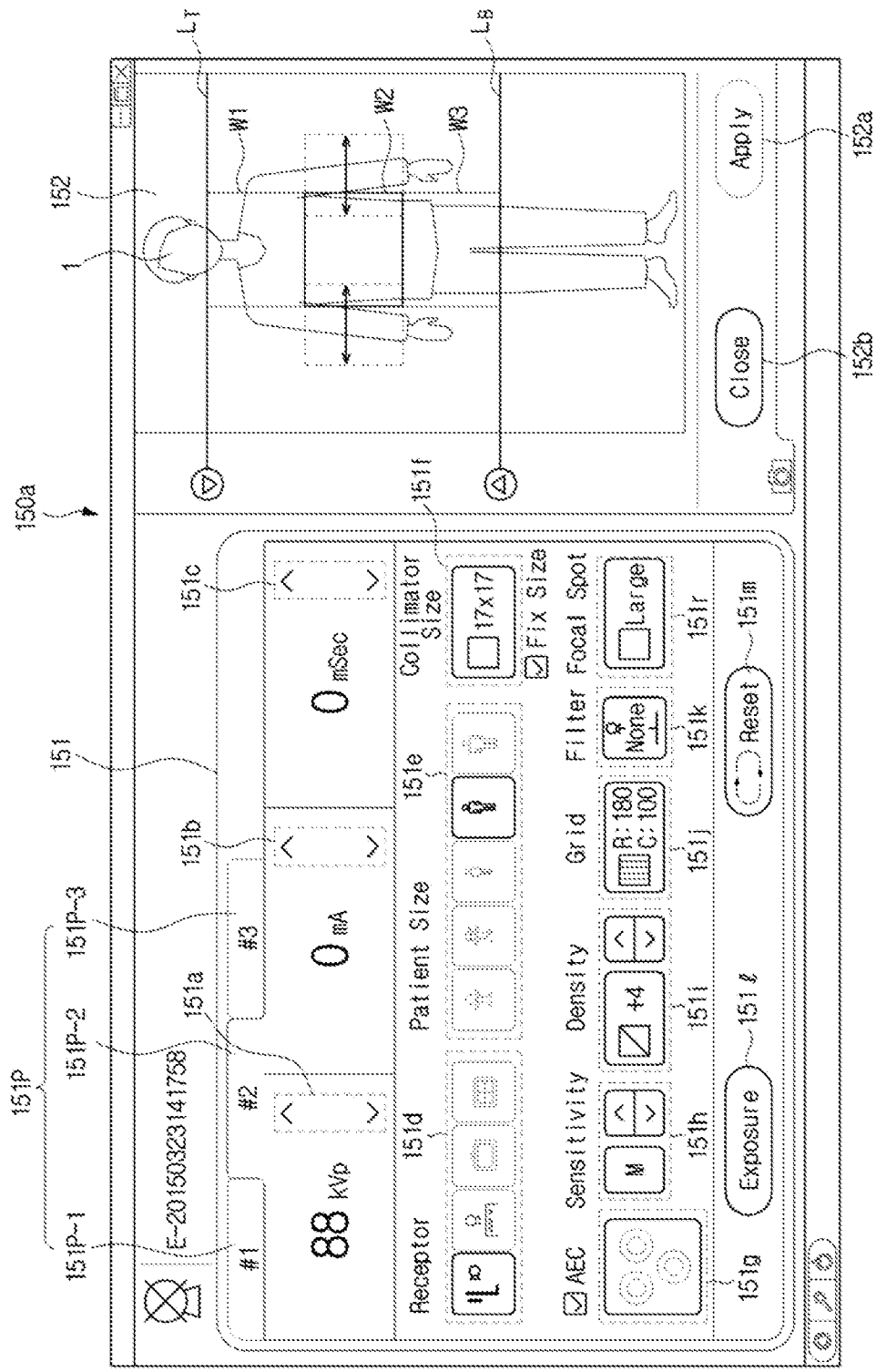
FIGS. 34A, 34B, 35, and 36 are views illustrating a screen that allows a user to set a width of an X-ray irradiation region of each of a plurality of divided regions in the X-ray imaging apparatus according to an embodiment.

As illustrated in FIG. 34A, divided windows W1, W2, and W3 respectively corresponding to the plurality of divided regions may be displayed on the camera image 152. The first divided window W1 corresponds to a first divided region, the second divided window W2 corresponds to a second divided region, and the third divided window W3 corresponds to a third divided region.

Figure 34B:
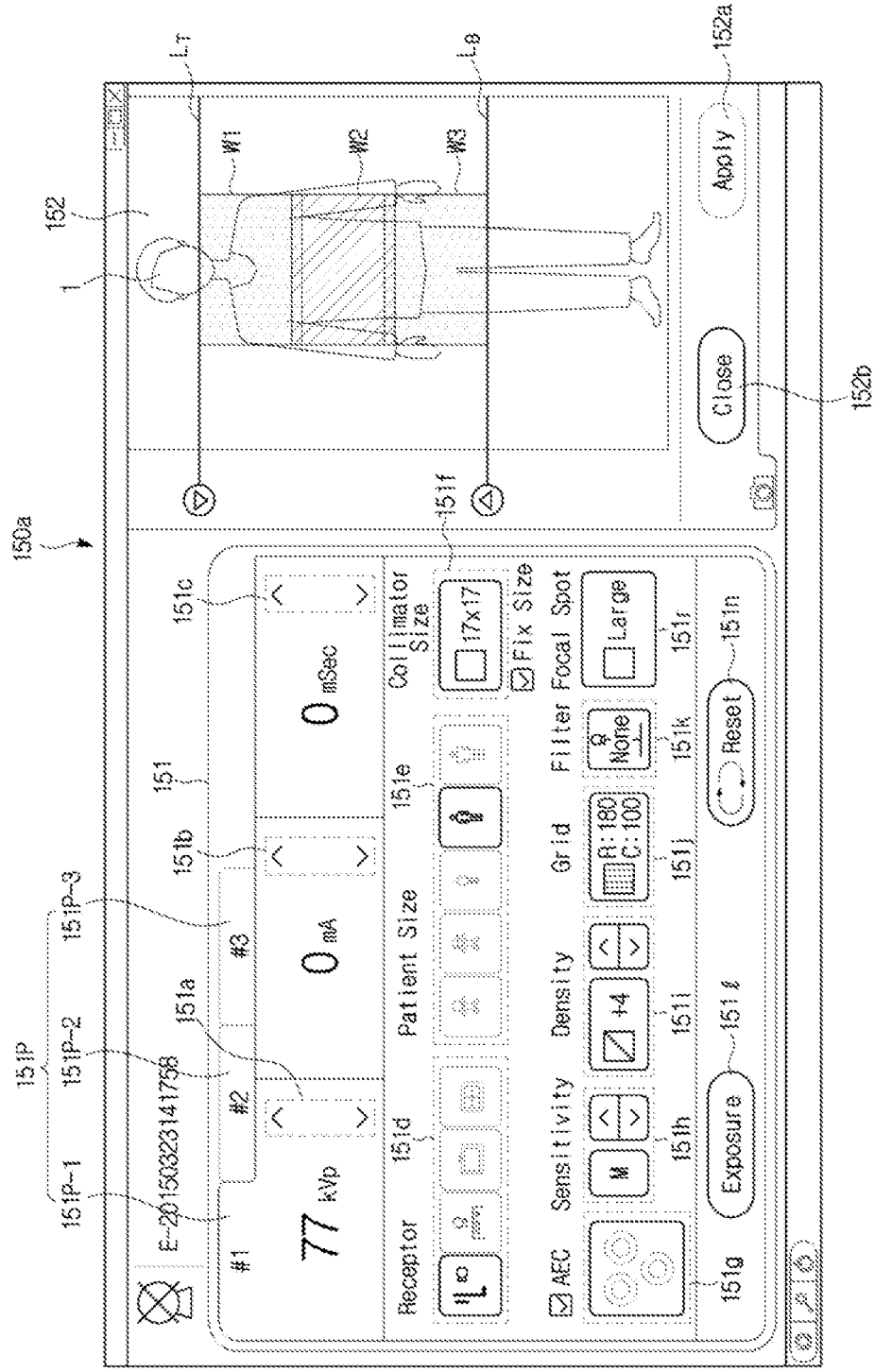

Alternatively, as illustrated in FIG. 34B, the display unit 150 may display the divided windows W1, W2 and W3, adjacent ones of which partially overlap each other, over the camera image 152. The first and second divided windows W1 and W2 may overlap each other to represent overlapping region $O_{12}$ between the first divided region $S_1$ and the second divided region $S_2$, and the second and third divided windows W2 and W3 may overlap each other to represent overlapping region $O_{23}$ between the second divided region $S_2$ and the third divided region $S_3$.

Since the sizes of the divided windows respectively correspond to sizes of the divided regions, widths of the divided regions correspond to the width of the X-ray irradiation region E adjusted by the collimator 113. Heights of the divided regions may be determined according to the control unit 140 or division performed by the user, and the collimator 113 may be automatically adjusted according to the determined heights of the divided regions.

In this embodiment, the widths as well as the heights of the divided regions are adjustable. The user may input a control command for adjusting the widths of the divided regions by horizontally dragging left and right boundaries of the divided windows W1, W2, and W3.

Figure 35:
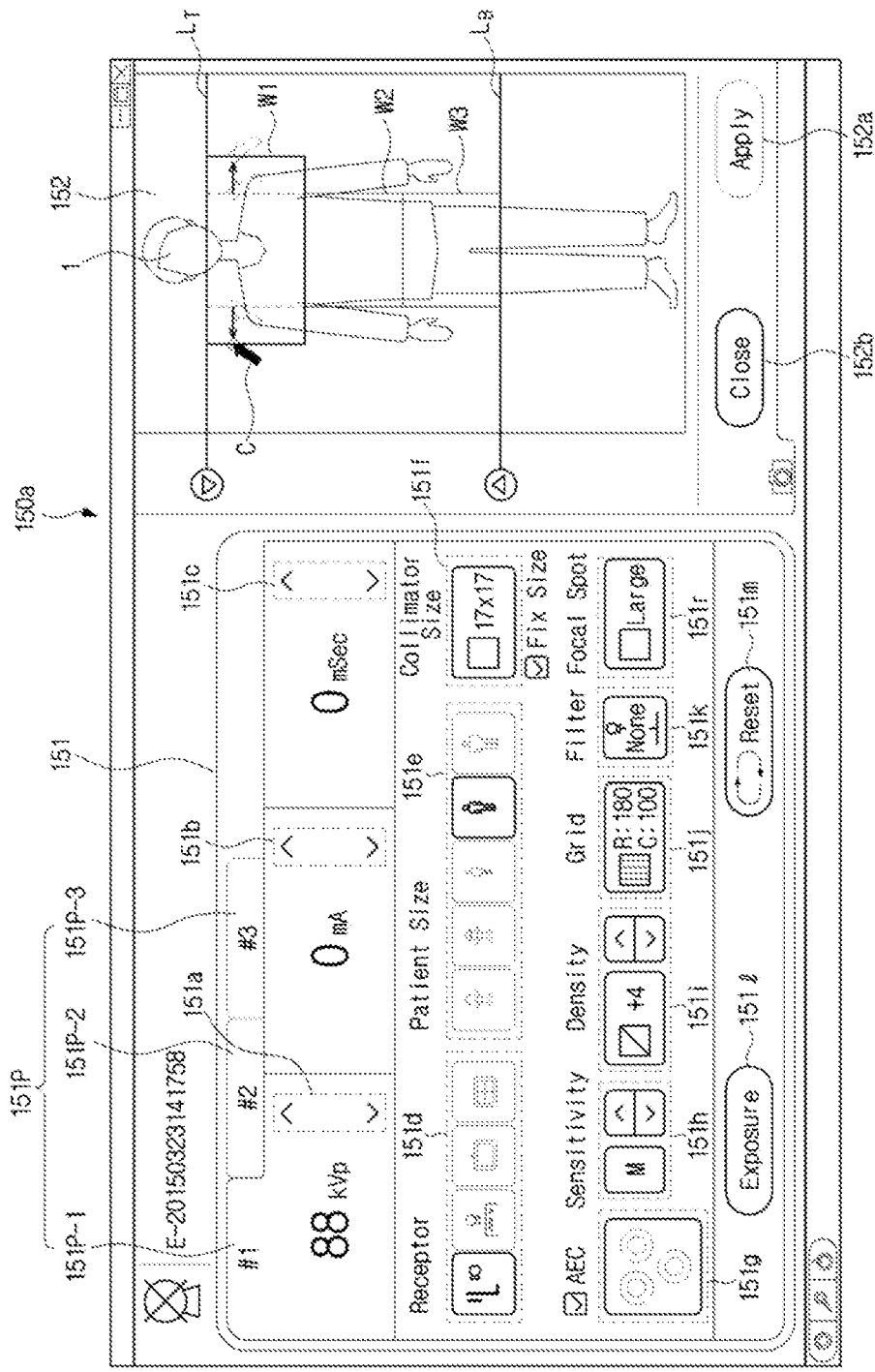

For example, as illustrated in FIG. 35, the left boundary of the second divided window W2 may be dragged leftward and the right boundary thereof may be dragged rightward to extend the width of the X-ray irradiation region so that a whole body is included in the X-ray irradiation region with respect to a divided region corresponding to a body portion of the object.

Figure 36:
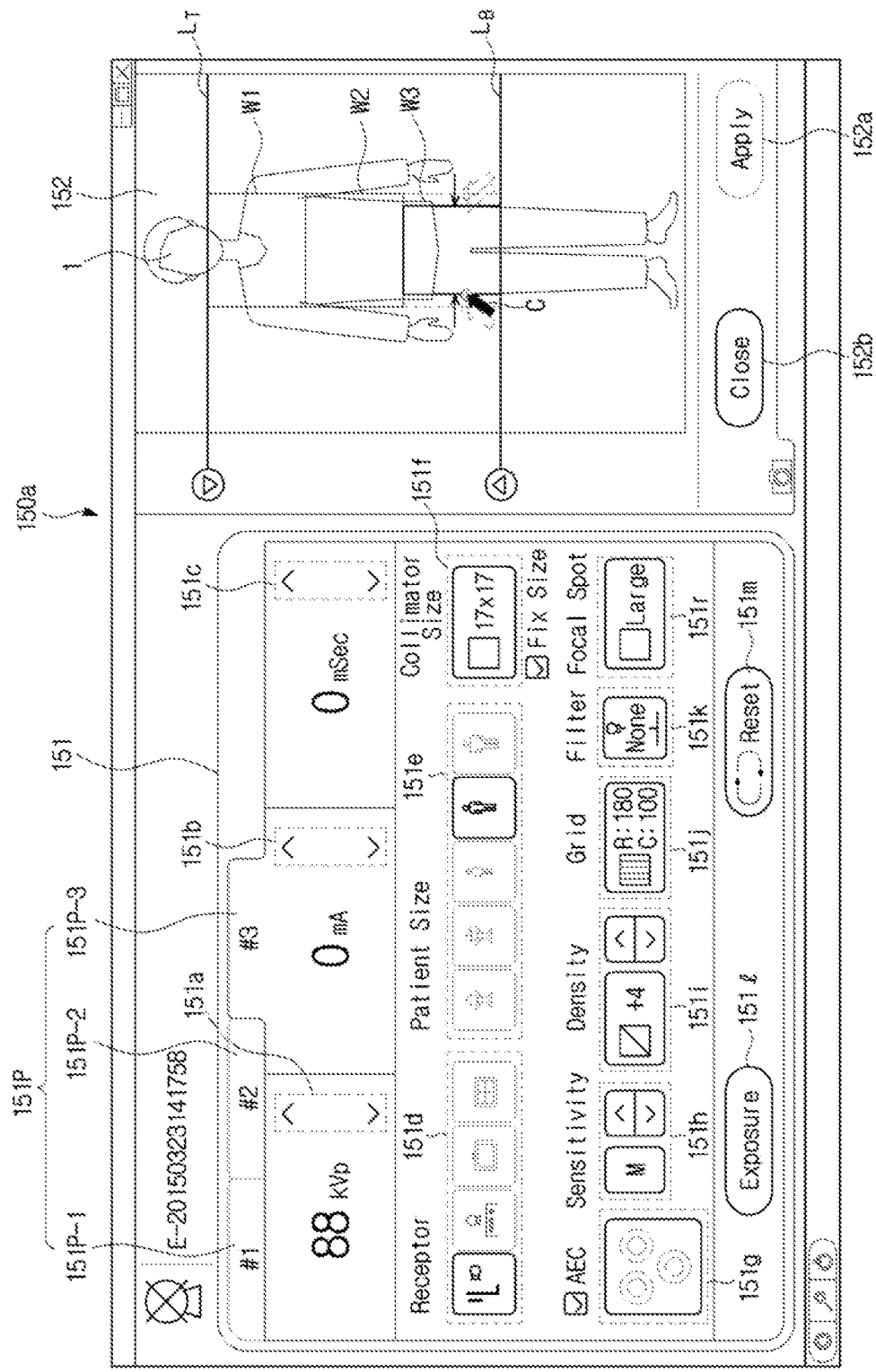

Alternatively, as illustrated in FIG. 36, the left boundary of the third divided window W3 may be dragged rightward and the right boundary thereof may be dragged leftward to reduce the width of the X-ray irradiation region so that a background without legs is excluded from the X-ray irradiation region with respect to a divided region corresponding to a leg portion of the object.

When the setting the width of the X-ray irradiation region for each of the plurality of divided regions is completed, the user may select an apply button 152a, and the storage unit 170 may store information on the set width of the X-ray irradiation region when the apply button 152a is selected.

The GUI through which an X-ray irradiation condition may be set for each of the plurality of divided regions may be displayed on the settings window 151. For example, an identification tab 151p through which a divided region may be identified may be displayed on the upper side of the settings window 151, and identification tags #1, #2, and #3 respectively corresponding to the divided regions may be displayed on identification tabs 151p-1, 151p-2, and 151p-3, respectively. When the user manipulates the input unit 160 and selects one of the identification tabs, a GUI through which an X-ray irradiation condition for the selected divided region may be set may be activated.

The description related to various types of buttons displayed in an activated GUI is the same in the example described above, and thus will be omitted.

A size of a collimator, i.e., the size of the X-ray irradiation region, for each of the plurality of divided regions may also be adjusted using the collimator setting button 151f displayed on the settings window 151. Here, when the size of the collimator is adjusted by selecting the collimator setting button 151f, the camera image 152 displayed at the right side may interoperate therewith, and the widths of the divided windows W1, W2, and W3 may be jointly adjusted therewith.

Conversely, when the width of an X-ray irradiation region is adjusted by horizontally dragging the boundaries of the divided windows W1, W2, and W3 as described above, the collimator setting button 151f may interoperate therewith and change. For example, when the size of the collimator with respect to the first divided region $S_1$ is reduced to 14×17 by dragging the boundary of the divided window W1, the collimator setting button 151f displayed on the settings window 151 may also display the size of 14×17.

Meanwhile, the width of the X-ray irradiation region may also be automatically controlled by the control unit 140. In this case, the control unit 140 may apply image processing such as edge detection to the camera image to extract a silhouette of the object, and may control the width of the X-ray irradiation region based on a boundary between the object silhouette and the background.

For example, the control unit 140 may prevent an unnecessarily excessive X-ray exposure by reducing the width of the X-ray irradiation region when the boundary between the object silhouette and the background is disposed within the currently-shown X-ray irradiation region, and may acquire required information by extending the width of the X-ray irradiation region when the boundary between the object silhouette and the background is disposed outside the currently-shown X-ray irradiation region.

When the setting the size of the X-ray irradiation region and the X-ray irradiation condition for all of the plurality of divided regions is completed, the user may select the exposure button 151l to perform X-ray imaging and may select the reset button 151m when attempting to initialize settings.

Figure 37:
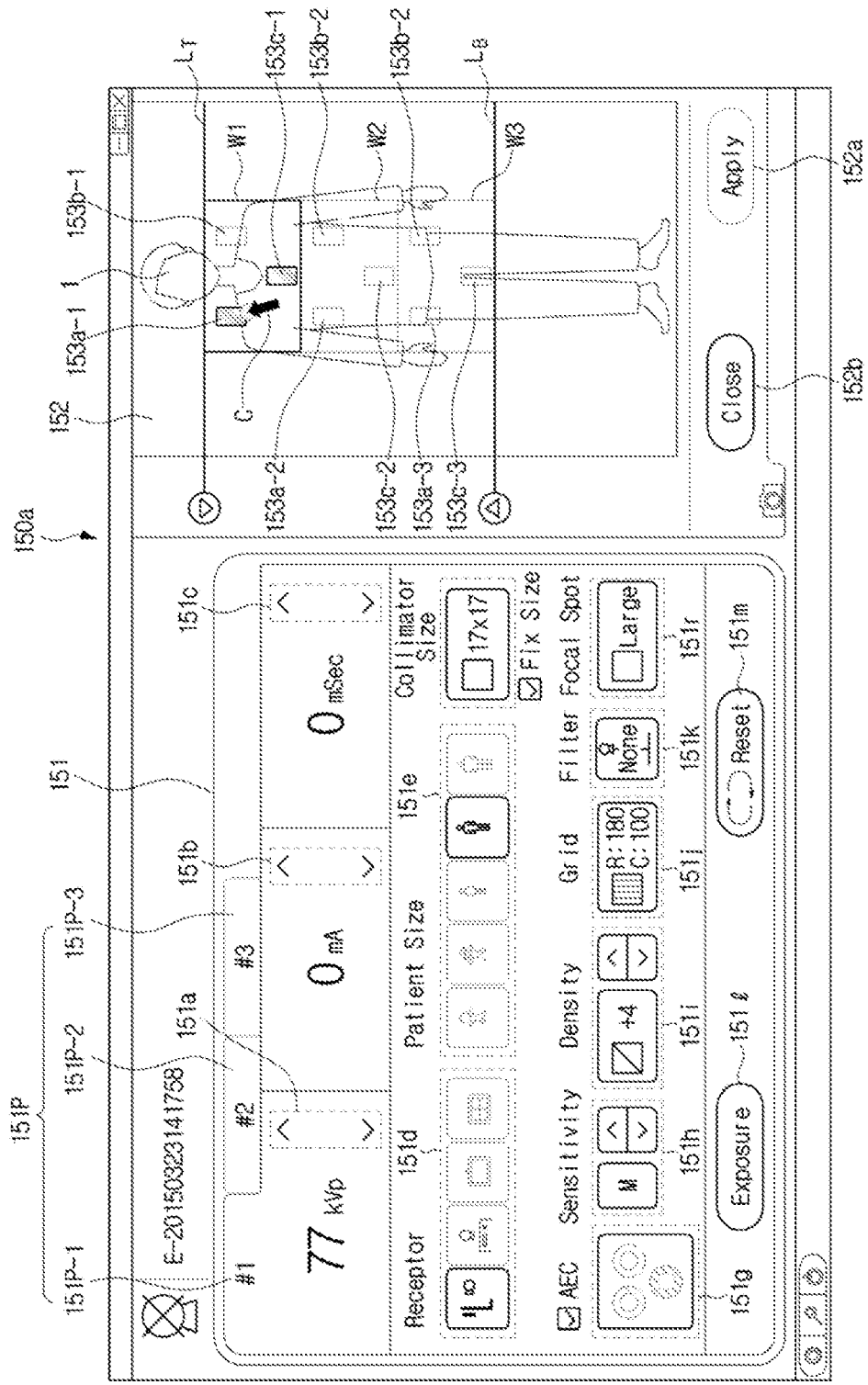
FIGS. 37 and 38 are views illustrating a screen that allows the user to select an AEC sensor in the X-ray imaging apparatus according to an embodiment.
Figure 38:
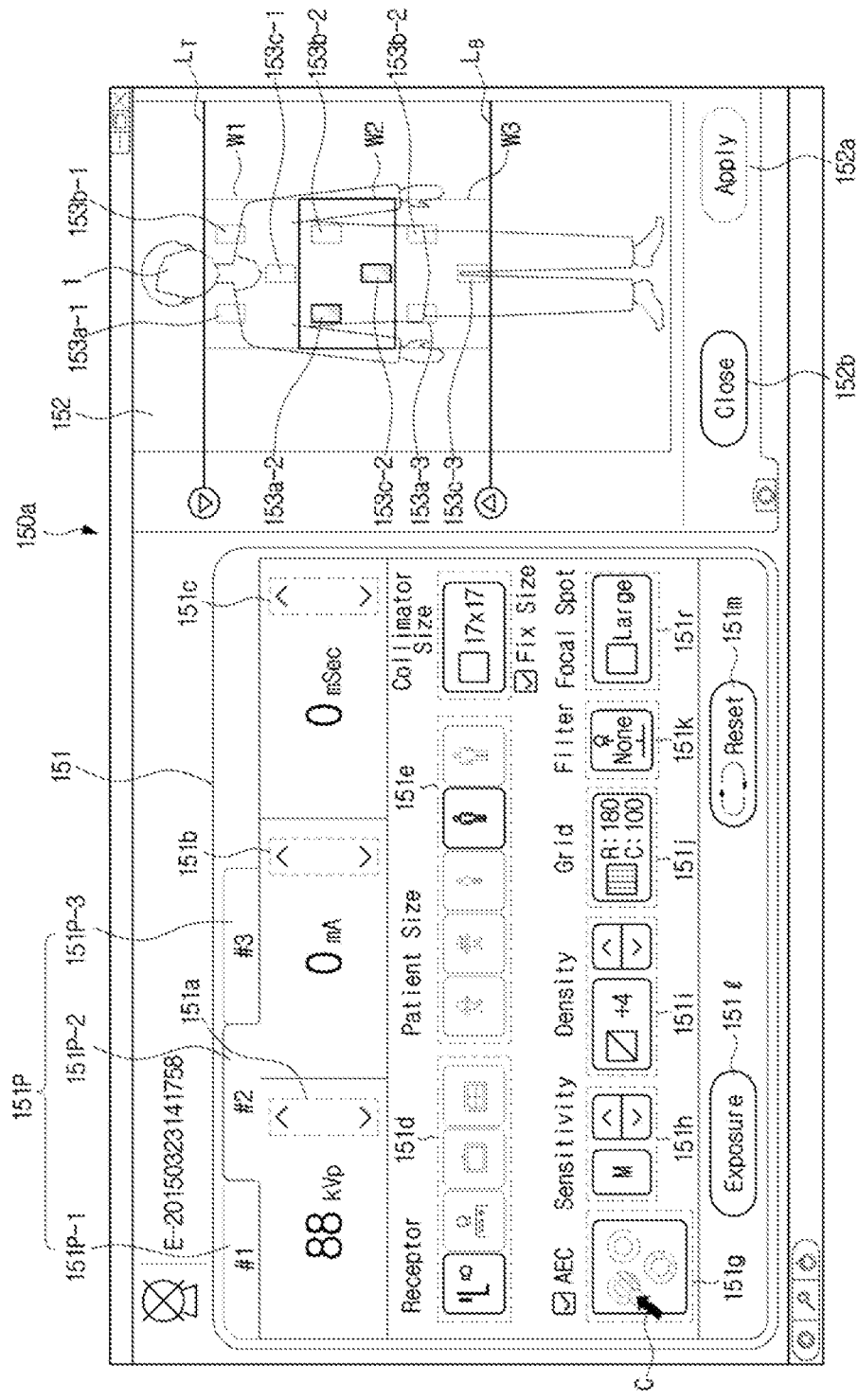

FIGS. 37 and 38 are views illustrating a screen that allows the user to select an AEC sensor in the X-ray imaging apparatus according to an embodiment.

As described above, the plurality of AEC sensors 26a, 26b, and 26c may be used for automatically controlling a dose of X-rays. All or some of the plurality of AEC sensors 26a, 26b, and 26c may be used according to an X-ray imaging portion. Thus, a selection of an AEC sensor may also be performed for each of the plurality of divided regions.

As illustrated in FIG. 37, a plurality of graphical objects respectively showing the plurality of AEC sensors 26a, 26b, and 26c may be displayed within the divided windows W1, W2, and W3. The control unit 140 may perform geometric registration of the camera image 152 by matching each point in the camera image 152 with a position in the actual space. For example, the control unit 140 may use the relationships between camera coordinate system, global coordinate system and image coordinate system.

The control unit 140 may acquire the positions of the AEC sensors 26a, 26b, 26c that correspond to the position of the X-ray detector 200 and coordinate the AEC sensors 26a, 26b, 26c with the camera image 152. The control unit 140 may perform image processing whereby the AEC sensors 26a, 26b, 26c are coordinated with the camera image 152 and the graphical objects that correspond to the AEC sensors are superimposed onto the camera image 152.

For example, the graphical objects may include a plurality of AEC sensor buttons 153a-1, 153b-1, and 153c-1, a plurality of AEC sensor buttons 153a-2, 153b-2, and 153c-2, and a plurality of AEC sensor buttons 153a-3, 153b-3, and 153c-3 respectively corresponding to the plurality of AEC sensors 26a, 26b, and 26c. Each of the AEC sensor buttons may be displayed at a position corresponding to its AEC sensor.

The user may select an AEC sensor to be used for each of the plurality of divided regions. When a button corresponding to an AEC sensor to be used among the plurality of AEC sensor buttons 153a-1, 153b-1, and 153c-1 in the first divided window W1 is selected, the AEC selection button 151g interoperates therewith, and the selection is also reflected and displayed on the AEC selection button 151g of the settings window 151.

Conversely, when a selection of an AEC sensor is input using the AEC selection button 151g of the settings window 151 as illustrated in FIG. 38, the plurality of AEC sensor buttons 153a-2, 153b-2, and 153c-2 interoperate therewith, and the selection is also reflected and displayed on the plurality of AEC sensor buttons 153a-2, 153b-2, and 153c-2.

When the selection of an AEC sensor is input, an AEC sensor button corresponding to the selected AEC sensor may be highlighted by a change in color thereof, darkening or lightening an edge thereof, flickering the AEC sensor button etc. to reflect that the corresponding AEC sensor has been selected. Alternatively, the selected AEC sensor and non-selected AEC sensor may be distinguished from each other by solid line and dotted line. Alternatively, on/off may be displayed as text on the AEC sensor buttons, and when an AEC sensor button with on is selected, the text may change from on to off. When an AEC sensor button with off is selected, the text may change from off to on.

In addition, when a check box above the AEC selection button 151g is selected, the plurality of AEC sensors may be turned on or off The selected AEC sensor may be turned on when an X-ray imaging is performed, and the non-selected AEC sensor may be turned off when an X-ray imaging is performed. However, the reverse may be possible.

When the AEC sensor button displayed on the camera image 152 and the AEC selection button 151g displayed on the settings window 151 interoperate with each other as described above, the user may more intuitively recognize the position of the AEC sensor selected by himself or herself In addition, since the X-ray detector 200 is blocked by the object 1 during X-ray imaging, the user is not able to directly recognize a position of the AEC sensors. According to the exemplary embodiment described above, the display unit 150 may display the AEC sensor buttons over the camera image 152, thereby enabling the user to intuitively and conveniently recognize a relationship between positions of an actual object and AEC sensors.

Furthermore, when the width of an X-ray irradiation region has been adjusted as described above, an AEC sensor may be selected in consideration of the adjusted width of the X-ray irradiation region. For example, when the width of the X-ray irradiation region is narrowed, only some of the AEC sensors may be selected.

Alternatively, an AEC sensor may also be automatically selected by the control unit 140 based on a size of each of the plurality of divided regions or a size of an X-ray irradiation region of each of the divided regions. For example, the control unit 140 may exclude AEC sensors that are disposed outside the X-ray irradiation region or are unnecessary from being selected. Even when the control unit 140 has selected an AEC sensor, the control unit 140 may display which AEC sensor has been selected on the AEC selection button 151g displayed on the settings window 151 and the AEC sensor button in the camera image 152. For example, the control unit 140 may detect a contour or edge of the object 1 in the camera image 152 via image processing such as contour detection or edge detection and turn off the AEC sensor outside the object 1.

If the AEC sensor outside the object 1 is not turned off, the AEC sensor may directly receive X-rays that have not passed through the object 1. This causes the amount of X-rays received by the AEC sensor to quickly exceed a predetermined amount. In this case, the quality of an X-ray image may be degraded due to the lack of X-ray dose irradiated on the object 1.

Thus, the control unit 140 may prevent degradation in quality of an X-ray image by turning off an AEC sensor that is positioned outside the object 1.

When the setting an X-ray irradiation region and an X-ray irradiation condition for each of the plurality of divided regions is completed and the exposure button 151l is selected, the X-ray imaging apparatus 100 may automatically control positions of the X-ray source 110 and the X-ray detector 200 to perform stitching imaging. Hereinafter, this will be described with reference to FIGS. 39A to 39C.

Figure 39A:
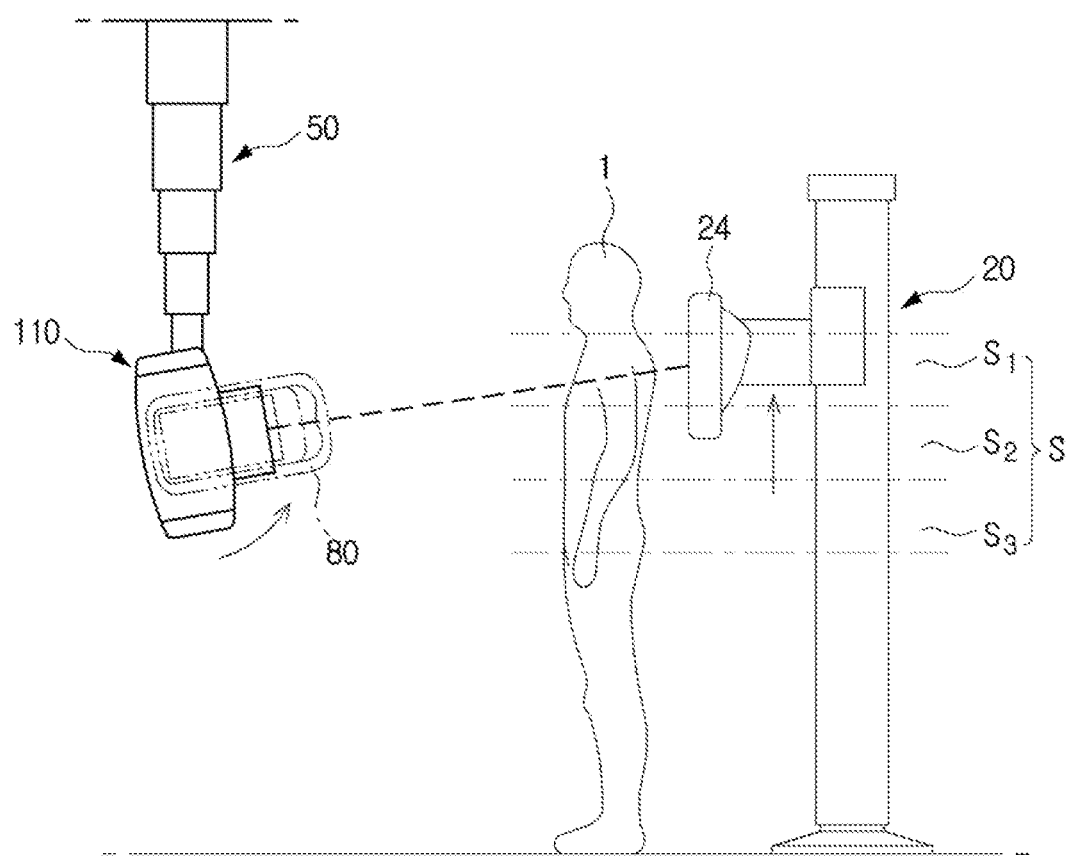
FIGS. 39A, 39B, and 39C are views related to a case in which stitching imaging is performed by controlling a tilt angle of the X-ray source in the X-ray imaging apparatus according to an embodiment.
Figure 39B:
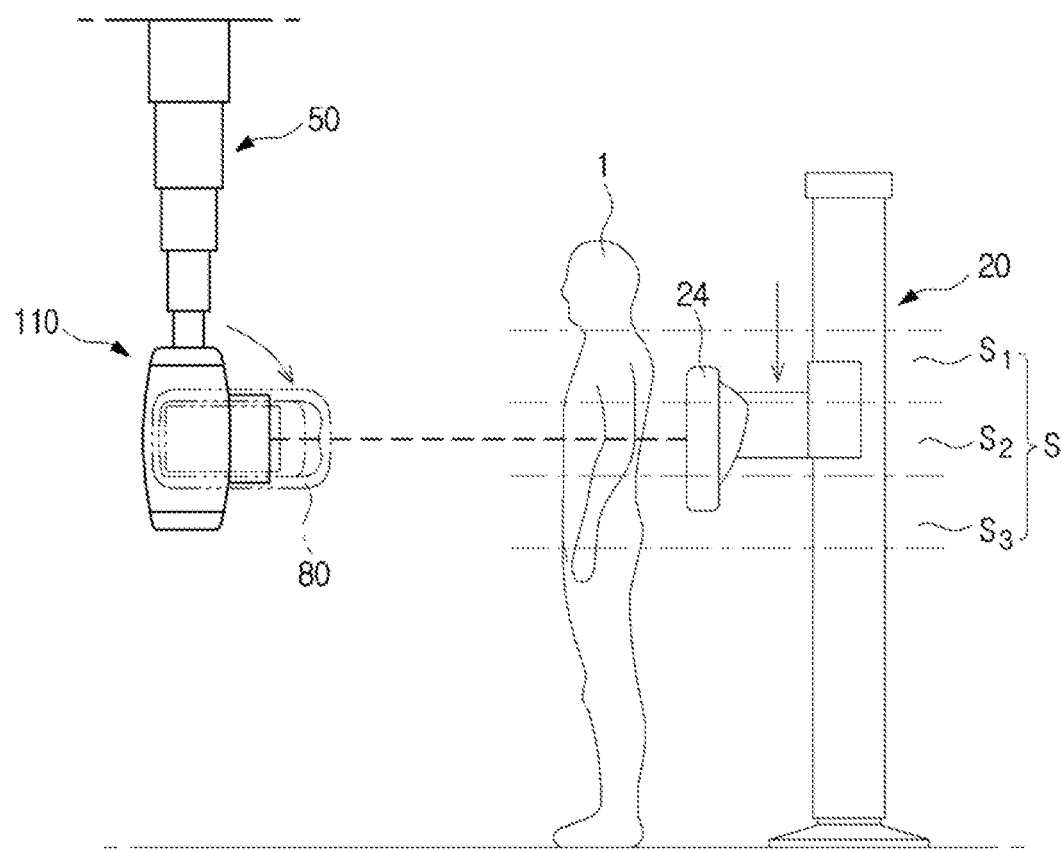
Figure 39C:
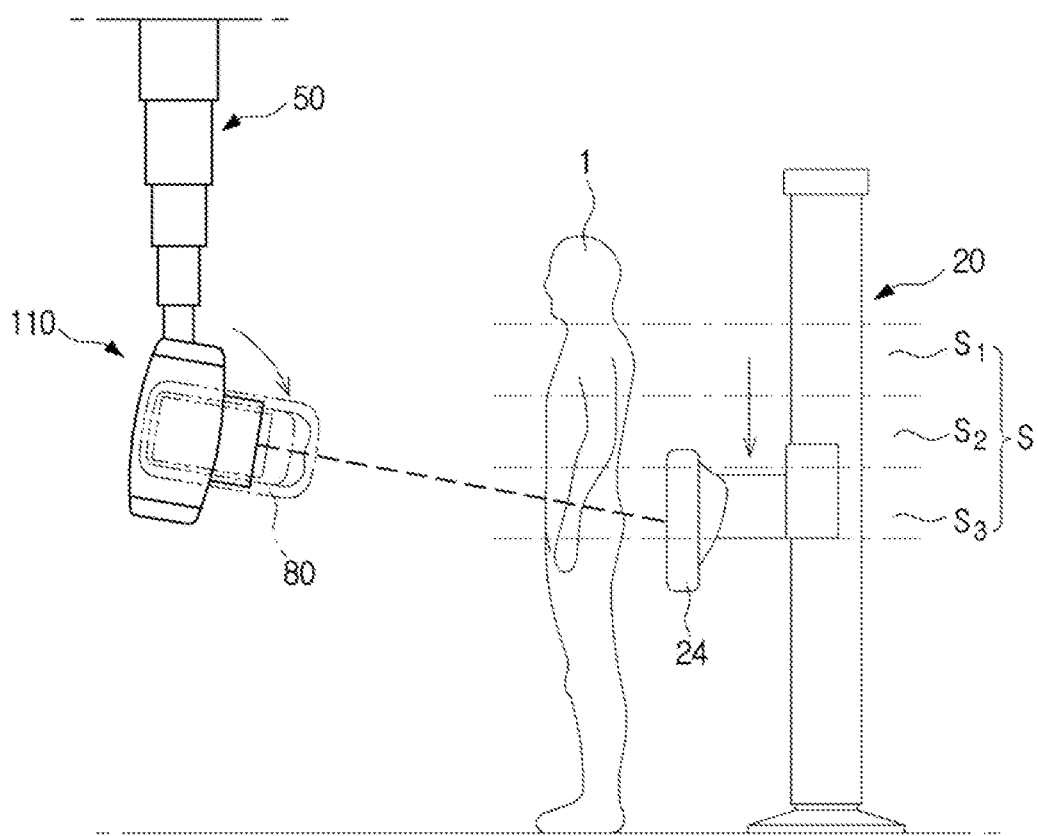

FIGS. 39A to 39C are views related to a case in which stitching imaging is performed by controlling a tilt angle of the X-ray source in the X-ray imaging apparatus according to an embodiment. In this embodiment, a case in which capturing is performed by mounting the X-ray detector 200 on the stand 20 is given as an example.

Before operating the X-ray imaging apparatus 100, calibration may be performed to calculate a location relationship between a camera image obtained through capturing unit 120 and an X-ray image.

For example, when the stitching region S is divided into the three regions $S_1$, $S_2$, and $S_3$, the control unit 140 calculates a first location or a first tilt angle at which the first divided region $S_1$ is irradiated with X-rays, a second location or a second tilt angle at which the second divided region $S_2$ is irradiated with X-rays, and a third location or a third tilt angle at which the third divided region $S_3$ is irradiated with X-rays, based on the previous calibration result.

Prior to performing stitching imaging, it may be assumed that the X-ray source 110 has been moved to a position corresponding to the X-ray detector 200. For example, when both the stand 20 and the table 10 are present in an examination room and the user has selected the stand 20, the control unit 140 may move the X-ray source 110 to a position corresponding to the stand 20. The position of the X-ray source 110 corresponding to the stand 20 may be pre-stored.

Alternatively, the X-ray source 110 may also be manually moved by the user to the position corresponding to the stand 20.

A tilt angle of the X-ray source 110 may be adjusted to an angle corresponding to the first divided region $S_1$ as illustrated in FIG. 39A to capture the first divided X-ray image, the tilt angle of the X-ray source 110 may be adjusted to an angle corresponding to the second divided region $S_2$ as illustrated in FIG. 39B to capture the second divided X-ray image, and the tilt angle of the X-ray source 110 may be adjusted to an angle corresponding to the third divided region $S_3$ as illustrated in FIG. 39C to capture the third divided X-ray image. Here, a height of the X-ray source 110 from the ground may be fixed.

The control unit 140 may transmit a control signal to a motor that adjusts the tilt angle of the X-ray source 110 to adjust the tilt angle of the X-ray source 110 to the angle corresponding to each of the divided regions.

In addition, the control unit 140 may control the collimator 113 to correspond to sizes of the X-ray irradiation region of the first divided region, the second divided region, and the third divided region. For example, positions of the second blade 113b and the fourth blade 113d may be fixed when the stitching region is divided into uniform sizes and heights of the divided regions are the same, and positions of the first blade 113a and the third blade 113c may also be controlled when widths of the divided regions or widths of the X-ray irradiation regions are set to be different from each other.

When a width of an X-ray irradiation region is extended more than a default value, the first blade 113a may be moved in a +x-axis direction, and the third blade 113c may be moved in a −x-axis direction.

In addition, when X-ray irradiation conditions of the first divided region, the second divided region, and the third divided region are set to be different from each other, the X-ray source 110 or the X-ray detector 200 may be controlled to correspond to a set irradiation condition when each of the divided regions is being captured.

In another example, the height of the X-ray source 110 may also be adjusted to a height corresponding to the first divided region $S_1$ to capture the first divided X-ray image, adjusted to a height corresponding to the second divided region $S_2$ to capture the second divided X-ray image, and adjusted to a height corresponding to the third divided region $S_3$ to capture the third divided X-ray image. Here, the tilt angle of the X-ray source 110 may be fixed.

In yet another example, the height and the tilt angle of the X-ray source 110 may also be simultaneously adjusted.

In both of the examples, the X-ray detector 200 is moved to a position corresponding to each of the divided regions. To move the X-ray detector 200, the control unit 140 may move the mounting unit 24 on which the X-ray detector 200 is mounted to a position corresponding to each of the divided regions.

When each of the divided regions is designated, the control unit 140 may calculate an actual position of the X-ray detector 200 to match the center of the designated divided region and the center of the X-ray detector 200. Also, as described regarding FIGS. 11-15, aligning the X-ray source 110 and the X-ray detector 200 may be performed.

Meanwhile, in a case of stitching imaging, since a plurality of X-ray images which will be stitched together into one image are separately captured, image quality of an X-ray image is degraded when an object moves between each of time points at which divided imaging is performed. Consequently, when performing stitching imaging, an orientation of the object has to be controlled between each of the time points at which divided imaging is performed. Hereinafter, this will be described in detail.

Figure 40:
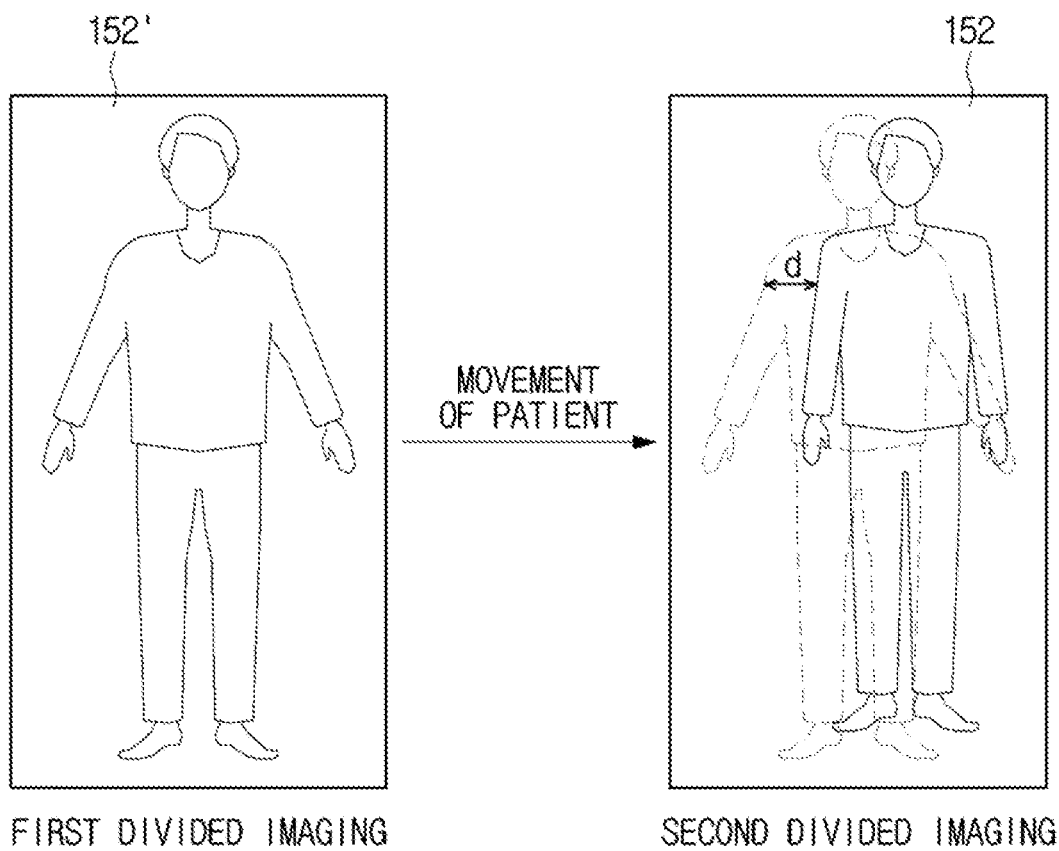
FIG. 40 is a view illustrating an operation of determining a movement of an object using a camera image.
Figure 41:
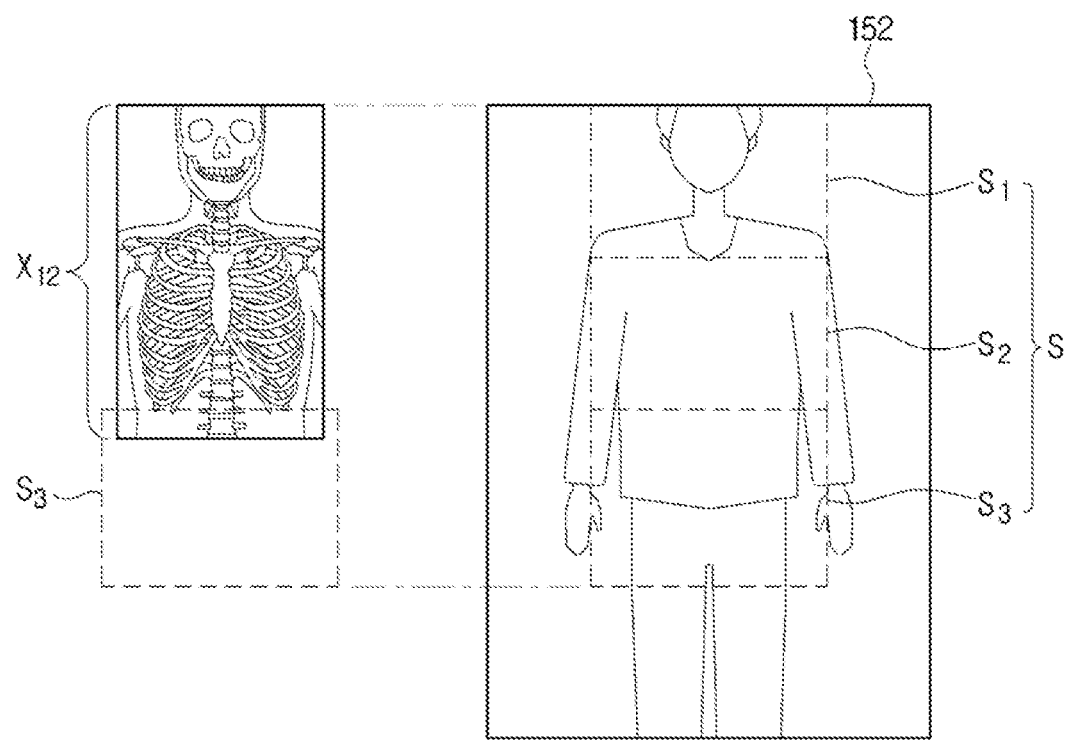
FIGS. 41 and 42 are views illustrating controlling in a case in which re-imaging is performed after stitching imaging is stopped while divided imaging is partially completed.
Figure 42:
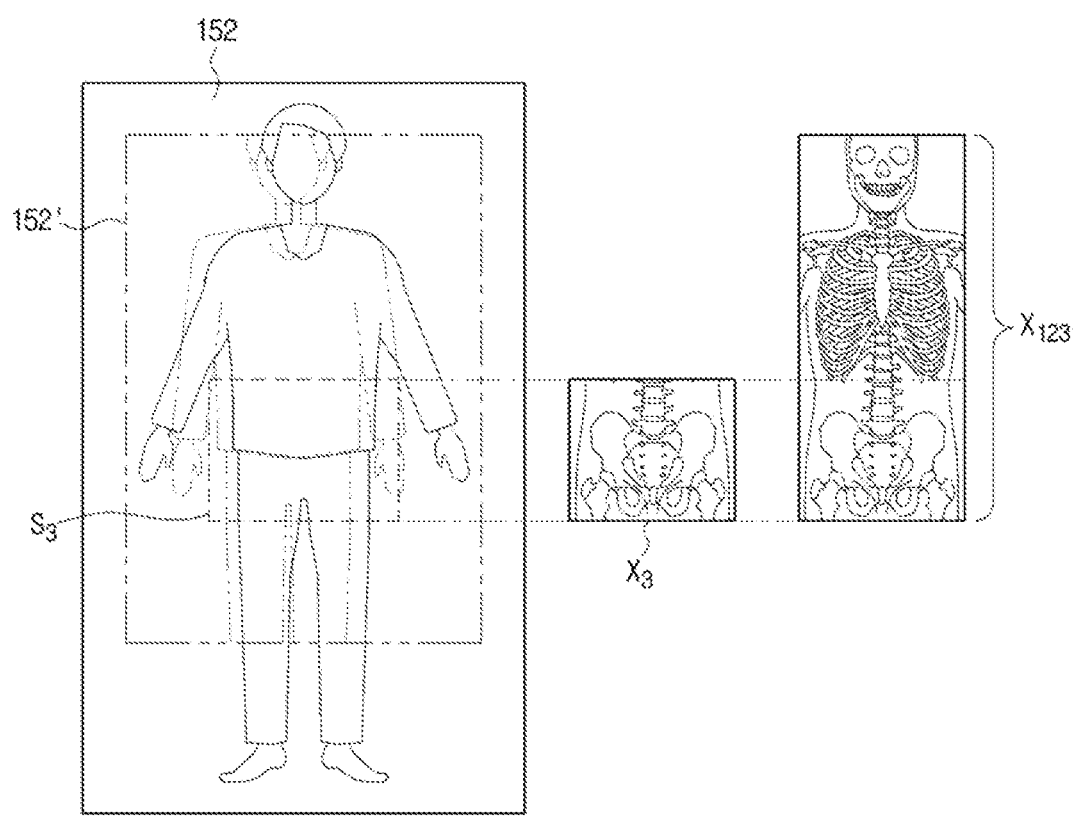

FIG. 40 is a view illustrating an operation of determining a movement of an object using a camera image, and FIGS. 41 and 42 are views illustrating controlling in a case in which re-imaging is performed after stitching imaging is stopped while divided imaging is partially completed.

Even while divided imaging is being performed, the capturing unit 120 may capture a camera image, and the captured camera image may be transmitted to the control unit 140 in real-time. In addition, the captured camera image may be displayed on the display unit 150 in real-time.

In addition, the captured camera image may be stored in the storage unit 170. In this case, the stored camera image may be stored until an omission command is input by the user, and an oldest image may be automatically omitted when a preset amount of time has passed or a preset storage capacity is exceeded.

As illustrated in FIG. 40, the control unit 140 may compare a camera image 152' corresponding to a time point at which a previous divided X-ray image is captured with the current camera image 152 to detect a movement of the object shown in the two images. In this example, the previous divided X-ray image is the second divided X-ray image, and the image to be currently captured is the third divided X-ray image.

For example, the movement of the object may be detected by analyzing a difference d between the two images. The movement may be detected by comparing an orientation of the object shown in the camera image when the second divided imaging is performed and an orientation of the object shown in the current camera image.

When the detected movement has a value equal to or greater than a preset reference value, it may be determined that matching the first divided X-ray image and the second divided X-ray image is impossible even when the third divided X-ray image is captured. Consequently, the control unit 140 may visually or aurally warn of a situation in which matching is impossible or automatically stop stitching imaging.

When the movement of the object has a value equal to or greater than the reference value as described above or a condition of the object is unstable or critical, imaging may be stopped while divided imaging is partially completed.

For example, as illustrated in FIG. 41, after the first divided X-ray image $X_1$ and the second divided X-ray image $X_2$ are captured, imaging may be stopped before X-ray imaging of the third divided region $S_3$ is performed. Although it is illustrated in this example that the first divided X-ray image $X_1$ and the second divided X-ray image $X_2$ are stitched together in advance and a stitched-together image $X_{12}$ of the first divided region and the second divided region is generated, the first divided X-ray image $X_1$, the second divided X-ray image $X_2$, and the third divided X-ray image $X_3$ may also be stitched together at one time after the third divided X-ray image is acquired.

The first divided X-ray image $X_1$ and the second divided X-ray image $X_2$ and the camera images captured during the first divided imaging or the second divided imaging may be stored together in the storage unit 170. Information on divided regions for stitching imaging may also be stored in the camera images. The identification tags may be stored together so that the stored divided X-ray images or camera images may be loaded when stitching imaging is resumed later, and the identification tags may include information capable of classifying studies. The information capable of classifying studies may be one of an object name, a date/capturing time, an imaging protocol, and a combination thereof, or information set by the user regardless of the above.

When the same stitching imaging is resumed after the stitching imaging is stopped, the control unit 140 may search for and load a camera image stored in the storage unit 170. For this, the user may input an identification tag corresponding to stitching imaging to be currently resumed.

As illustrated in FIG. 42, the current camera image may be displayed on the display unit 150, and a camera image loaded from the storage unit 170, i.e., a camera image captured at a time point at which previous divided imaging was performed, may be displayed by being overlapped on the current camera image.

According to this example, the camera image 152' captured during the second divided imaging may be displayed by being overlapped on the current camera image, and the user may guide the orientation of the object with reference to the overlapped camera images. Since the two images overlap each other, the user may accurately recognize a difference between orientations of the object shown in the two images and guide the current orientation of the object to match the orientation of the object during the second divided imaging.

When the orientation of the object matches the orientation of the object during previous divided imaging according to the user's guide, i.e., when the current orientation of the object matches the orientation of the object during the second divided imaging, third divided imaging may be performed. Here, whether the orientations of the object match may be determined with the naked eye by the user or may also be determined by the control unit 140 according to the standard for detecting a movement described above. For example, it may be determined that the orientations match when an object silhouette in the previous camera image 152' and an object silhouette in the current camera image 152 match. In addition, the fact that the orientation during the previous divided imaging matches the current orientation may be output visually or aurally such that the user may select the exposure button, or the divided imaging may also be automatically performed by the control unit 140.

The third divided X-ray image $X_3$ may be acquired when the third divided imaging is performed. The control unit 140 may load the first divided X-ray image $X_1$ and the second divided X-ray image $X_2$ or a stitched-together image $X_{12}$ in which the two X-ray images are stitched together stored in the storage unit 170 to perform stitching with the third divided X-ray image $X_3$ to generate the stitched-together image $X_{123}$ of the entire stitching region S.

Alternatively, even in a case other than the case in which stitching imaging is stopped and resumed, the orientation of the object may be guided by overlapping the camera image acquired during previous divided imaging on the current camera image.

For example, when it is impossible to perform a subsequent divided imaging due to a large movement amount of a patient as described above, an orientation of an object may be guided by overlapping the camera image 152' acquired during a previous divided imaging on the current camera image 152.

Hereinafter, a method for controlling an X-ray imaging apparatus according to an embodiment will be described.

The X-ray imaging apparatus 100 described above may be used in the method for controlling an X-ray imaging apparatus according to an embodiment. Consequently, the descriptions given above may also be identically applied to the method for controlling an X-ray imaging apparatus.

Figure 43:
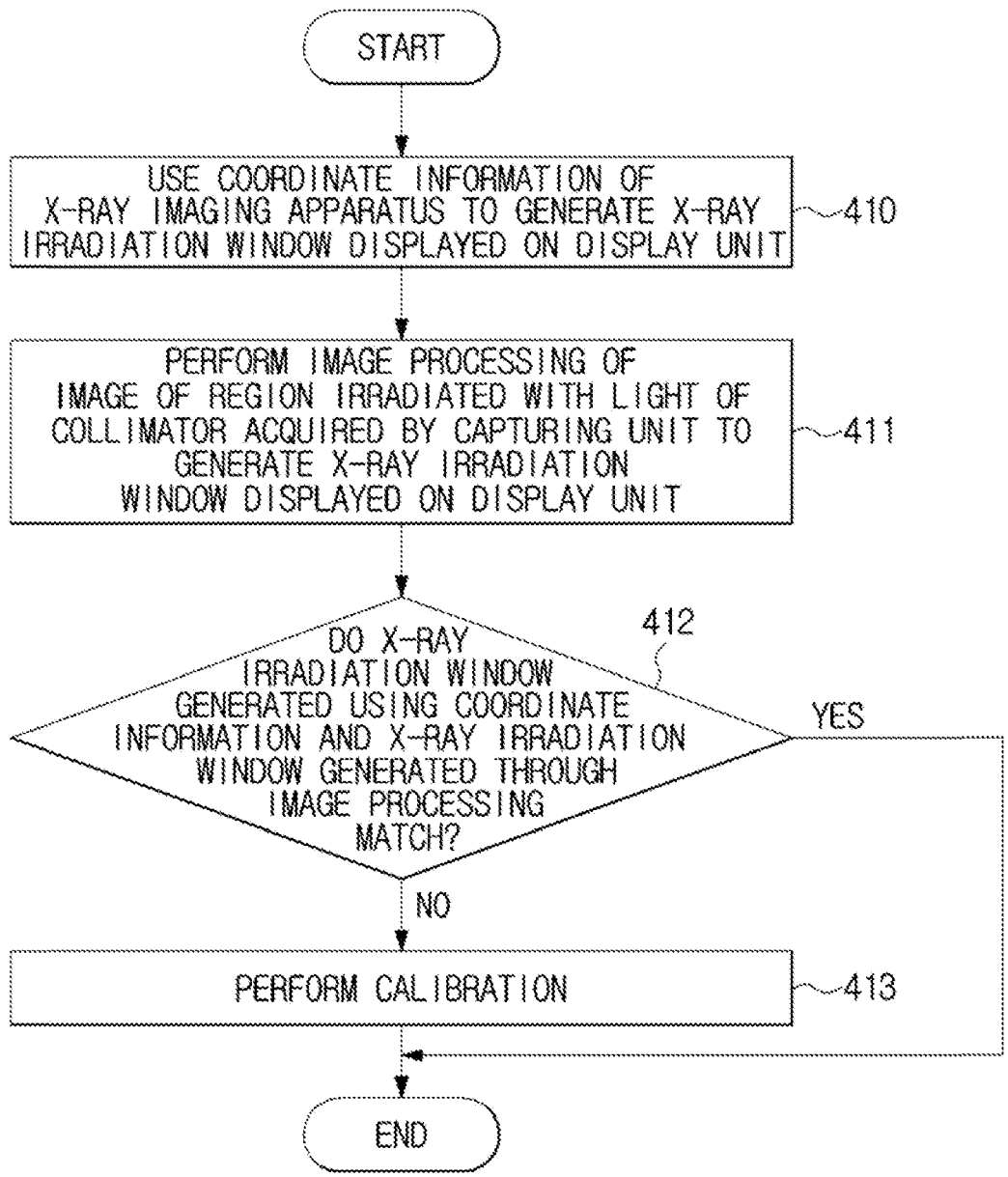
FIG. 43 is a flowchart illustrating an example of a method for verifying an X-ray irradiation region in a method for controlling an X-ray imaging apparatus according to an embodiment.

FIG. 43 is a flowchart illustrating an example of a method for verifying an X-ray irradiation region in a method for controlling an X-ray imaging apparatus according to an embodiment.

Referring to FIG. 43, the control unit 140 uses coordinate information of the X-ray imaging apparatus 100 to generate an X-ray irradiation window displayed on the display unit 150 (410). The control unit 140 may use pre-stored coordinate information of the X-ray imaging apparatus 100 to acquire information on a position and size of the X-ray irradiation window.

The control unit 140 may include pre-stored pieces of information on a distance between the X-ray source 110 and the X-ray detector 200, a form and an area of the slot R to be irradiated with X-rays formed by the collimator 113, a distance from the X-ray tube 111 to the slot R, etc., or may calculate the above pieces of information from pre-stored information.

The control unit 140 may use the above pieces of information to calculate three-dimensional coordinates of the X-ray irradiation region E formed at the X-ray detector 200. The three-dimensional coordinates of the X-ray irradiation region E calculated by the control unit 140 corresponds to coordinates on a global coordinate system of a space in which the X-ray imaging apparatus 100 is disposed.

Since the X-ray irradiation window B1 is displayed by being overlapped on a camera image acquired by the capturing unit 120 and the X-ray irradiation window B1 displayed by being overlapped on the camera image is based on a two-dimensional coordinate system, the control unit 140 has to convert the calculated information on the three-dimensional coordinates of the X-ray irradiation region E into coordinates based on a two-dimensional image coordinate system.

In addition, since the coordinates of the capturing unit 120 and the global coordinate system are different, the global coordinate system has to be converted into a camera coordinate system to convert the information on the three-dimensional coordinates of the X-ray irradiation region E into coordinates based on the two-dimensional image coordinate system. That is, the global coordinate system has to be converted into the camera coordinate system, and the information on the three-dimensional coordinates converted into coordinates based on the camera coordinate system has to be converted into coordinates based on the two-dimensional image coordinate system.

The control unit 140 may use the two-dimensional coordinates obtained as above to display the X-ray irradiation window B1 by overlapping the X-ray irradiation window B1 on the camera image on the display unit 150.

In addition, the control unit 140 performs image processing of an image of the light irradiation region L of the collimator 113 acquired by the capturing unit 120 to generate the X-ray irradiation window B2 displayed on the display unit 150 (411).

As described above, the X-ray irradiation window B1 may be displayed on the display unit 150 using the coordinate information, or the X-ray irradiation window B2 may be displayed by extracting a boundary of the light irradiation region L shown in the camera image acquired by the capturing unit 120 through image processing.

When the X-ray irradiation window B1 generated using the coordinate information and the X-ray irradiation window B2 generated through image processing do not match (No to 412), the control unit 140 performs calibration (413).

The X-ray imaging apparatus 100 according to the disclosed embodiment undergoes a calibration process that matches the light irradiation region and the actual X-ray irradiation region by adjusting a collimator lamp and a reflector and determines camera parameters such as a principal point, a focal length, an installation angle, etc. of the capturing unit 120 such that an X-ray irradiation window displayed on the display unit 150 may accurately show the actual X-ray irradiation region E.

When an error does not occur in the calibration process, the X-ray irradiation window generated using coordinate information and the X-ray irradiation window generated through image processing match each other. Consequently, when the X-ray irradiation window and the X-ray irradiation window do not match each other, an error may be determined as having occurred in the calibration process described above.

Consequently, the control unit 140 performs a process of verifying whether an error has occurred in the calibration process described above by performing a process of comparing the X-ray irradiation window B1 generated using coordinate information and the X-ray irradiation window B2 generated through image processing with each other to find out whether the two match.

Since discordance between the X-ray irradiation windows generated using the two methods described above implies that an error has occurred in the calibration process, the control unit 140 may display a message or the like requesting that calibration be performed through the display unit 150. The user may check the message and re-perform the calibration process described above.

In addition, rather than displaying the message that requests that calibration be performed, the control unit 140 may calculate a degree of discordance to, calculate a camera parameter for solving the discordance when the X-ray irradiation windows generated using the two methods described above do not match each other. The control unit 140 may calculate a focal length and a principal point of the capturing unit 120 required for solving the discordance based on discordance information and may calculate variables required for converting the global coordinate system into the camera coordinate system. In addition, in the disclosed embodiment, an offset may occur due to a difference between the focal point of the capturing unit 120 and a focal point of the X-ray tube 111. The control unit 140 may use the discordance information to calculate parameters required to compensate for the offset. The control unit 140 may automatically perform calibration using the parameters calculated as above or assist the user to perform calibration by displaying the calculated parameters through the display unit 150.

Figure 44:
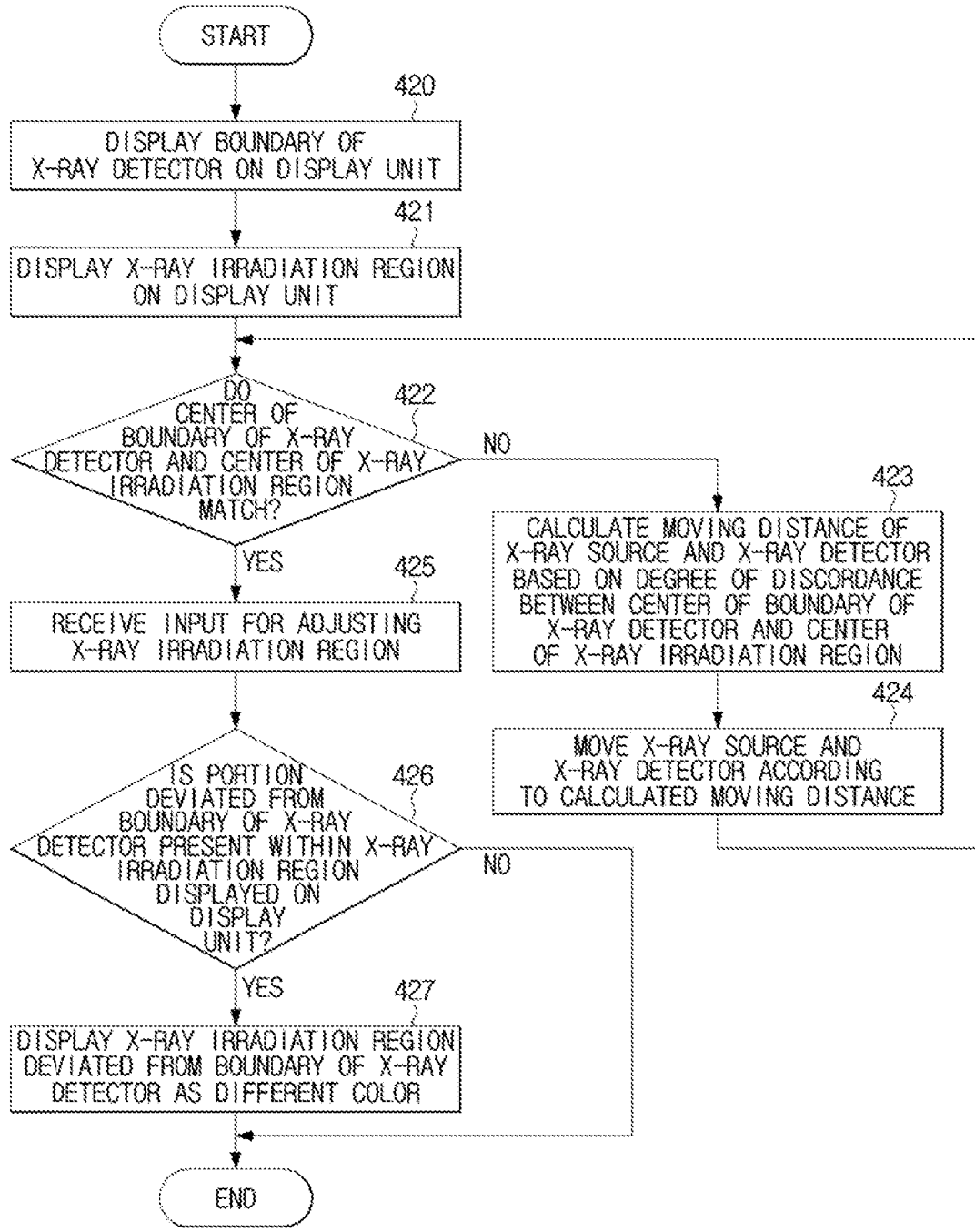
FIG. 44 is a flowchart illustrating an example of a method for aligning an X-ray source and an X-ray detector with each other in the method for controlling an X-ray imaging apparatus according to an embodiment.

FIG. 44 is a flowchart illustrating an example of a method for aligning an X-ray source and an X-ray detector to each other in the method for controlling an X-ray imaging apparatus according to an embodiment.

As illustrated in FIG. 44, the control unit 140 displays a boundary of the X-ray detector 200 and an X-ray irradiation region on the display unit 150 (421).

The control unit 140 may generate the X-ray irradiation window B3 by the method using coordinate information or the method for extracting a boundary of an X-ray irradiation region through image processing described above to display the X-ray irradiation region, and may display the generated X-ray irradiation window B3 by overlapping the generated X-ray irradiation window B3 on the camera image 152.

In addition, the control unit 140 may generate the detector boundary line B4 showing the boundary of the X-ray detector 200 by the method using coordinate information or the method for extracting the boundary of the X-ray detector 200 through image processing described above to display the boundary of the X-ray detector 200, and may display the generated detector boundary line B4 by overlapping the generated detector boundary line B4 on the camera image 152.

The X-ray irradiation window B3 and the detector boundary line B4 displayed by being overlapped on the camera image 152 may be distinguished from each other by using different colors or by using a dotted line and a solid line.

The control unit 140 determines whether a center of the detector boundary line B4 and a center of the X-ray irradiation window B3 match (422), and when the two do not match (No to 422), calculates a moving distance of the X-ray source 110 and the X-ray detector 200 based on a degree of discordance between the center of the detector boundary line B4 and the center of the X-ray irradiation window B3 (423). In addition, the moving distances may be calculated together, and the control unit 140 moves and aligns the X-ray source 110 and the X-ray detector 200 according to the calculated moving distances and moving direction (424).

When intervals between four vertices forming the X-ray irradiation window B3 and four vertices forming the detector boundary line B4 entirely match each other, the control unit 140 may determine that the X-ray detector 200 and the X-ray source 110 are aligned with each other.

Alternatively, when the center of the detector boundary line B4 and the center of the X-ray irradiation window B3 match (Yes to 422), the control unit 140 may determine that the X-ray detector 200 and the X-ray source 110 are aligned with each other.

When the intervals between the four vertices forming the X-ray irradiation window B3 and the four vertices forming the detector boundary line B4 are different from each other or the center of the X-ray irradiation window B3 and the center of the detector boundary line B4 do not match, the control unit 140 may determine that the X-ray detector 200 and the X-ray source 110 are not aligned with each other. In this case, the control unit 140 may calculate the intervals g2, g3, g4, and g5 between the four vertices of the X-ray irradiation window B3 and the four vertices of the detector boundary line respectively corresponding thereto and calculate a moving distance and a moving direction of the X-ray source 110 or the X-ray detector 200 that may match the calculated intervals to each other. The control unit 140 may match the intervals by moving the X-ray source 110 or the X-ray detector 200 based on the moving distance and the moving direction of the X-ray source 110 or the X-ray detector 200 calculated as above. Alternatively, the control unit 140 may also guide the user to move the X-ray source 110 or the X-ray detector 200 by displaying the calculated moving distance and moving direction of the X-ray source 110 or the X-ray detector 200 through the display unit 150.

Alternatively, the control unit 140 may calculate the interval g1 between the center of the X-ray irradiation window B3 and the center of the detector boundary line B4 and, may calculate the moving direction or the moving distance of the X-ray source 110 or the X-ray detector 200 that matches the center of the X-ray irradiation window B3 and the center of the detector boundary line B4 based on the calculated interval. The control unit 140 may match the center of the X-ray irradiation window B3 and the center of the detector boundary line B4 by moving the X-ray source 110 or the X-ray detector 200 based on the moving direction and the moving distance of the X-ray source 110 or the X-ray detector 200 calculated as above. By this, the control unit 140 may match centers of the actual X-ray irradiation region and the X-ray detector 200. Alternatively, the control unit 140 may also guide the user to move the X-ray source 110 or the X-ray detector 200 by displaying the calculated moving direction and moving distance of the X-ray source 110 or the X-ray detector 200 through the display unit 150.

When the center of the detector boundary line B4 and the center of the X-ray irradiation window B3 match, the control unit 140 receives an adjustment command for adjusting an X-ray irradiation region (425), and when a portion deviated from the detector boundary line B4 is present within the X-ray irradiation window B3 displayed on the display unit 150 (Yes to 426), the control unit 140 displays the portion deviated from the detector boundary line B4 (427).

When the X-ray source 110 and the X-ray detector 200 are aligned with each other, the user may input a predetermined operation command through the input unit 160 to adjust a position, size, or form of the X-ray irradiation window B3.

The X-ray irradiation window B3 may deviate from the detector boundary line B4 while the user adjusts the X-ray irradiation window B3. When a region deviated from the boundary of the X-ray detector 200 is also irradiated with X-rays, unnecessarily excessive X-ray exposure may occur. Consequently, when the X-ray irradiation window B3 deviates from the detector boundary line B4, the control unit 140 may inform the user by displaying the region B3-2 that is deviated from the detector boundary line B4 and the region B3-1 that is present within the detector boundary line B4 with different colors to prevent excessive X-ray exposure. For example, the control unit 140 may display the region that is present within the detector boundary line B4 as green and the region that is deviated from the detector boundary line B4 as red to inform the user that the X-ray irradiation window has deviated from the boundary of the X-ray detector 200. Alternatively, notification regarding a region deviated from the boundary of the X-ray detector 200 may also be provided using a dotted line and a solid line instead of using different colors.

Informing that the X-ray irradiation window has deviated from the boundary of the X-ray detector 200 using different colors or using a dotted line and a solid line is merely an example, and a sound or a vibration of the input unit 160 may also be used. That is, the X-ray imaging apparatus 100 according to the disclosed embodiment may inform the user that the X-ray irradiation window displayed on the display unit 150 has deviated from the boundary of the X-ray detector 200 using various methods based on a visual, aural, or tactile stimulation.

Figure 45:
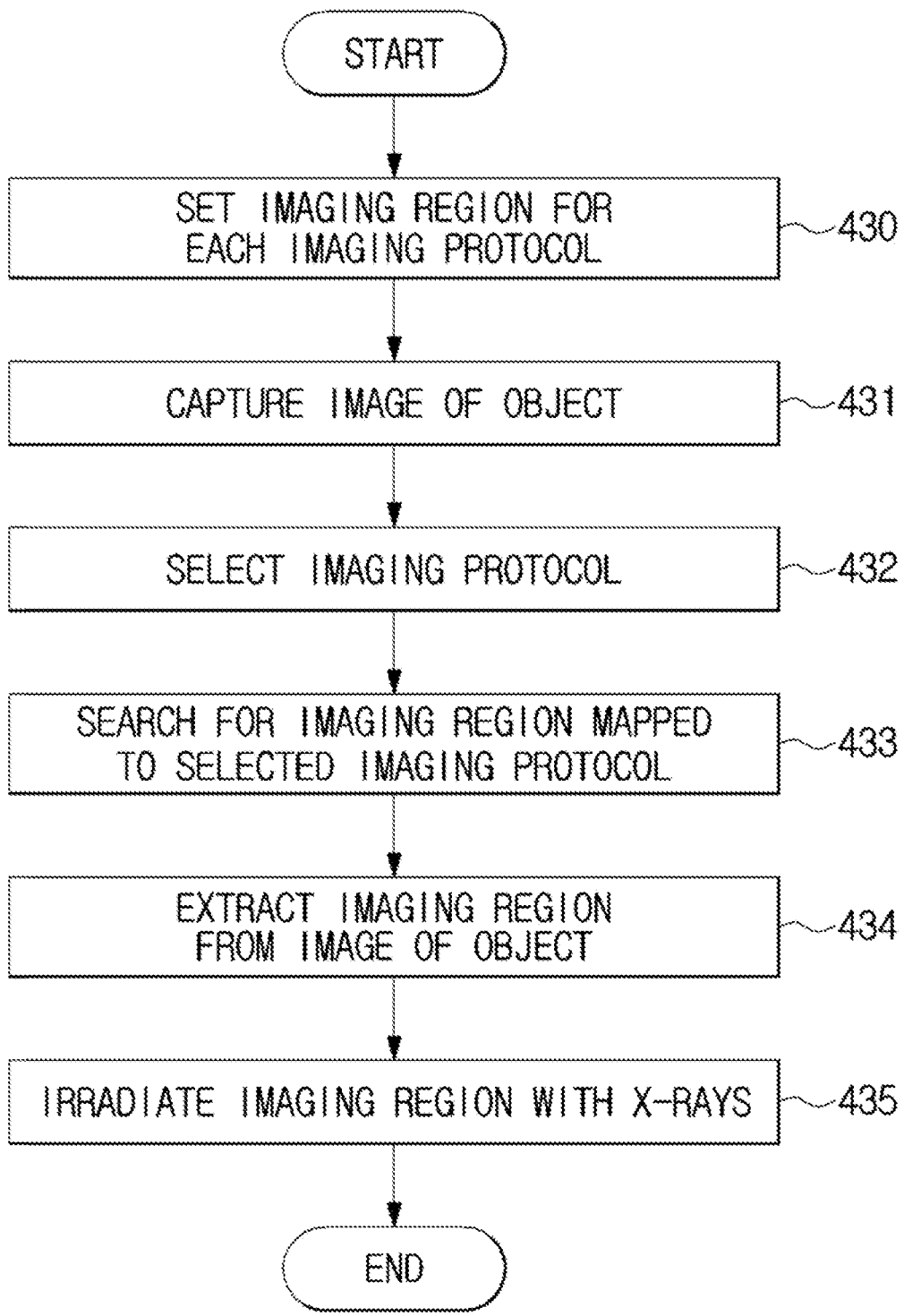
FIG. 45 is a flowchart related to a method for setting an imaging protocol in the method for controlling an X-ray imaging apparatus according to an embodiment.

FIG. 45 is a flowchart related to a method for setting an imaging protocol in the method for controlling an X-ray imaging apparatus according to an embodiment.

Referring to FIG. 45, an imaging region is set for each of a plurality of imaging protocols (430). The imaging region may be set according to the user's input. For this, the display unit 150 may display the imaging protocol setting window 154. The imaging protocol setting window 154 may include the protocol list 154c.

The user may select an imaging protocol whose imaging region is desired to be set by the user from the protocol list 154c using the input unit 160. The object model 154b having a shape similar to that of an object may be displayed on the display unit 150 to receive a setting of an imaging region, and the user may adjust a position and size of the imaging window 154a displayed on the object model 154b to set an imaging region of the selected imaging protocol. An imaging region set for each of the imaging protocols is stored in the storage unit 170.

Then, prior to performing X-ray imaging, the capturing unit 120 is used to capture a camera image (431). A time difference may exist between X-ray imaging and the imaging region for each of the imaging protocols.

An imaging protocol is selected (432). The imaging protocol may be selected by the user's input.

An imaging region mapped to the selected imaging protocol is searched for (433). The imaging region may be searched for by the control unit 140. For example, when the selected imaging protocol is a chest PA, an imaging region mapped and stored in the chest PA is searched for.

The imaging region is extracted from a camera image (434). For example, the control unit 140 may extract an imaging region from the camera image 152 by applying image processing such as an object recognition algorithm. For example, edge detection may be applied to the camera image 152 to extract a silhouette or a form of the object and detect a few features such as a length from head to toe (a height), a width of the head or shoulders, and a length of a leg required to recognize the imaging region.

The imaging region is irradiated with X-rays to perform X-ray imaging (435). When the imaging region is extracted from the camera image 152 by the control unit 140, the control unit 140 may control the collimator 113 to correspond the X-ray irradiation region E to the imaging region. When the X-ray source 110 or the X-ray detector 200 should be moved, the X-ray source 110 or the X-ray detector 200 may be moved to a position corresponding to the imaging region. In addition, when the imaging region has a range which cannot be covered by performing a single X-ray imaging, the imaging region may be divided and stitching imaging may be performed.

Figure 46:
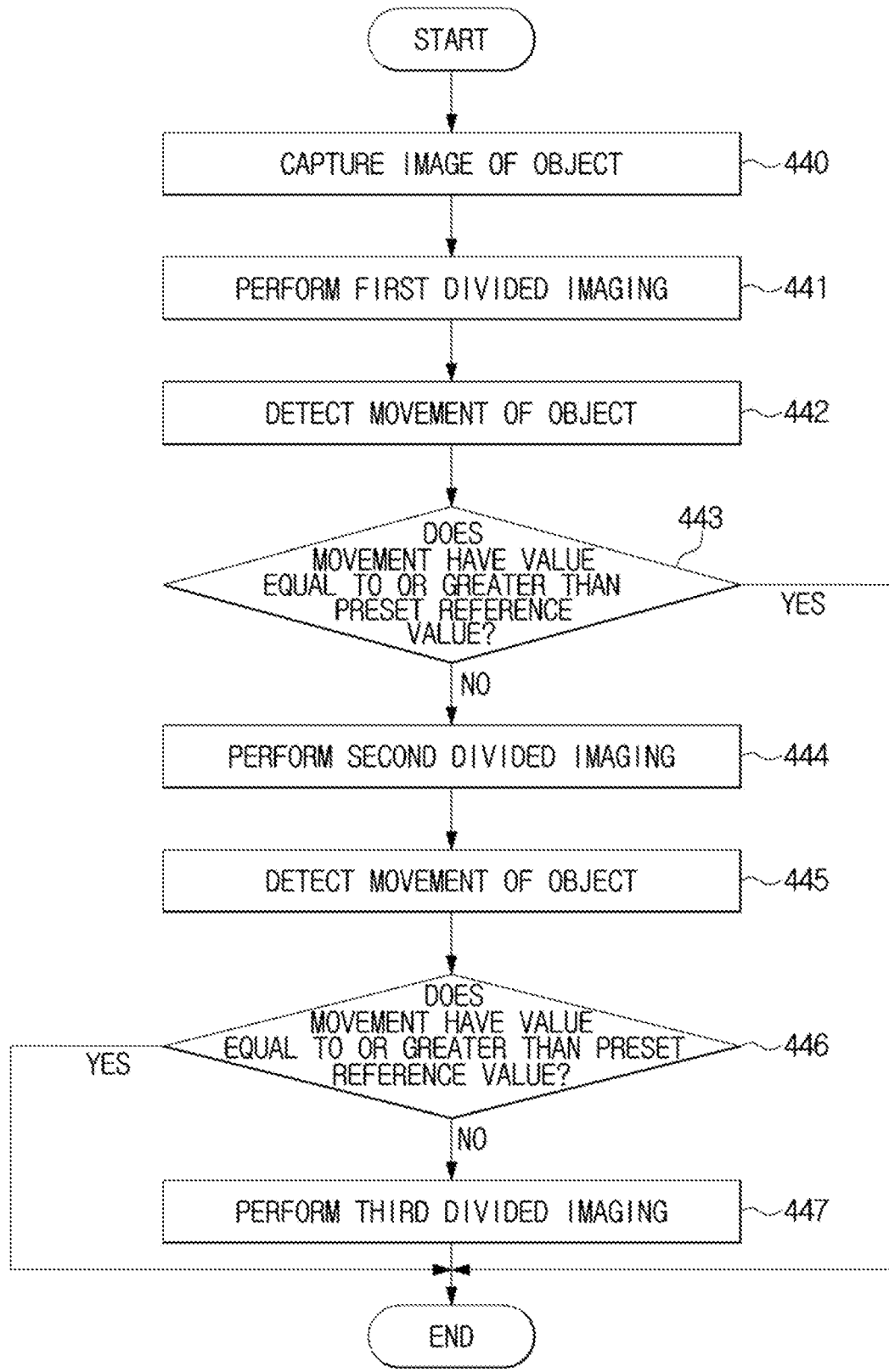
FIG. 46 is a flowchart related to a method for determining whether divided imaging has stopped according to a movement of an object in the method for controlling an X-ray imaging apparatus according to an embodiment.

FIG. 46 is a flowchart related to a method for determining whether divided imaging has stopped according to a movement of an object in the method for controlling an X-ray imaging apparatus according to an embodiment. In this example, stitching imaging is performed, and a stitching region is divided into a first divided region, a second divided region, and a third divided region.

Referring to FIG. 46, the capturing unit 120 is used to capture a camera image (440). The capturing unit 120 may capture a video in real time or capture a camera image until X-ray imaging is finished.

First divided imaging is performed (441). For this, a position or tilt angle of the X-ray source 110 may be controlled to be a position or an angle corresponding to the first divided region, and a position of the X-ray detector 200 may be controlled to be a position corresponding to the first divided region.

A movement of the object is detected (442). Specifically, the control unit 140 may compare an orientation of the object shown in the current camera image with an orientation of the object shown in the camera image during the first divided imaging to detect the movement.

When the detected movement has a value equal to or greater than a preset reference value (Yes to 443), matching the first divided X-ray image and the second divided X-ray image may be determined to be impossible even when divided imaging is performed and imaging may be stopped.

When the detected movement does not have a value equal to or greater than the preset reference value (No to 443), second divided imaging is performed (444).

A movement of the object is detected (445). The control unit 140 may compare an orientation of the object shown in the current camera image with an orientation of the object shown in the camera image during the second divided imaging to detect the movement.

When the detected movement has a value equal to or greater than the preset reference value (Yes to 446), matching the second divided X-ray image and the third divided X-ray image may be determined to be impossible even when divided imaging is performed and imaging may be stopped.

When the detected movement does not have a value equal to or greater than the preset reference value (No to 446), third divided imaging is performed (447).

Alternatively, a warning may be output to the user without stopping the capturing to guide the user to guide the orientation of the object.

When the third divided imaging is finished, the first divided X-ray image, the second divided X-ray image, and the third divided X-ray image may be stitched together to generate one stitched-together image.

Figure 47:
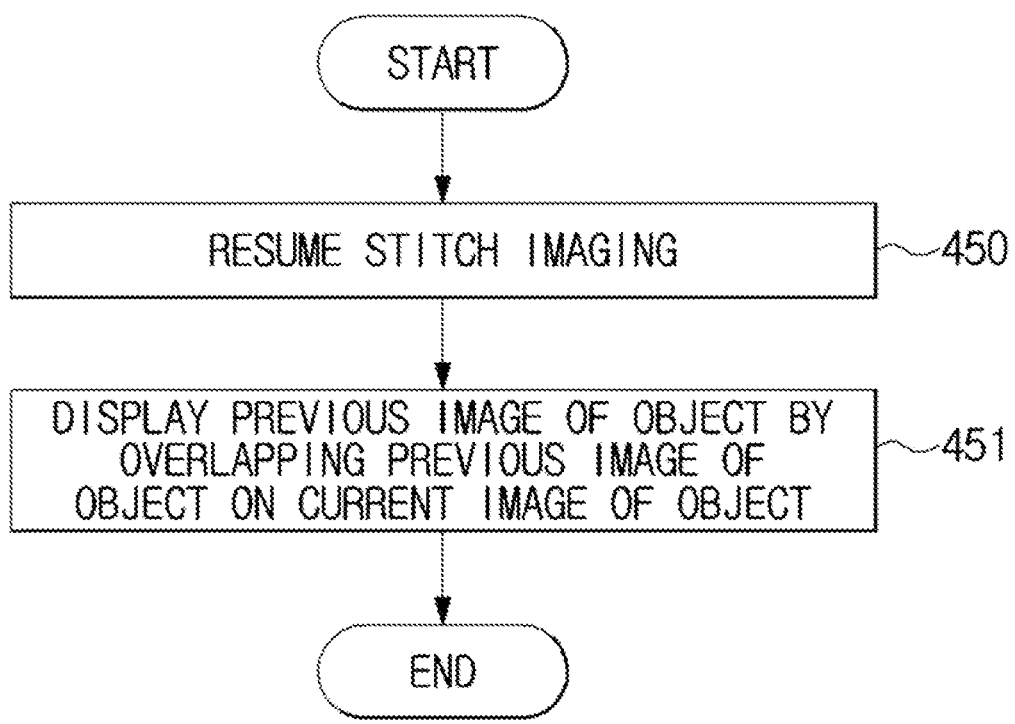
FIG. 47 is a flowchart related to a case of resuming stitching imaging in the method for controlling an X-ray imaging apparatus according to an embodiment.

FIG. 47 is a flowchart related to a case of resuming stitching imaging in the method for controlling an X-ray imaging apparatus according to an embodiment.

As described above, imaging may be stopped while divided imaging is partially completed when the movement of the object has a value equal to or greater than a reference value, or a condition of the object is unstable or critical.

Divided X-ray images that have been already captured as well as camera images captured while divided imaging is performed may be stored in the storage unit 170 when stitching imaging is stopped. Information on divided regions for stitching imaging may also be stored in the camera images.

In addition, when stitching imaging is resumed afterwards (450), the control unit 140 may search for and load a camera image mapped and stored for the resumed stitching imaging in the storage unit 170.

The display unit 150 may display a previous camera image by allowing the previous camera image to overlap the current camera image (451). The user may guide the orientation of the object with reference to the overlapped camera images. Since the two images overlap each other, the user may accurately recognize the difference between orientations of the object shown in the two images and guide the current orientation of the object to match the orientation of the object during the second divided imaging.

Figure 48:
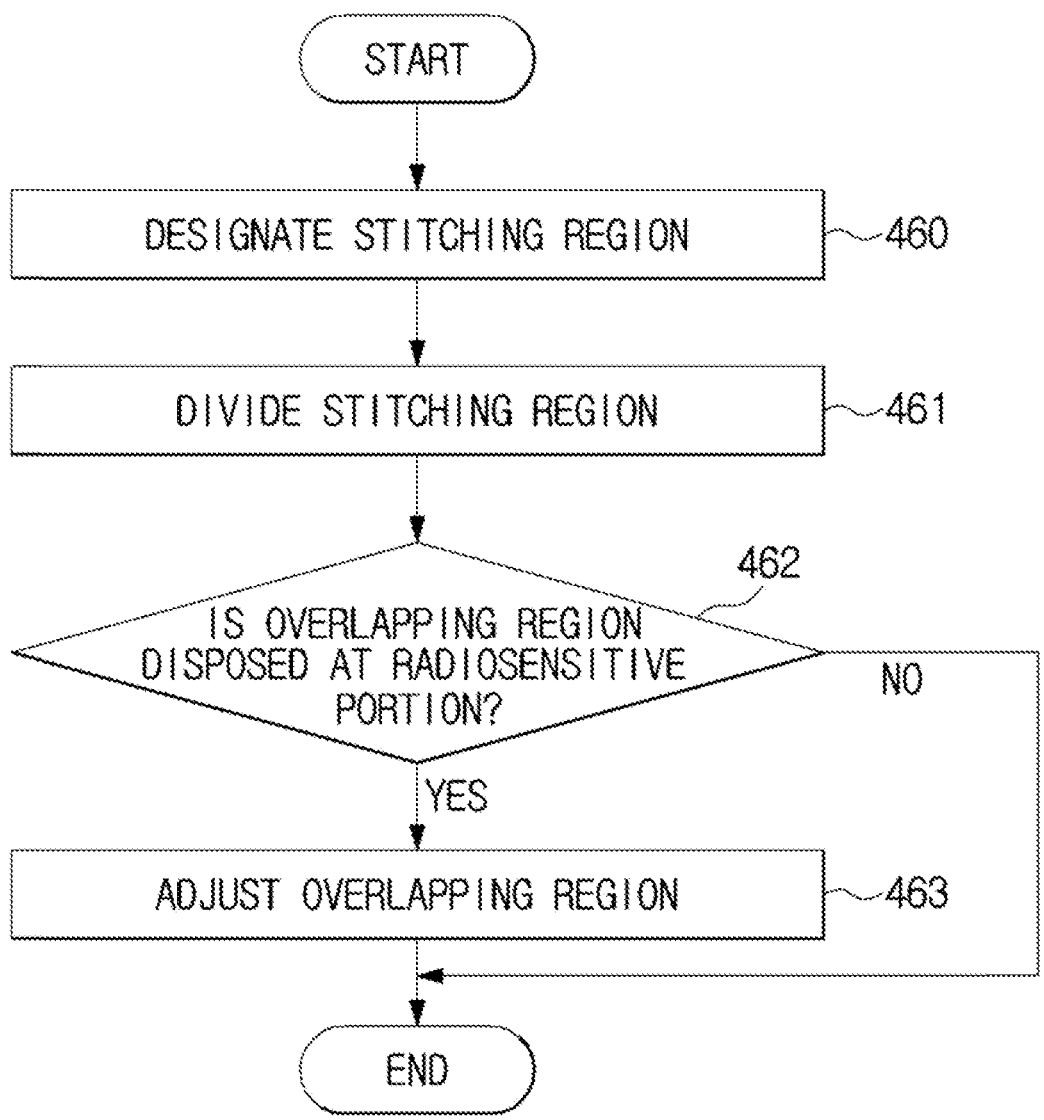
FIG. 48 is a flowchart related to a method for controlling an overlapping region in the method for controlling an X-ray imaging apparatus according to an embodiment.

FIG. 48 is a flowchart related to a method for controlling an overlapping region in the method for controlling an X-ray imaging apparatus according to an embodiment.

Referring to FIG. 48, a stitching region in which stitching imaging will be performed is designated (460). The stitching region may be designated by a direct input of a user or may also be automatically designated by selecting an imaging protocol. That is, an imaging region corresponding to the selected imaging protocol may be designated as the stitching region.

The stitching region is divided (461). For example, the stitching region may be divided into uniform sizes in consideration of a size of the stitching region and a size of the region to be detected by the X-ray detector 200.

Whether an overlapping region is disposed at a radiosensitive portion is determined (462). Whether the overlapping region is disposed at a radiosensitive portion may also be determined by applying an object recognition algorithm. For example, a portion disposed at a central portion of a length from head to toe and from which thighs originate may be determined as a portion at which a genital organ is disposed, and a portion spaced apart 20 cm or less downward from armpit portions or shoulders may be determined as a portion at which the heart is disposed. Information related to a radiosensitive portion may be pre-stored in the storage unit 170 or may also be added or modified by the user.

When the overlapping region is disposed at a radiosensitive portion (Yes to 462), the overlapping region may be adjusted (463). The overlapping region may be adjusted automatically by the control unit 140 or according to the user's input. In the former case, the control unit 140 may adjust a boundary of a corresponding divided region so that the overlapping region may avoid the radiosensitive portion.

In the latter case, a position of the radiosensitive portion may be displayed on the display unit 150 to guide the user's input.

FIG. 49 is a flowchart related to a method for presetting a size of an object in the method for controlling an X-ray imaging apparatus according to an embodiment.

Referring to FIG. 49, a size of an object is set and stored (470). For example, the display unit 150 may display the object size setting screen 156. Specifically, the display unit 150 may display the object model 154b, and the user may use to input unit 160 to classify sizes of an object. In a detailed example, a height, a height of shoulders, and a length of legs may be designated and mapped as particular sizes. The height, the height of shoulders, and the length of legs may also be designated as particular values and may also be designated as a predetermined range. The sizes of the object classified by the user may be stored in an object size DB, and the object size DB may be stored in the storage unit 170. Although sizes of an object may be classified as large, medium, small, child, baby, etc., an embodiment of the X-ray imaging apparatus 100 is not limited thereto and the sizes may be further segmented or generalized.

An X-ray irradiation condition is set for each of a plurality of object sizes and stored (471). For example, the settings window 151 through which an X-ray irradiation condition may be set may be displayed on the display unit 150. The user may set the X-ray irradiation condition for each of the object sizes. The X-ray irradiation condition that can be set may include a tube voltage, a tube current, and an exposure time, and may also include a position at which X-ray imaging is performed (a stand and a table for performing X-ray imaging), a collimator size, a position of an AEC sensor, sensitivity, density, and a grid. The X-ray irradiation conditions set for each of the object sizes may be stored in the storage unit 170.

After the object sizes and the X-ray irradiation conditions are set, the capturing unit 120 may capture a camera image when the object is disposed in front of the X-ray detector 200 for X-ray imaging. In addition, the control unit 140 analyzes the camera image to determine a size of the object (472). For example, the control unit 140 may apply edge detection to the camera image to extract a silhouette of the object and may also estimate an approximate size of the object in consideration of the size of the silhouette of the object shown in the camera image, the SID, or the SOD.

An X-ray irradiation condition corresponding to the object size is searched for (473). Then, an X-ray source is controlled according to a found X-ray irradiation condition (474). In addition, when the X-ray irradiation condition stored corresponding to the object size includes a condition related to the X-ray detector 200, the X-ray detector 200 may of course be further controlled.

Some of the operations of the X-ray imaging apparatus and the method for controlling the same described above may be stored as programs in a computer-readable recording medium. The recording medium may be a magnetic recording medium such as a read-only memory (ROM), a floppy disk, and a hard disk, or an optical recording medium such as a compact disk (CD)-ROM and a digital versatile disk (DVD). However, types of the recording medium are not limited to the examples above.

The recording medium may be included in a server that provides applications or programs, and a work station, a sub-display device, or a mobile device may access the server via a communication protocol such as the Internet to download a corresponding program.

For example, when the display unit 150 and the input unit 160 described above are included in a mobile device, the screen described above may be displayed on the display unit 150 after the mobile device downloads, installs, and executes a program.

Steps of executing some of the operations of the control unit 140 described above may be included in the program. In this case, the mobile device may generate a control command and transmit the control command to the X-ray imaging apparatus 100.

Alternatively, the mobile device may transmit information related to a control command input by the user to the X-ray imaging apparatus 100, and the control unit 140 may control the X-ray imaging apparatus 100 according to the control command input by the user.

According to an X-ray imaging apparatus and a method for controlling the same according to an aspect, a camera image can be used to set various types of parameters related to X-ray imaging including an X-ray irradiation region and X-ray imaging can be automatically controlled.

The descriptions above are merely illustrative descriptions of the technical spirit of the present disclosure, and those of ordinary skill in the art to which the present disclosure pertains should be able to make various modifications, changes, and substitutions within a scope that does not depart from essential features of the present disclosure. Consequently, the embodiments disclosed above and the accompanying drawings are for describing, instead of limiting, the technical spirit of the present disclosure, and the scope of the technical spirit is not limited by the embodiments and the accompanying drawings. The scope should be construed by the claims below, and all technical spirits within the scope equivalent to the claims should be construed as belonging to the scope of the present disclosure.

What is claimed is:

1. An imaging apparatus, comprising:
a camera configured to capture a camera image of a target disposed on an examination table configured to be movable;
an X-ray source configured to generate and radiate X-rays;
a memory configured to store imaging protocols and to store X-ray irradiation conditions mapped to a large target, a medium target, and a small target, respectively;
a display; and
a controller configured to:
receive information regarding a selection of an imaging protocol among the stored imaging protocols,
classify a size of the target based on the camera image, as at least one from among the large target, the medium target, and the small target, and retrieve, from the memory, the X-ray irradiation conditions corresponding to the classified target,
identify a position of an imaging region of the target disposed on the examination table based on the camera image, the imaging region corresponding to the selection of the imaging protocol and the camera image being acquired with the examination table at a first distance from the X-ray source,
control the display to display the camera image of the target and an indicator indicating the imaging region on the camera image based on the identified position, and
control the X-ray source to generate and radiate the X-rays toward the target disposed on the examination table at a second distance from the X-ray source.

2. The imaging apparatus of claim 1, wherein the controller is further configured to control the display to display a graphical user interface (GUI), a graphical object having a shape of the target, and the indicator as a graphical window overlapped with the graphical object, and
wherein the GUI is configured to receive the selection of the imaging protocol.

3. The imaging apparatus of claim 2, wherein at least one from among a position of the graphical window and a size of the graphical window is configured to be adjusted via the graphical window, and
the controller is further configured to receive a result of adjusting the at least one from among the size of the graphical window and the position of the graphical window, and store, in the memory, the camera image of the target and the indicator indicating the imaging region which has been adjusted.

4. The imaging apparatus of claim 2, wherein the controller is further configured to identify a boundary of an X-ray detector and determine whether the graphical window is within the boundary of the X-ray detector.

5. The imaging apparatus of claim 4, wherein the display is configured to output a visual warning based on the graphical window not being within the boundary of the X-ray detector.

6. The imaging apparatus of claim 5, wherein the display is further configured to change a color of at least one line of the graphical window based on the at least one line being outside the boundary of the X-ray detector.

7. The imaging apparatus of claim 1, wherein the camera comprises a stereo camera.

8. The imaging apparatus of claim 1, wherein the controller is further configured to control the display to display, on a first area of a screen, a protocol list for receiving a selection input of the imaging protocol, and, based on a camera image display command being input, control the display to display the camera image on the first area of the screen instead of the displaying the protocol list.

9. The imaging apparatus of claim 1, wherein the controller is further configured to control the display to display a graphical user interface (GUI) configured to receive settings of the X-ray irradiation conditions for the size of the target for the imaging protocols, respectively, and
the memory is further configured to store the X-ray irradiation conditions for the imaging protocols based on the received settings.

10. The imaging apparatus of claim 1, wherein the controller is further configured to determine at least one from among a shape of the target and the position of the imaging region of the target by applying an object recognition algorithm to the camera image.

11. A method for controlling an imaging apparatus, the method comprising:
capturing, by a camera, a camera image of a target disposed on an examination table configured to be movable;
storing, in a memory, imaging protocols;
storing, in the memory, X-ray irradiation conditions mapped to a large target, a medium target, and a small target, respectively;
receiving information regarding a selection of an imaging protocol among the stored imaging protocols;
classifying a size of the target based on the camera image, as at least one from among the large target, the medium target, and the small target;
retrieving, from the memory, the X-ray irradiation conditions corresponding to the classified target;

identifying a position of an imaging region of the target disposed on the examination table based on the camera image, the imaging region corresponding to the selection of the imaging protocol and the camera image being acquired with the examination table at a first distance from an X-ray source;

controlling a display to display the camera image of the target and an indicator indicating the imaging region on the camera image based on the identified position; and generating and radiating X-rays toward the target disposed on the examination table at a second distance from the X-ray source.

12. The method of claim 11, further comprising:

controlling the display to display a graphical user interface (GUI), a graphical object having a shape of the target, and the indicator as a graphical window overlapped with the graphical object, wherein the GUI is configured to receive the selection of the imaging protocol.

13. The method of claim 12, further comprising:

identifying a boundary of an X-ray detector; and determining whether the graphical window is within the boundary of the X-ray detector.

14. The method of claim 13, further comprising:

controlling the display to output a visual warning based on the graphical window not being within the boundary of the X-ray detector.

15. The method of claim 14, further comprising:

controlling the display to change a color of at least one line of the graphical window based on the at least one line being outside the boundary of the X-ray detector.

* * * * *